(12) United States Patent
Miteva et al.

(10) Patent No.: US 11,230,663 B2
(45) Date of Patent: Jan. 25, 2022

(54) POLYMERIC ORGANIC NANOPARTICLES WITH ENHANCED EMISSION

(71) Applicant: Sony Corporation, Tokyo (JP)

(72) Inventors: Tzenka Miteva, Stuttgart (DE); Anthony Roberts, Stuttgart (DE); Michaela Mai, Stuttgart (DE); Markus Obermaier, Stuttgart (DE); Gabriele Nelles, Stuttgart (DE); Vitor Deichmann, Stuttgart (DE); Vladimir Yakutkin, Stuttgart (DE); Jan Rother, Stuttgart (DE)

(73) Assignee: Sony Corporation, Tokyo (JP)

( * ) Notice: Subject to any disclaimer, the term of this patent is extended or adjusted under 35 U.S.C. 154(b) by 374 days.

(21) Appl. No.: 16/085,741

(22) PCT Filed: Mar. 23, 2017

(86) PCT No.: PCT/EP2017/056905
§ 371 (c)(1),
(2) Date: Sep. 17, 2018

(87) PCT Pub. No.: WO2017/167631
PCT Pub. Date: Oct. 5, 2017

(65) Prior Publication Data
US 2019/0085237 A1    Mar. 21, 2019

(30) Foreign Application Priority Data

Mar. 31, 2016 (EP) ..................... 16163430

(51) Int. Cl.
*C09K 11/06* (2006.01)
*C09K 11/02* (2006.01)
*G01N 21/64* (2006.01)

(52) U.S. Cl.
CPC .............. *C09K 11/06* (2013.01); *C09K 11/02* (2013.01); *G01N 21/6428* (2013.01);
(Continued)

(58) Field of Classification Search
CPC .... C09K 11/06; C09K 11/02; G01N 21/6428; G01N 21/6486
See application file for complete search history.

(56) References Cited

U.S. PATENT DOCUMENTS 8,940,544 B2 * 1/2015 Suri .................. G01N 21/6428
436/172
2004/0253138 A1 12/2004 Malak
(Continued)

FOREIGN PATENT DOCUMENTS

CA       2 523 027 A1    11/2004

OTHER PUBLICATIONS

International Search Report and Written Opinion dated Jun. 28, 2017, in PCT/EP2017/056905, filed Mar. 23, 2017.
(Continued)

*Primary Examiner* — C Melissa Koslow
(74) *Attorney, Agent, or Firm* — Oblon, McClelland, Maier & Neustadt, L.L.P.

(57) ABSTRACT

The present disclosure relates to luminescent including photon up-conversion nanoparticles. These nanoparticles include a polymeric organic matrix, at least one light emitter distributed within this matrix, a stabilizing agent, and at least one metal particle enclosed within the matrix, wherein the metal particles are plasmonic nanoparticles. The present disclosure further relates to methods of manufacture and to uses of such nanoparticles.

20 Claims, 27 Drawing Sheets

(52) U.S. Cl.
CPC .. *G01N 21/6486* (2013.01); *C09K 2211/1011* (2013.01); *C09K 2211/1029* (2013.01); *C09K 2211/1092* (2013.01); *C09K 2211/14* (2013.01); *G01N 21/648* (2013.01); *G01N 2021/6432* (2013.01)

(56) References Cited

U.S. PATENT DOCUMENTS

| | | |
|---|---|---|
| 2008/0262154 A1 | 10/2008 | Behrens et al. |
| 2010/0086488 A1 | 4/2010 | Hoheisel et al. |
| 2010/0301285 A1 | 12/2010 | Miteva et al. |
| 2011/0212032 A1 | 9/2011 | Chung et al. |
| 2011/0236989 A1 | 9/2011 | Suri et al. |
| 2011/0306065 A1 | 12/2011 | Friedberg et al. |
| 2013/0171060 A1 | 7/2013 | Vo-Dinh et al. |
| 2014/0209836 A1 | 7/2014 | Behrens et al. |

OTHER PUBLICATIONS

Geng, J. et al., "Conjugated Polymer and Gold Nanoparticle Co-loaded PLGA Nanocomposites with Eccentric Internal Nanostructure for Dual-modal Targeted Cellular Imaging", Small, vol. 8, No. 15, XP055338311, Aug. 6, 2012, pp. 2421-2429.

\* cited by examiner

- Functional groups
- Triplet emitter (sensitizer)
- Emitter (could be ● ● ● ...)
- Matrix
- Inorganic (metal/magnetic)

A
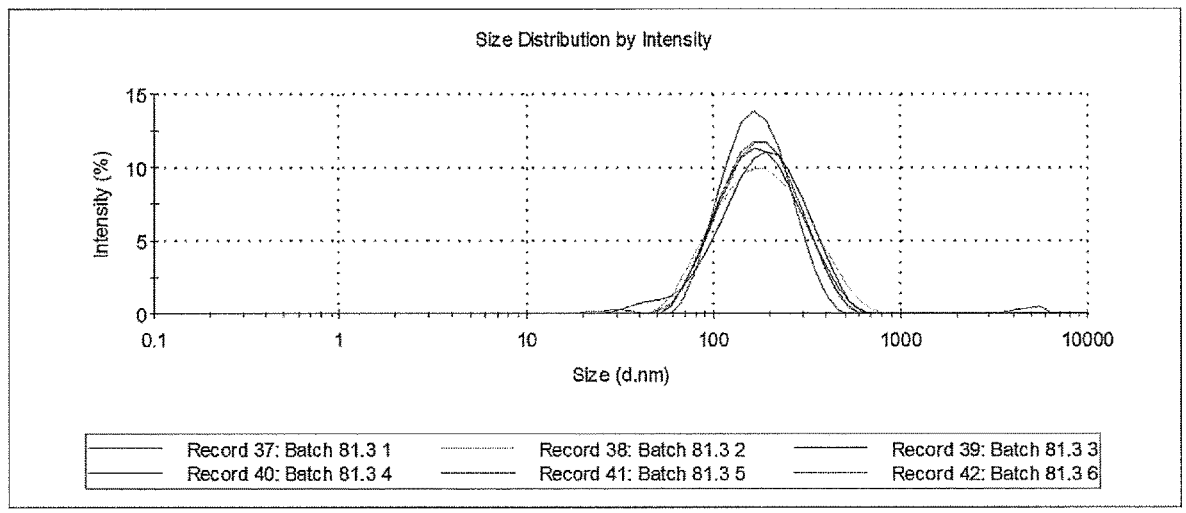
B
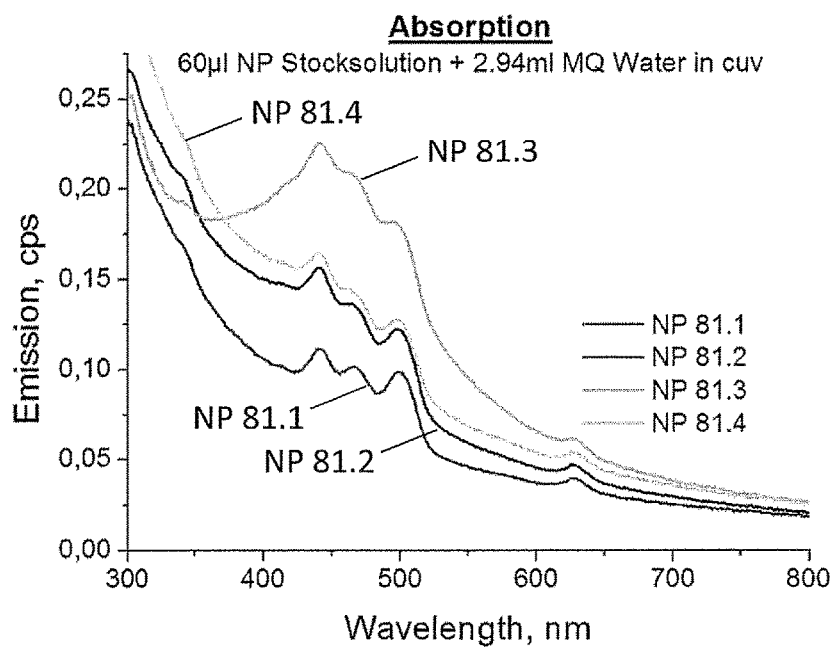
Fig. 2 A, B

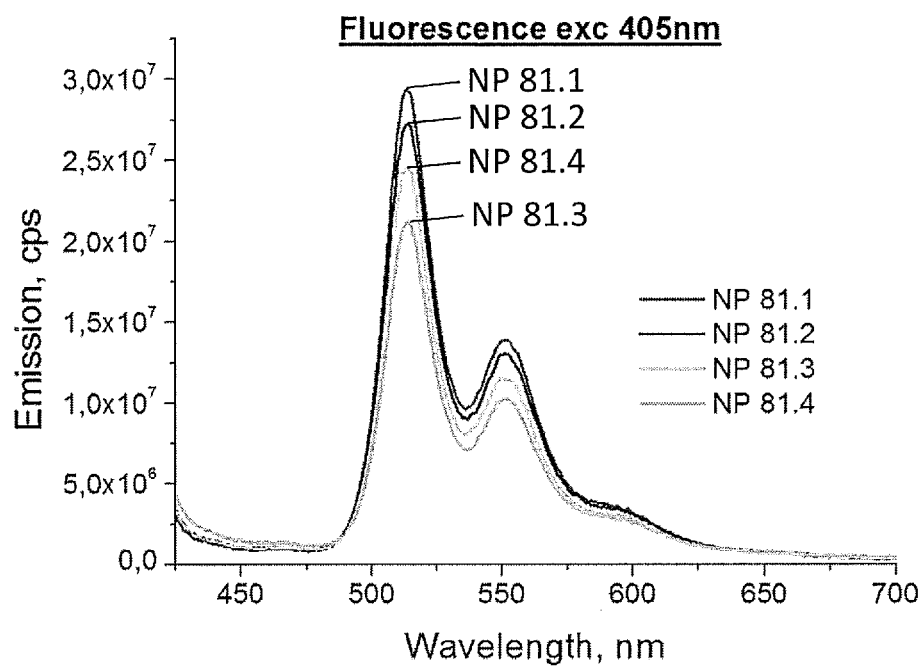
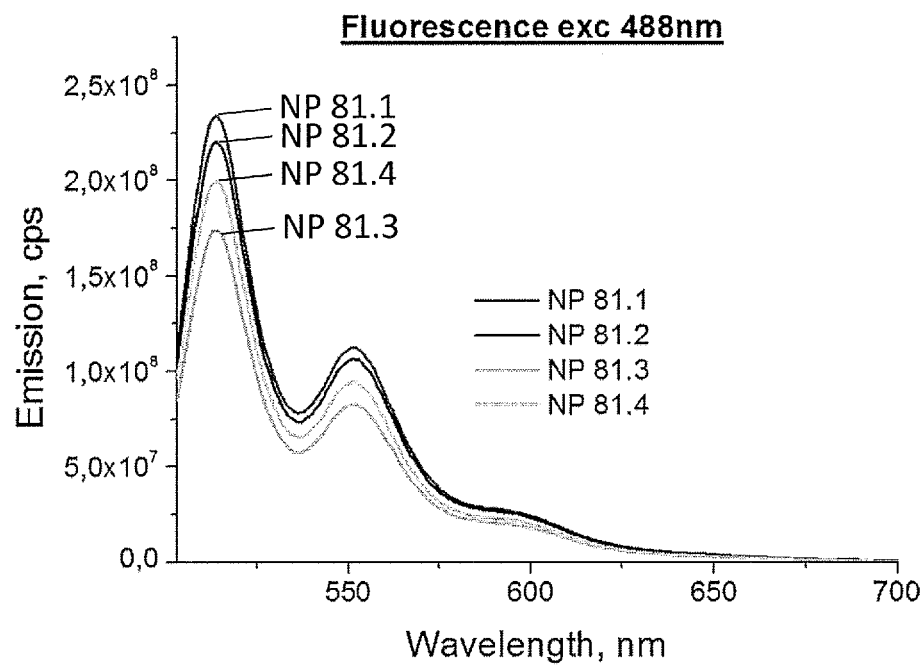
Fig. 2 C, D

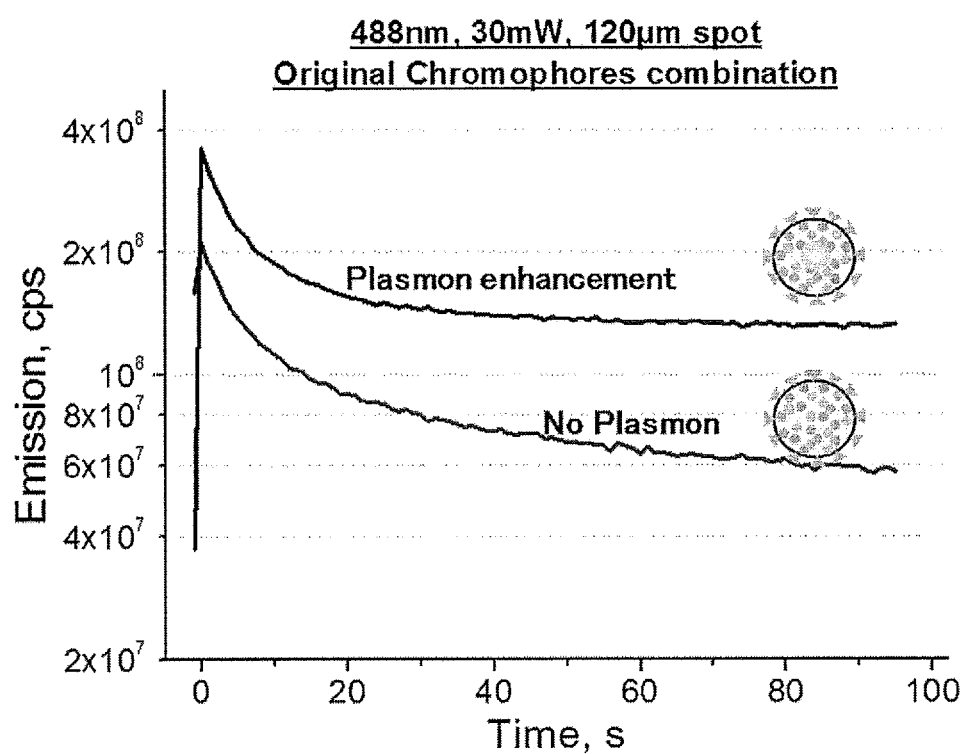
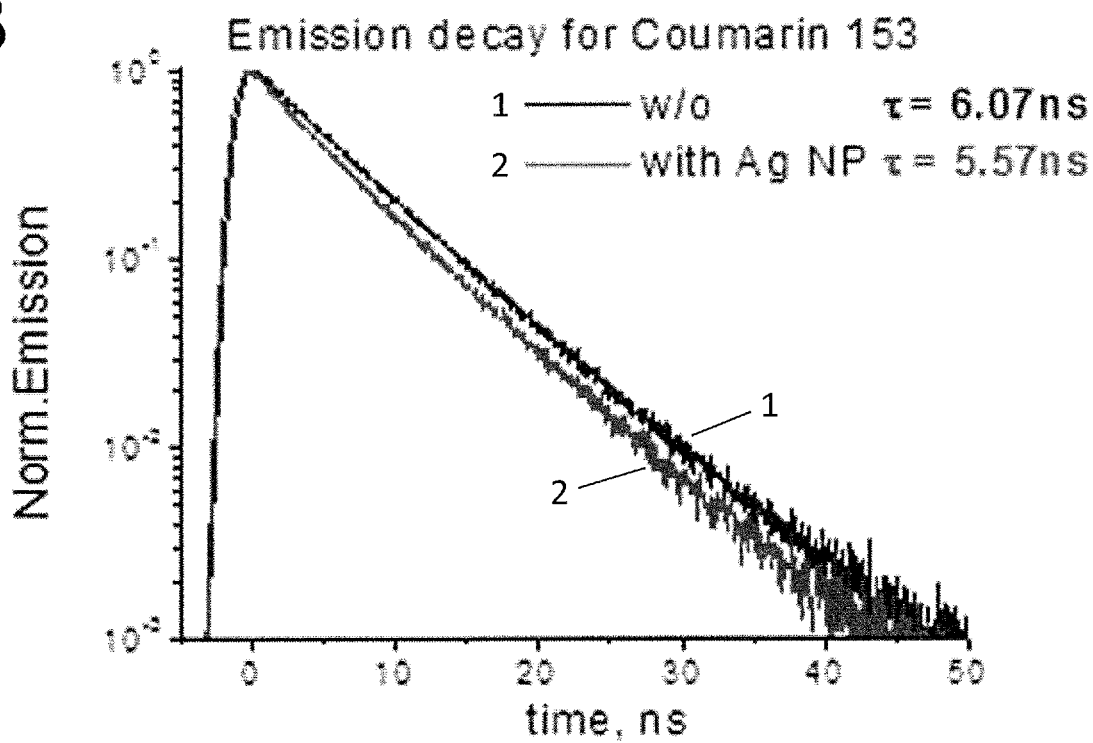
Fig. 3 A, B

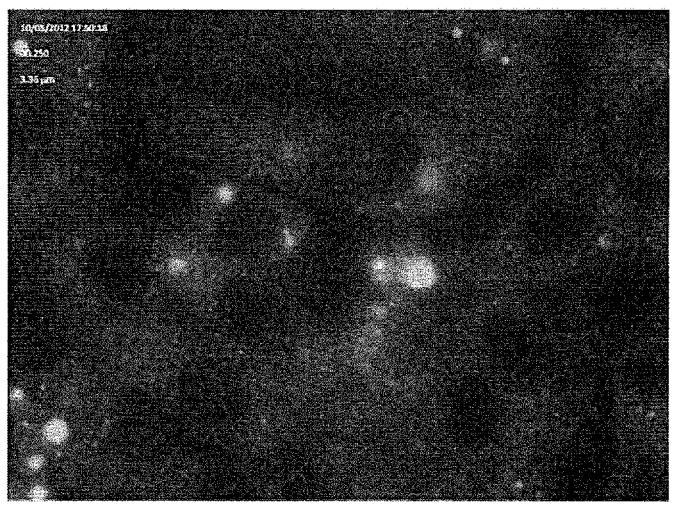
Fig. 7 B-D

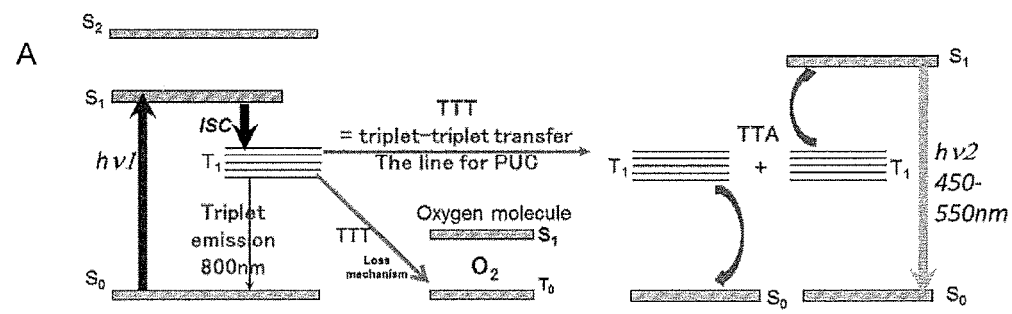
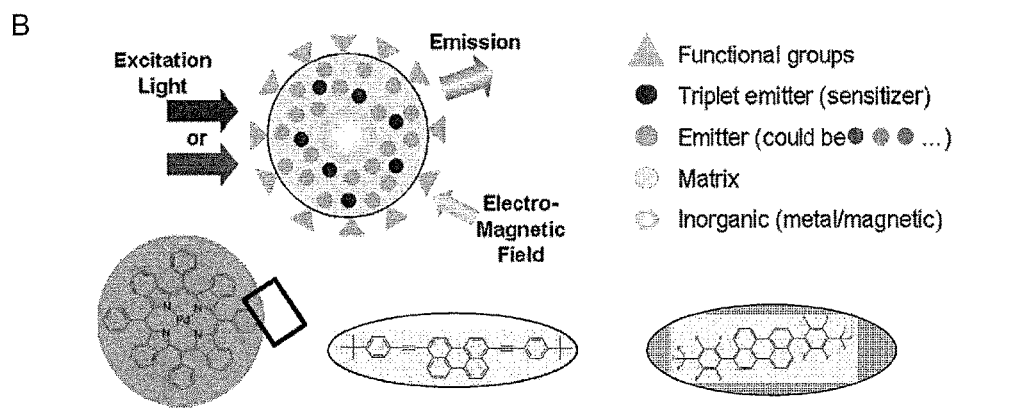
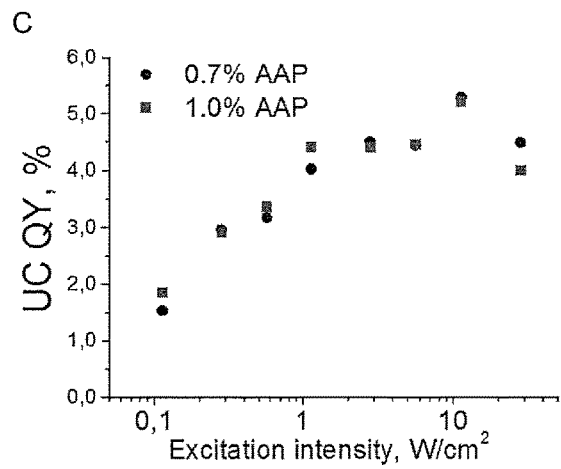
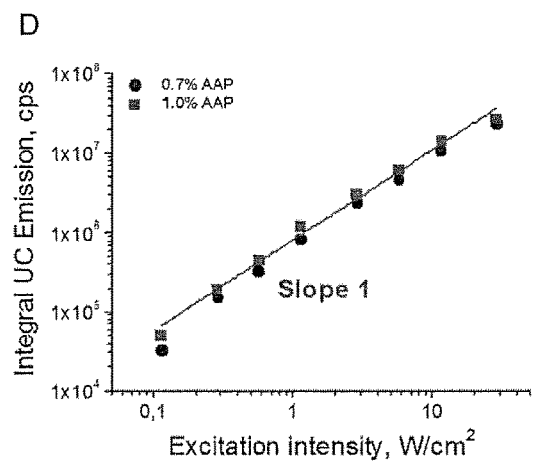
Fig. 8 A-D

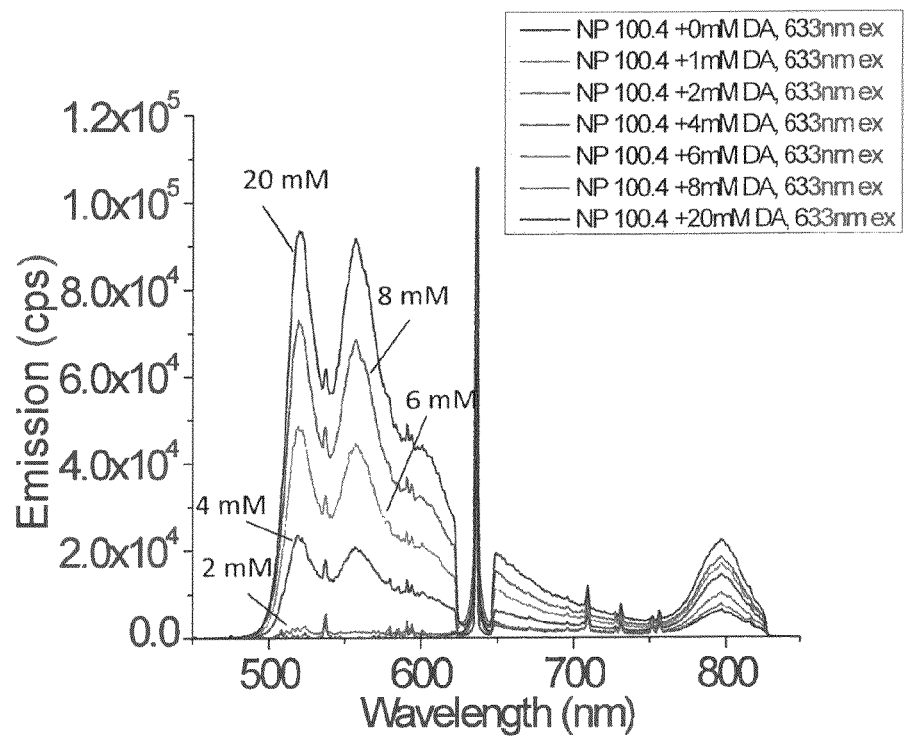
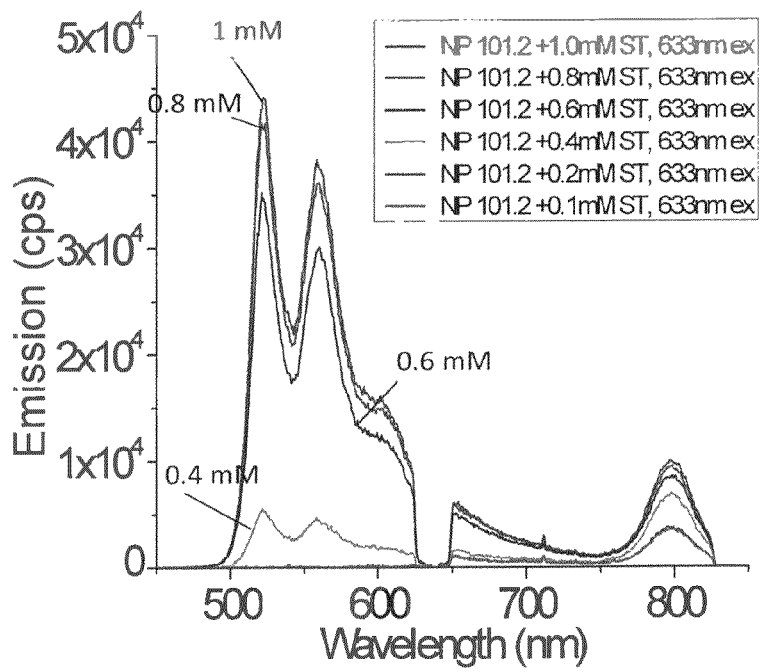
Fig. 9 A-B

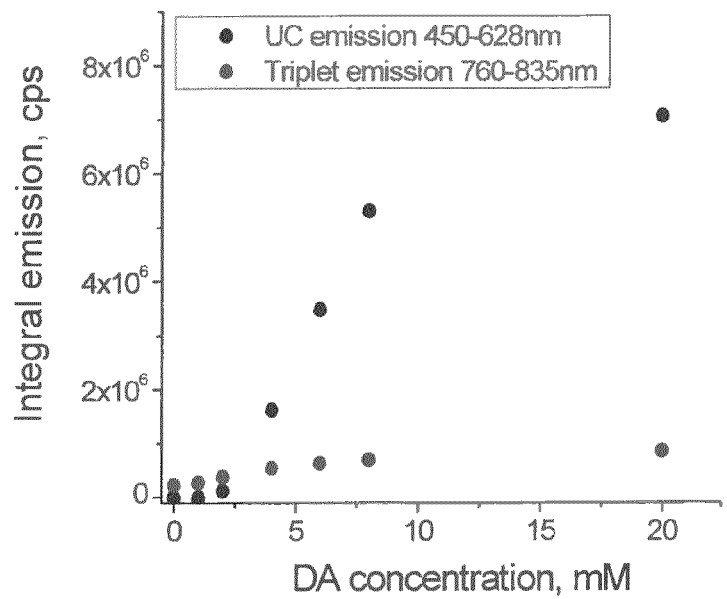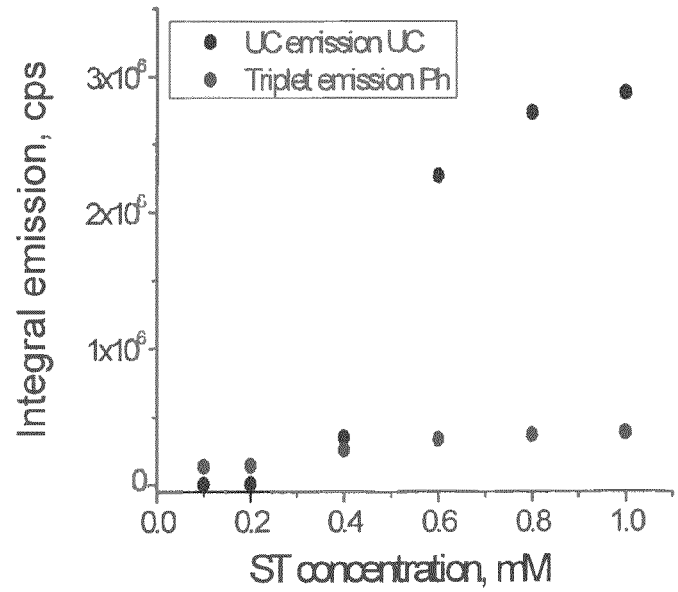
Fig. 9, C-D

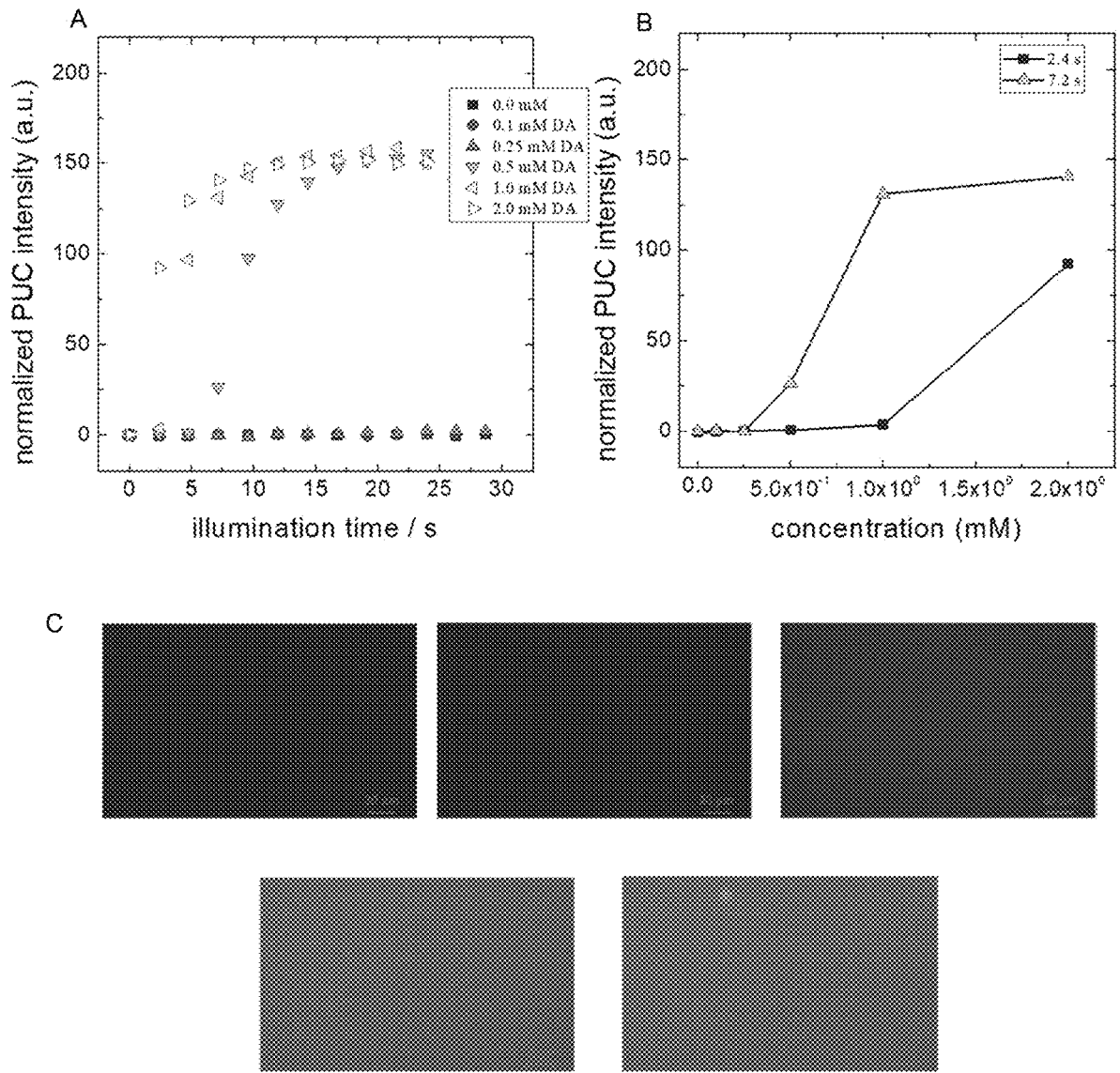
Fig. 11 A-C

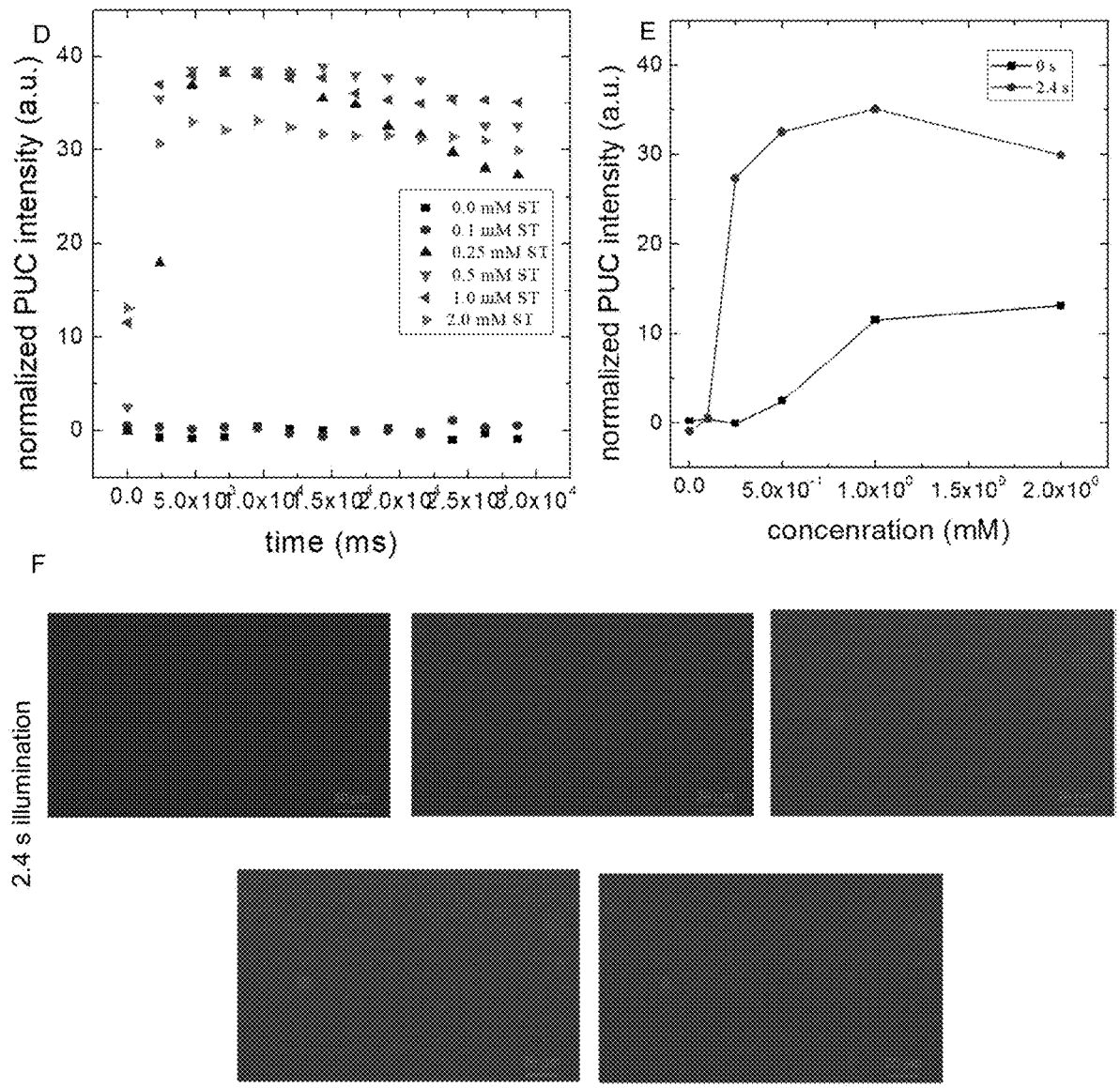
Fig. 11 D-F

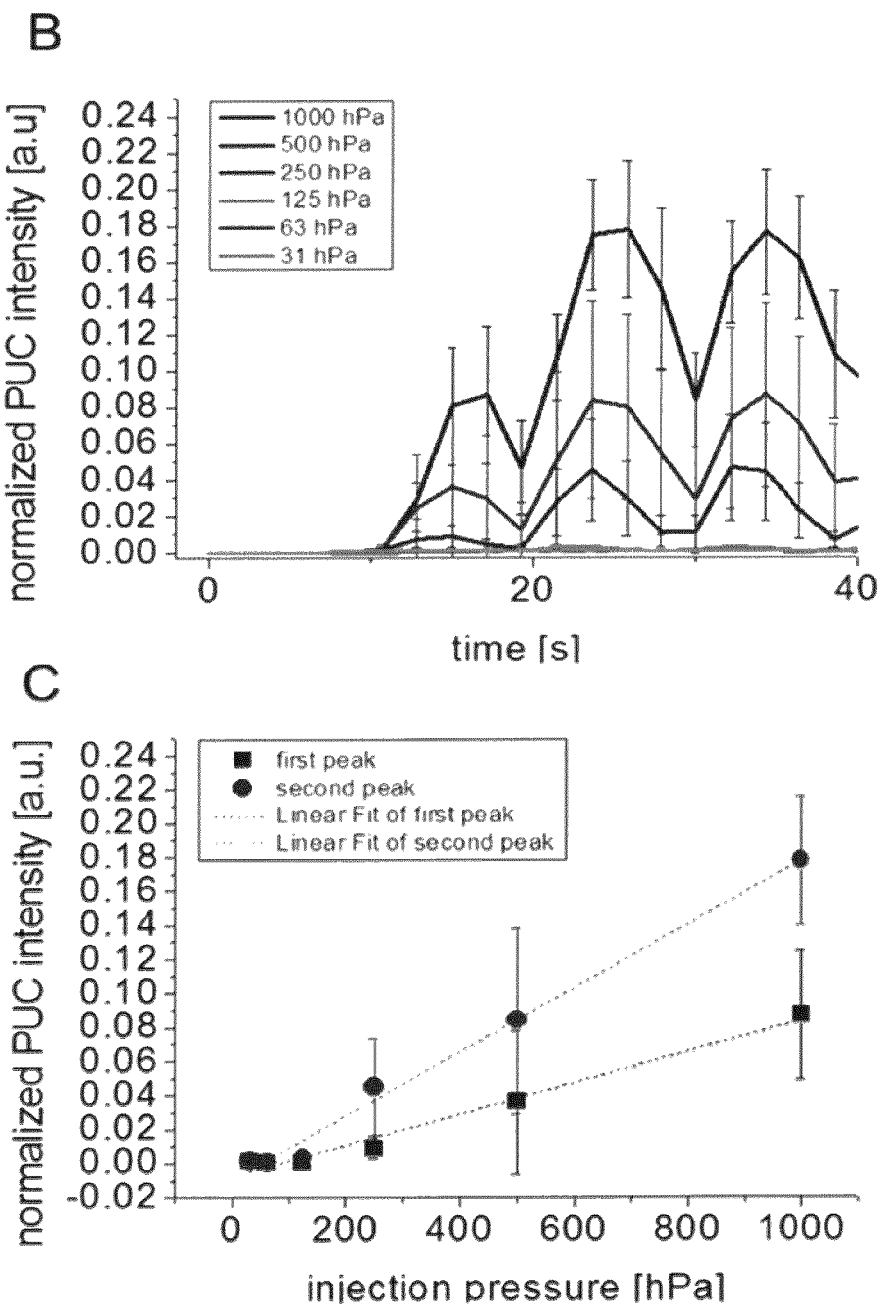
Fig. 13 B-C

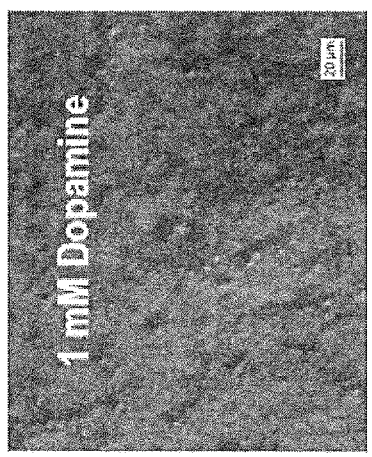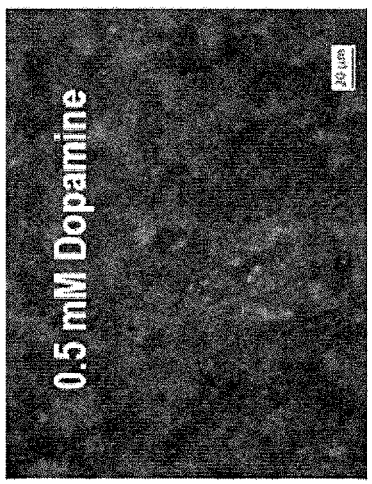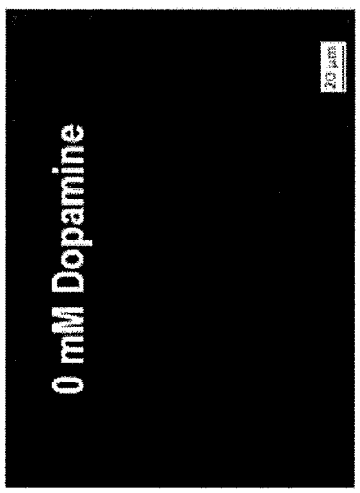
Fig. 14 A-C

E

Fig. 14 E

Fig. 15 A, B, C

A
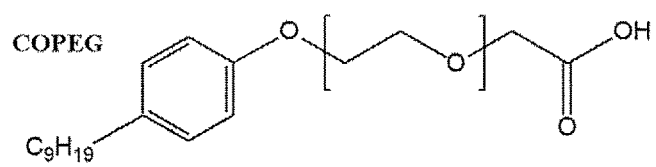
B
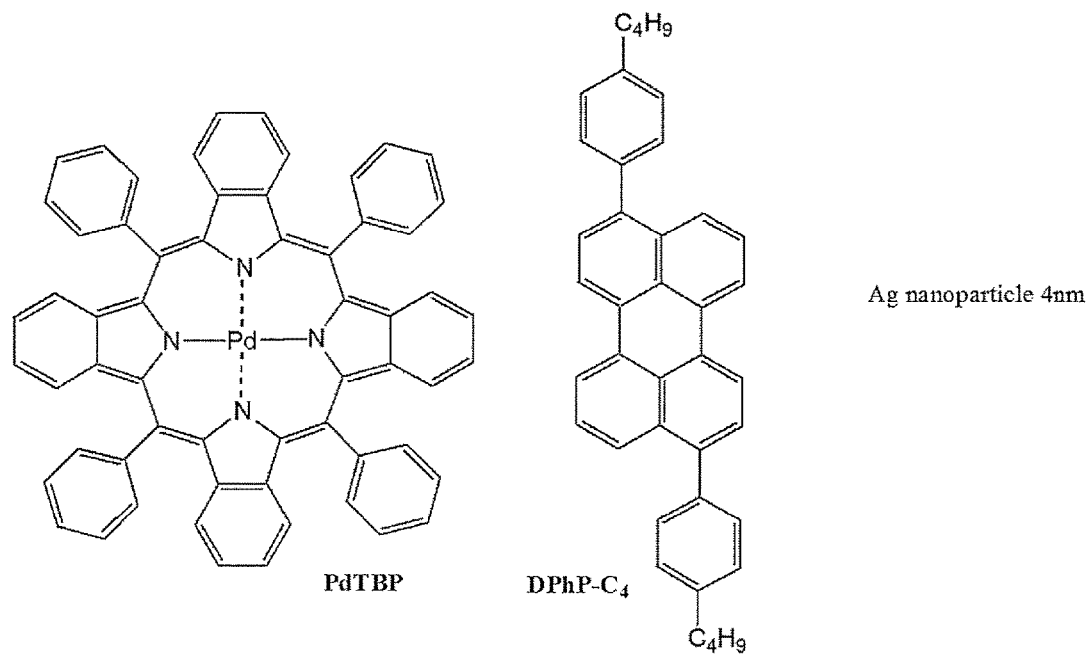
C
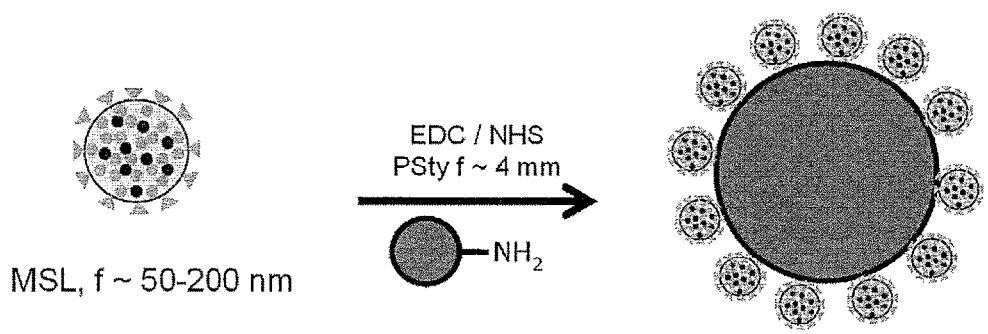
Fig. 17 A-C

POLYMERIC ORGANIC NANOPARTICLES WITH ENHANCED EMISSION

BACKGROUND

The field of the DISCLOSURE is the field of luminescent, fluorescent, phosphorescent and photon up-conversion polymeric organic nanoparticles.

The present disclosure relates to luminescent including photon up-conversion nanoparticles. These nanoparticles include a polymeric organic matrix, at least one light emitter distributed within this matrix, a stabilizing agent, and at least one metal particle enclosed within the matrix, wherein the metal particles are plasmonic nanoparticles. The present disclosure further relates to methods of manufacture and to uses of such nanoparticles.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, as well as aspects described in this background section in relation to nanoparticles, sensors and sensing layers are neither expressly nor implicitly admitted as prior art against the present disclosure.

In recent years, nanoparticles have emerged as important materials with numerous applications ranging from display devices to the use as optical reporters and bioprobes in the life sciences.

Among the organic nanoparticles capable of emitting light, different types of nanoparticles have been developed, such as organic nanoparticles capable of fluorescence emission or capable of phosphorescent emission. Both types are commercially available, especially the fluorescent types. But they mostly have low emission quantum yield and low photostability. They are used for multiple applications so enhancement of the emissive properties is urgently needed. In contrast to the fluorescent and phosphorescent nanoparticles, the existing photon upconversion nanoparticles other than those disclosed in EP 2298849 A1 or US 2010/0330026 A1 are inorganic.

SUMMARY

The present disclosure provides a nanoparticle including
a polymeric organic matrix,
at least one light emitter distributed within said matrix,
a stabilizing agent, and
at least one metal nanoparticle enclosed within said matrix,
wherein said at least one metal nanoparticle is a plasmonic nanoparticle.

The present disclosure provides a sensing layer including nanoparticles according to the present disclosure.

The present disclosure provides a method of producing nanoparticles as defined in any of the embodiments above, said nanoparticles including
a polymeric organic matrix,
at least one light emitter distributed within said matrix,
optionally at least one sensitizer and/or at least one antioxidant distributed within said matrix,
a surface stabilizing agent, and
at least one metal nanoparticle enclosed within said matrix,
wherein said at least one metal nanoparticle is a plasmonic nanoparticle and/or is capable of increasing the photostability of the organic nanoparticle,
said method including the steps of:
providing a polymer or combination of polymers or combination of polymers with small molecules from which the polymeric organic matrix is to be formed, a stabilizing agent, at least one light emitter, plasmonic metal nanoparticles
and optionally at least one sensitizer and/or at least one antioxidant,
preparing a dispersion of said plasmonic metal nanoparticles in an organic water-miscible solvent, optionally allowing ligand exchange of said plasmonic metal nanoparticles,
preparing a mixture of said polymer or said combination of polymers or said combination of polymers and small molecules from which the polymeric organic matrix is to be formed, said surface stabilizing agent, said light emitter(s) and optionally said sensitizer(s) and/or said antioxidant(s) in an organic water-miscible solvent,
adding said mixture of said polymer or said combination of polymers or said combination of polymers and small molecules, said surface stabilizing agent, said light emitter(s) and optionally said sensitizer(s) and/or said antioxidant(s) to said dispersion of plasmonic metal nanoparticles or vice versa, thus forming a mixture including said plasmonic metal nanoparticles,
inducing said mixture including said organic matrix components and surface stabilizer, emitters and plasmonic metal nanoparticles to form nanoparticles, thus forming a dispersion of nanoparticles wherein said nanoparticles include a polymeric organic matrix with said light emitter(s) and, optionally, said sensitizer(s) and/or said antioxidant(s), distributed therein, and wherein said metal nanoparticles are enclosed in said polymeric organic matrix.

The present disclosure also provides the use of nanoparticles according to the present disclosure in a biological application selected from the group consisting of labeling and/or detection of cells, biological (macro-)molecules or other analytes, fluorescence microscopy, (flow) cytometry, fluorescence-activated cell sorting (FACS), fluorescence resonance energy transfer (FRET), immunohistochemistry, clinical immunoassays, fluorescence-quenching-based enzyme-activity assays, high-throughput screening, molecular diagnostics, sensing of temperature, sensing of pressure and sensing of oxygen.

In the present disclosure the detection/sensing of neurotransmitters and other singlet oxygen scavengers are provided. Examples are given of preparation of sensing layers containing the organic nanoparticles for detection (sensing) of neurotransmitters and other singlet oxygen scavengers. The targeted application is using the layers for sensing/imaging of neurotransmitters as released from live cells—functional live cell imaging.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2 shows a characterization of nanoparticles (NPs) as prepared in Example 1. (A) Z-average diameter. (B) Absorption. (C) Emission when excited with 405 nm. (D) Emission when excited with 488 nm. In each case, the zeta potential was −55 mV The chosen batches of NPs (81) illustrate 4 different variations; in two batches, the size of the Ag nanoparticles was varied (batches 81.2 and 81.3), and in two batches, the concentration of the antioxidant lipoic acid used was varied (batches 81.1 and 81.4) The concentration of lipoic acid is higher in batch 81.4, and the same lipoic acid concentration is used in batches 81.2 and 81.3.

FIG. 3 shows the effect of plasmon enhancement by incorporation of 4 nm silver nanoparticles in the photon up-conversion nanoparticle matrix of nanoparticles (NP), with the chromophore in (A) being 3,10-Bis((4-tert-butylphenyl)ethynyl)perylene. These are also the same NPs as shown in FIG. 2 as batch 81.4 (without incorporation of 4 nm Ag NPs) and batch 81.2 (with incorporation of 4 nm Ag NPs). In (B) the standard chromophore coumarin was used as light emitter. As can be seen, the emission decay time of the Coumarin 153 is shortened due to the Ag NP plasmon. The fluorescence signal (not shown) was correspondingly also enhanced by >2x.

FIG. 8 shows:

(A) Jablonski Diagram of the up-conversion mechanism in presence and absence of molecular oxygen. The sensitizer molecule is excited by absorption a photon with hv1. Via intersystem crossing, the triplet state of the sensitizer is predominantly occupied within ns. In the absence of oxygen, triplet-triplet energy transfer takes place between the sensitizer and the emitter molecule. Two emitters in triplet state can now undergo triplet-triplet annihilation leading to one emitter back in ground state and one emitter with an occupied excited singlet state, which can emit anti-Stokes shifted light with energy $hv_2$. In the presence of oxygen, the energy is transferred to molecular oxygen in triplet state producing singlet oxygen.

(B) Schematic drawing of a PUC (photon upconversion) NP (nanoparticle) composition. (C) Characterization of PUC (photon upconversion) NPs (nanoparticles) by QY (quantum yield): QY of PUC in absence of molecular oxygen (anaerobic conditions) as a function of illumination intensity. The QY remains constant for intensity variation between 1 and 10 W/cm2.

(D) The intensity dependence of the PUC emission integral amount for different excitation intensities (anaerobic conditions). In the range 0.4 to 10 W/cm2 excitation a linear dependence is confirmed.

FIG. 9 shows: emission spectra of PUC-NP in aqueous dispersions at different serotonin and dopamine concentrations under 633 nm.

(A) and (B) Emission spectra of PUC-NPs at dopamine concentrations ranging from 1 mM to 20 mM (A) or at serotonin concentrations ranging from 0.1 mM to 1 mM (B), respectively.

Figure 10:
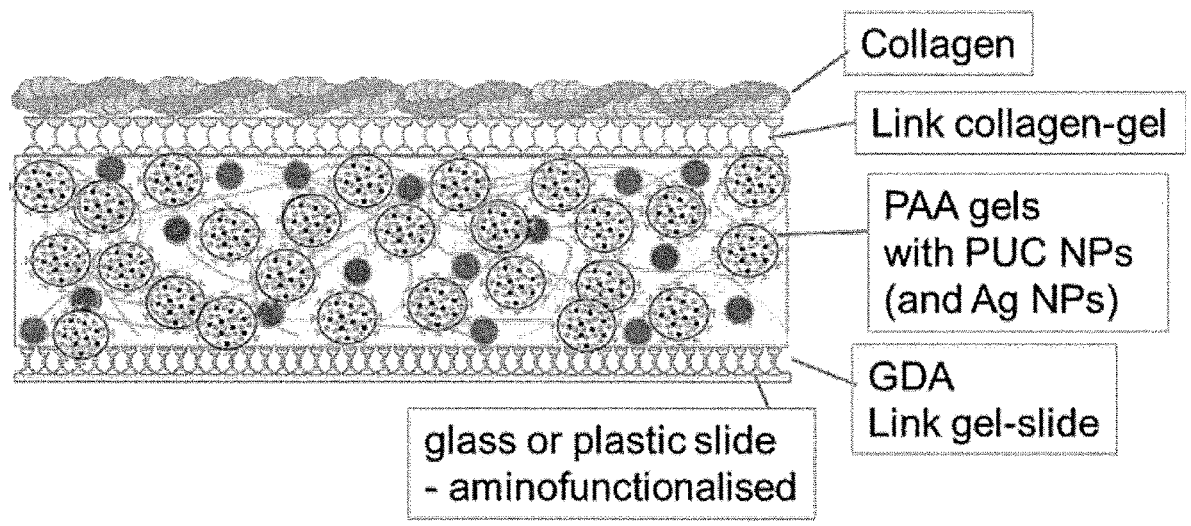

(C) PUC emission and phosphorescence as a function of the dopamine (C) or serotonin (D) concentration. DA=dopamine; ST=serotonin FIG. 10 shows: An embodiment of a sensor including an emissive layer (also sometimes referred to as "sensing layer" or "emissive sensing layer"=ESL) from organic nanoparticles with metal nanoparticles and antioxidant inside, an attachment (link) layer for the cell adhesion layer, a cell adhesion layer (in this case collagen). The same sensors have been used further in the examples. PAA=polyacrylamide; PUC NPs=photon upconversion nanoparticles; Ag NPs=silver nanoparticles; GDA=glutardialdehyde;

FIG. 11 shows:

(A) normalized PUC intensity in dependence of the illumination time with non-coherent light at 638 nm with an intensity of 2.3 $W/cm^2$ at different dopamine concentrations.

(B) normalized PUC intensity as a function of the dopamine concentration at different illumination times.

(C) Images of PUC emissive sensing layer at different concentrations of dopamine after 7.2 s of illumination with non-coherent light at 638 nm with an intensity of 2.3 W/cm2. All images were taken at the same area.

(D) normalized PUC intensity in dependence of the illumination time with non-coherent light at 638 nm with an intensity of 2.3 W/cm$^2$ at different serotonin concentrations.

(E) normalized PUC intensity as a function of the ST concentration at different illumination times.

(F) Images of PUC emissive sensing layer at different concentrations of serotonin after 2.4 s of illumination with non-coherent light at 638 nm with an intensity of 2.3 W/cm$^2$. All images were taken at the same area.

Figure 12:
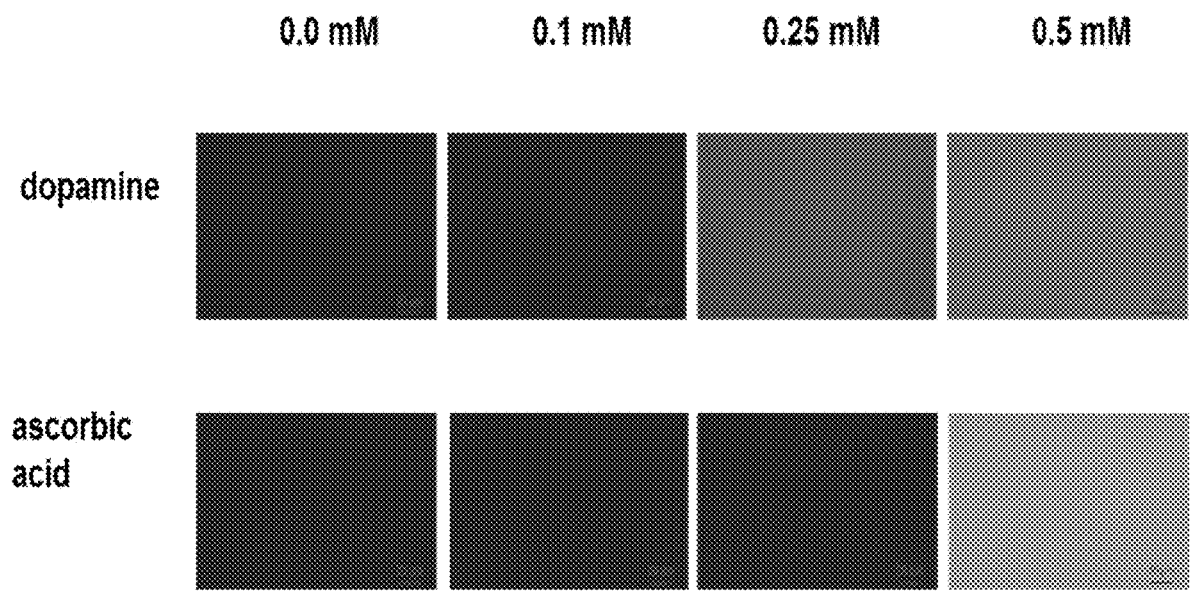
Figure 13:
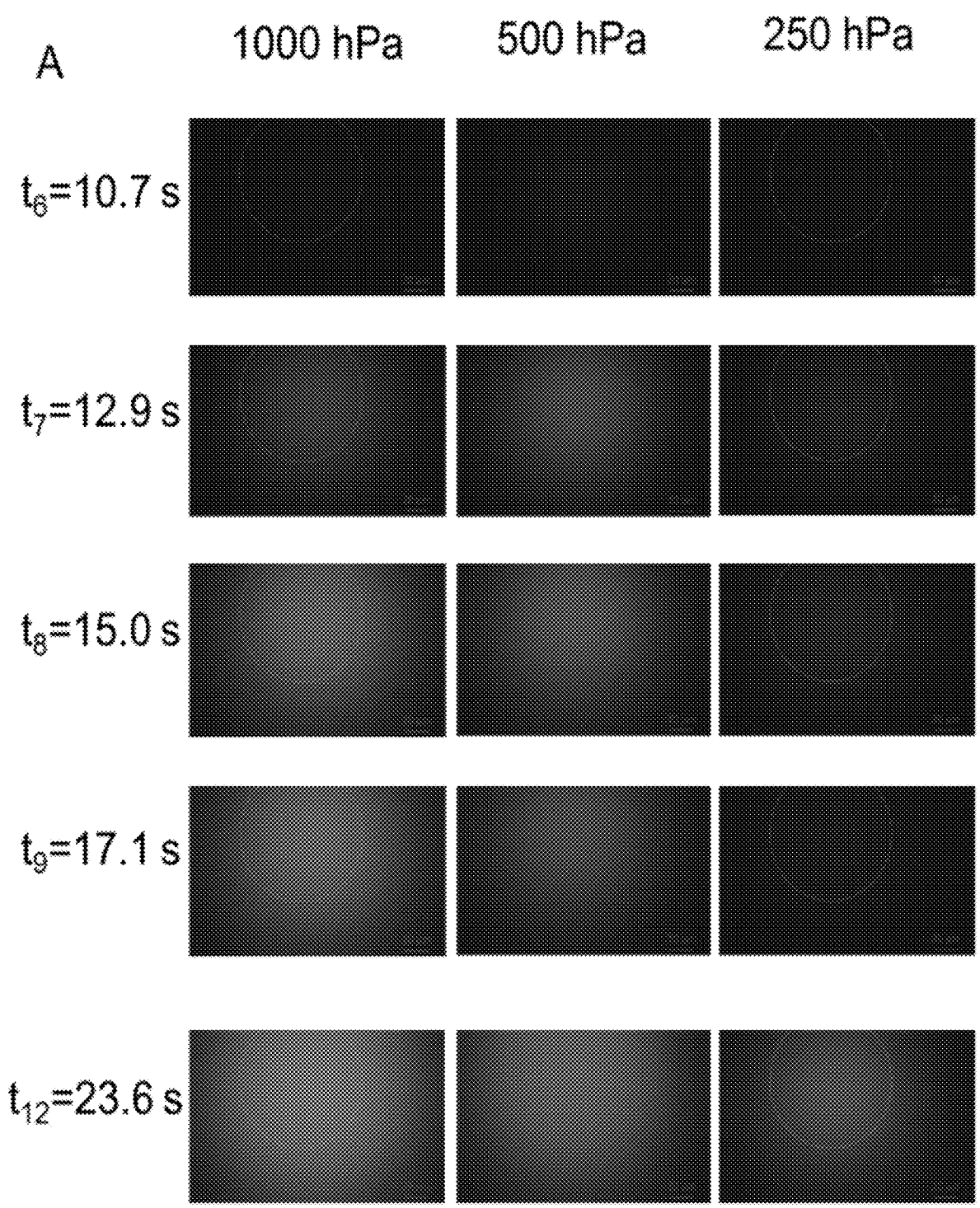

FIG. 12 shows: A comparison between sensing capabilities of emissive sensing layer (ESL) between ascorbic acid and dopamine at concentrations from 0.0 mM to 0.5 mM. Brightness of images was increased by 40%.

FIG. 13 shows:

(A) Visualization of local dopamine release from a micropipette positioned close to the layer surface using ESL under illumination with non-coherent light at 638 nm with an intensity of 2.3 W/cm$^2$. Dopamine was released from the pipette shortly before $t_5$ 10 s after start of the respective time series and then every 10 s. At $t_{12}$=23.6 s the maximum of PUC signal after the second release shortly before $t_{11}$=20 s. Release pressures were varied between 1000 hPa and 31 hPa. Images are represented at a gamma value of 0.45 (scale bar: 20 μm)

(B) normalized PUC intensity (n=3, mean±std) as a function of time after dopamine release from a micropipette. Dopamine solution droplet was first released at 10 s by the micropipette and then every 10 s.

(C) maximum normalized PUC intensity after first and second release of 2 mM dopamine droplet from a micropipette (mean±std) as a function of the release pressure. Data were fitted linearly without weights (dotted line).

Figure 14:
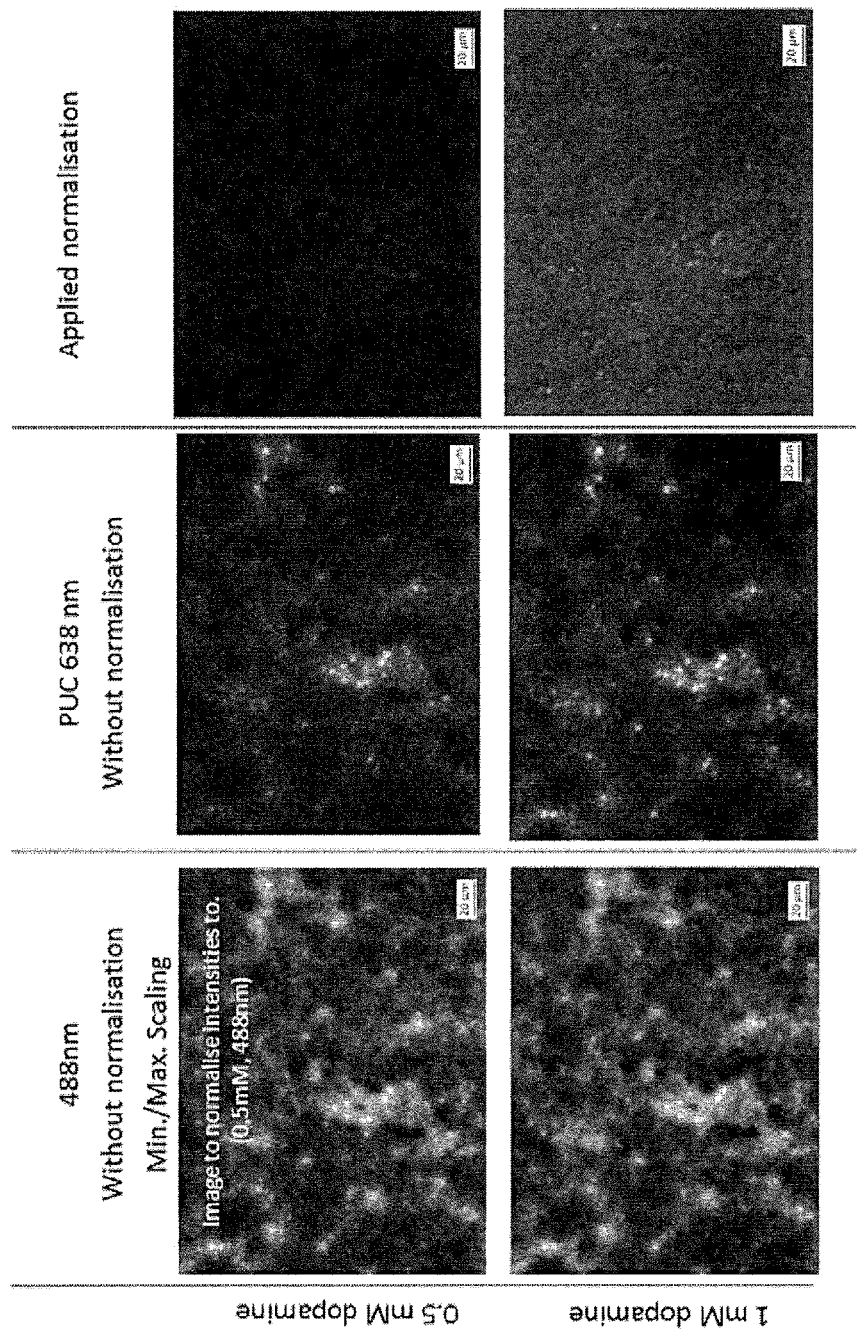

FIG. 14 shows data obtained with a sensor according to the present disclosure for a polymer matrix.

(A) Control image of sensor in the presence of complete growth medium without neurotransmitter (sometimes abbreviated herein also as "NT") imaged in photon up-conversion mode. The medium is on top of the sensor/sensing layer. The control image is completely black.

(B)+(C) Sensor in presence of complete growth medium including 0.5 mM (B) and 1 mM (C) of the neurotransmitter (NT) dopamine, imaged in photon up-conversion mode. The images obtained are clearly brighter than the control image.

Figure 7:
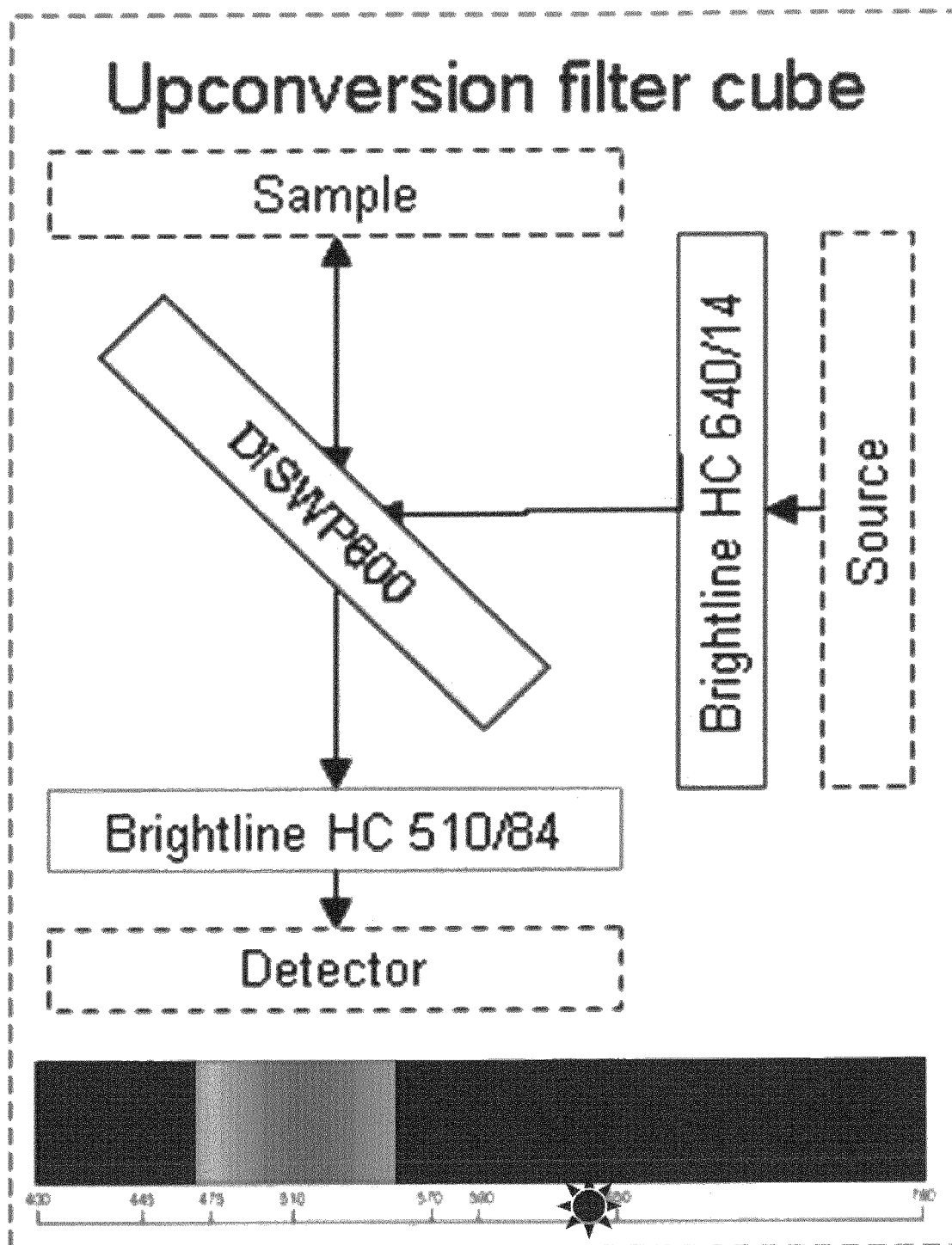
FIG. 7 shows a schematic diagram of the band filter cube(s) for photon up conversion imaging and microscopic images obtained by live cell imaging of HepG2 cells after uptake of nanoparticles according to the present disclosure. (A) shows band filter cubes used for photon up-conversion imaging: Excitation with band filter centered at 640 nm with 14 nm transmission band. The upconversion emission is detected through band filter center at 520 nm with 84 nm transmission band. (B) Standard fluorescence mode with excitation at 405 nm. (C) Standard fluorescence mode with excitation at 488 nm. (D) Unique up-conversion imaging with excitation at ca. 630 nm and emission at 450-520 nm. No autofluorescence.

The images shown in (A), (B) and (C) are photon up-conversion (PUC) images taken with an excitation of 640 nm (band filter centered at 640 nm with 14 nm transmission band). The up-conversion emission is detected through a band filter centered at 520 nm with 84 nm transmission band (for the microscope cube see FIG. 7A). Standard imaging duration was 2 s. After each PUC image, a fluorescence image with 488 nm excitation for 100 ms (control or image for normalization) was taken.

FIGS. 14(B) and (C) shows data obtained with a sensor according to the present disclosure adapted to the detection of dopamine in an experiment (C) in the presence of 0.5 mM dopamine (B), and in the presence of 1 mM dopamine (C). The medium is on top of the sensor/sensing layer. Then, 0.5 mM and 1 mM (final concentration) of the neurotransmitter dopamine was pipetted on the layer into the complete growth medium. All images are Photon up-conversion (PUC) images (excitation 638 nm). Standard imaging duration was 2 s. After each PUC image, a fluorescence image with 488 nm excitation for 100 ms (control or image for normalization) was taken. The control image obtained in the absence of dopamine is completely black (data shown in 14A), the images obtained in the presence of 0.5 mM dopamine are clearly brighter than the control image obtained in the absence of dopamine, whereas the images obtained in the presence of 1 mM dopamine are again much brighter than the image obtained in the presence of 0.5 mM dopamine.

(D) shows the normalization of a photon up-conversion image (633 nm) to a fluorescence image (488 nm) leading to improvement of sensing quality for both, 0.5 mM and 1 mM dopamine. The normalized images confirmed a resolution higher than 10 μm density. The normalized image obtained in the presence of 1 mM dopamine had the expected increase in brightness compared to the normalized image obtained in the presence of 0.5 mM dopamine.

(E) shows the successful imaging of dopamine at a concentration as low as 0.1 mM with a sensor according to the present disclosure (same procedure as described above). The image obtained in the presence of 0.1 mM dopamine is clearly brighter than the image obtained in the absence of dopamine.

Figure 15:
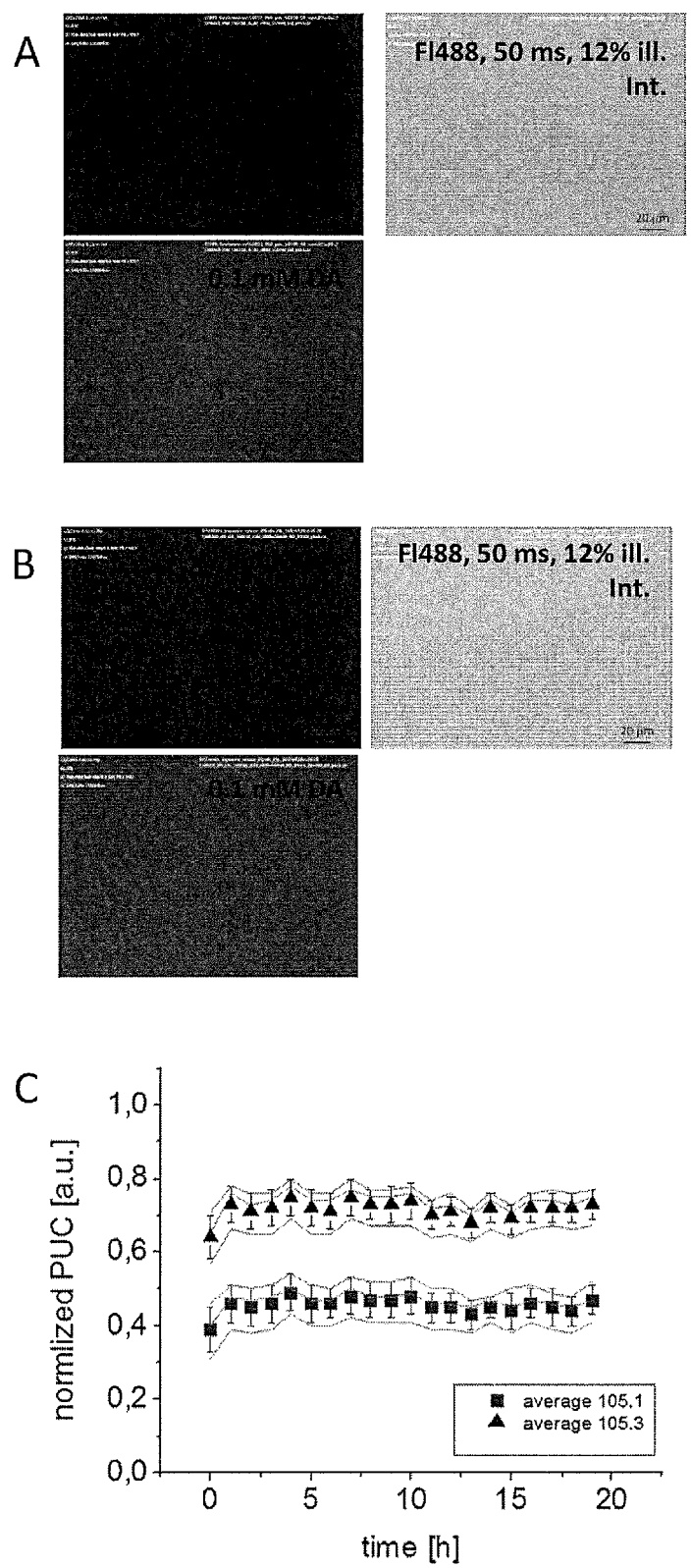

FIG. 15 shows data obtained from an experiment to examine layer stability of sensing layers as included in the sensor according to the present disclosure. For the figures shown in A and B the ESL as shown in C with NPs with higher sensitizer concentration were used. FIG. 15A: Left: Photon upconversion signal of an ESL directly after preparation. The dark image is taken with HBSS without dopamine (DA) and below it is the image with 0.1 mM dopamine (DA) in the HBSS incubated with 0.0 mM dopamine (DA) and 0.1 mM (DA) in HBSS. Right: corresponding fluorescence imaged at 488 nm illumination. FIG. 15B: Left: Photon upconversion signal of an ESL after 15 days at 37° C. and 5% $CO_2$ with CDI iCell DopaNeuron cells growing on the layers. The dark image is HBSS without dopamine (DA) and below it with 0.1 mM dopamine (DA) in the HBSS. Right: corresponding fluorescence imaged at 488 nm illumination. FIG. 15C: Changes of the normalized PUC signal (under nitrogen 95% and CO2 5% atmosphere at 37° C.) over 24 h. The PUC NPs batches 105.1 and 105:3 contain different amount of sensitizer PdTBP.

Figure 16:
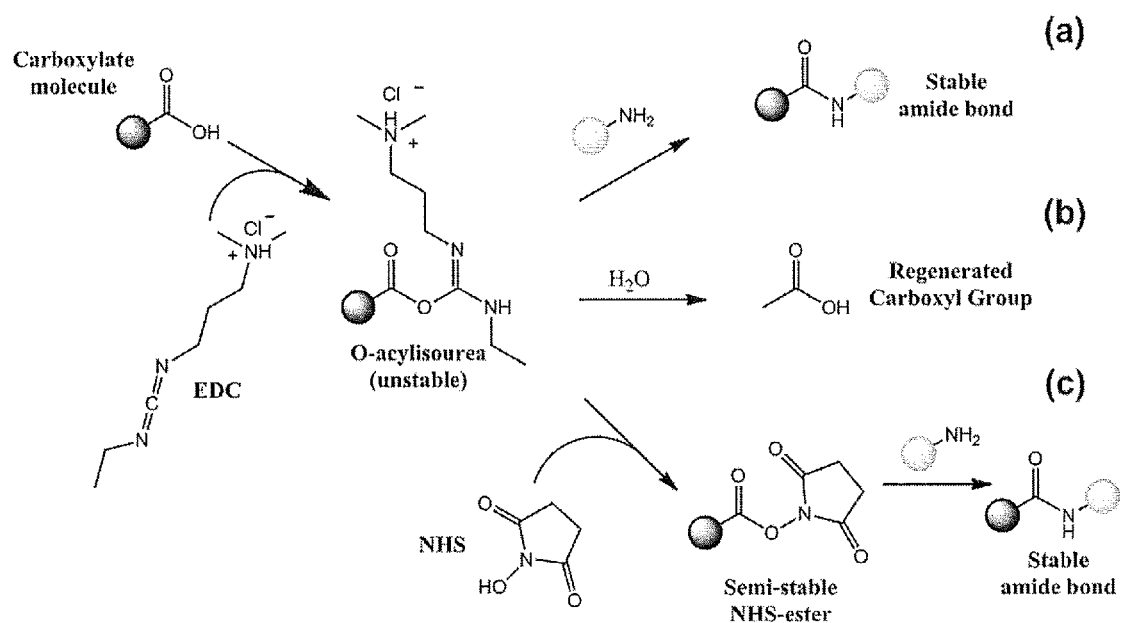

FIG. 16 shows the mechanism of crosslinking of carboxylic acid groups to a primary amine, forming an amide bond, by using the crosslinking agents 1-Ethyl-3-[3-dimethylaminopropyl]carbodiimide Hydrochloride (EDC) and N-hydroxysuccinimide (NHS). This reaction can be used for the attachment of the NPs when they have COOH on their surface to any NH2 (amino) group containing surface or molecule. The same reaction can be used for the formation of cross-linked gels of e.g. collagen with NPs (chemically crosslinked gels).

Figure 6:
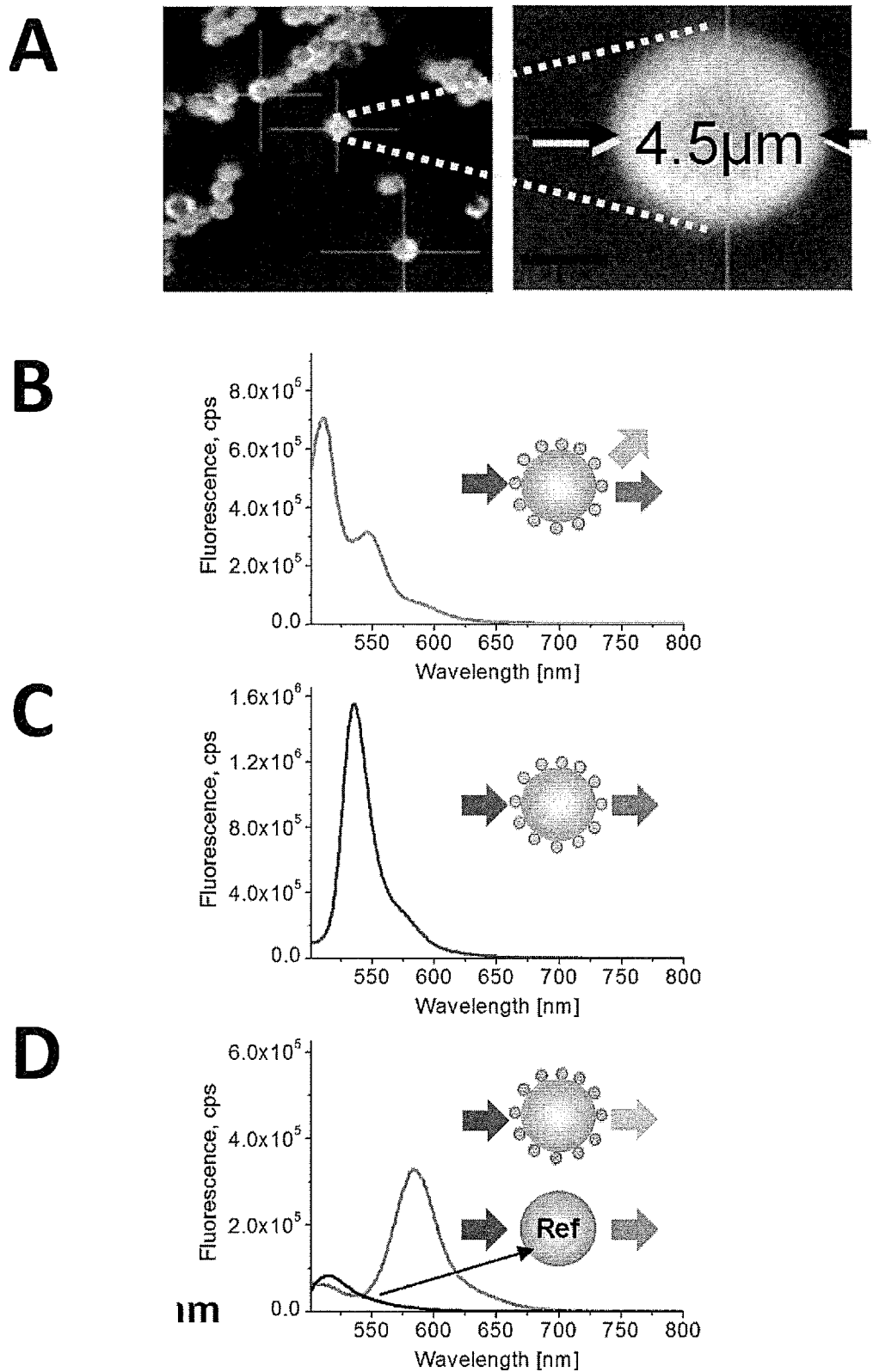
FIG. 6 shows confocal microscopy data (A) and spectroscopic data (B-D) obtained with nanoparticles according to the present disclosure conjugated to microparticles as cell models. For details on the conjugation reaction of the nanoparticles to microparticles, see also FIGS. 16 and 17. For (B) Absorbance: 488 nm, Emission: 514 nm and 555 nm, HWHM (half-width at half-maximum) at 514 nm: 15 nm, HWHM at 555 nm: 18 nm; (C) Absorbance: 488 nm, Emission: 535 nm, HWHM: 14 nm; (D) Absorbance: 488 nm, Emission: 590 nm, HWHM: 21 nm; Reference FITC HWHM: 30 nm.

FIG. 17 shows components of the (TTA-UC)-NP (triplet-triplet annihilation supported upconversion). (A) Glycolic acid ethoxylate 4-nonylphenyl ether (CoPEG) can be used as surface stabilizing agent at the surface. As component of the matrix (the inner side of the NP) phenylheptadecane, Polymethylmetacrylate (PMMA) as polymer and Ascorbic acid palmitate palmitate as singlet oxygen scavenger may be used. (B) Also in the inner part of the nanoparticle, PdTBP may be used as sensitizer, DPhP-$C_4$ as emitter, and 4 nm Ag particles can be used as plasmonic nanoparticles. (C) Illustrates the process of attachment of the organic nanoparticles on the surface of an object (e.g. protein, a microparticle, a cell or any other surface with present suitable functional groups, e.g. aminogroups). This shows the possibility of labelling using the organic NPs in accordance with the present disclosure. In FIG. 6 the labeled microparticles (size 4.5 μm) are shown in fluorescence confocal microscopy images.

Figure 18:
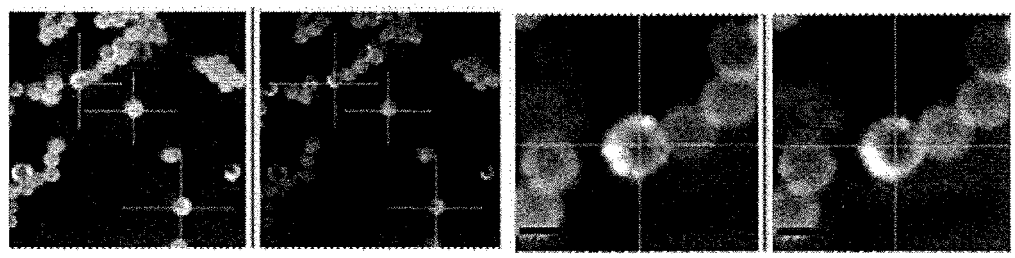

FIG. 18 shows the characterization of the crosslinked nanoparticle-microparticle conjugate purified by filtration. Confocal microscopy pictures. (a) area 70 μm×70 μm; (b) area 20 μm×20 μm; (c) area 10 μm×10 μm; (d) area 10 μm×10 μm.

Figure 19:
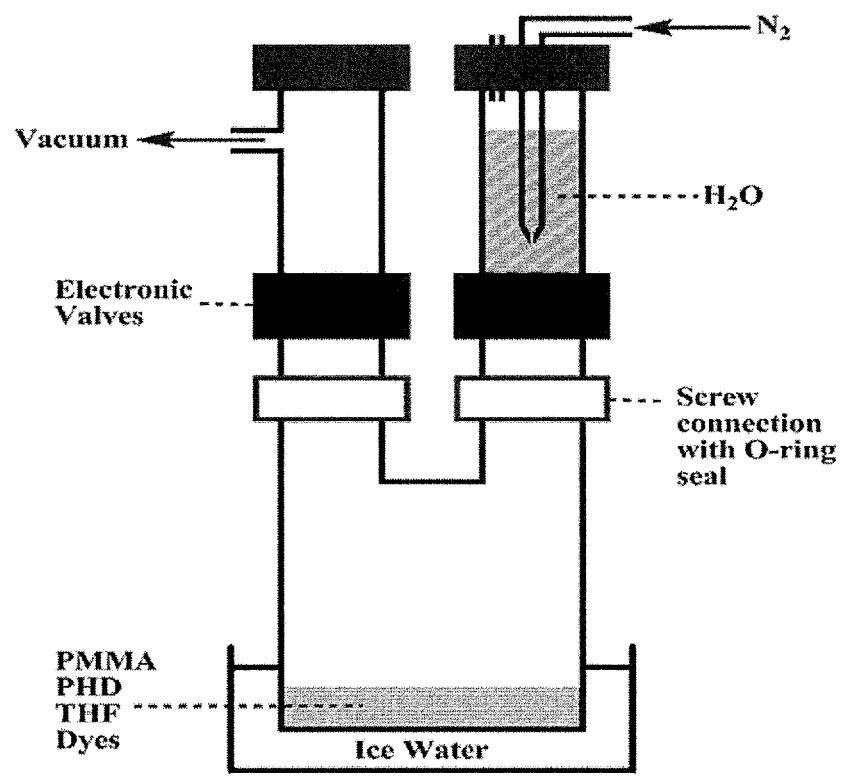

FIG. 19 shows an example of a nanoparticle fabrication chamber with valves.

DETAILED DESCRIPTION OF THE EMBODIMENTS

The following embodiments can, wherever this does not lead to logical contradictions, be combined with each other without restrictions. Thus, the present disclosure shall encompass, even where not explicitly spelled out in the following, any feasible combination of the embodiments described below.

As discussed above, the present disclosure provides a nanoparticle (NP) including
a polymeric organic matrix,
at least one light emitter distributed within said matrix,
a surface stabilizing agent, and
at least one metal nanoparticle enclosed within said matrix,
antioxidant, in particular a singlet oxygen scavenger, a reactive oxygen scavenger (ROS) scavenger or a radical scavenger.

It has been found that said at least one metal nanoparticle is capable of enhancing the intensity of the light emitted by said light emitter(s) by way of plasmon enhancement. It has also been found that the shape and the reactivity of the NPs when used in crosslinking/attachment to amino group containing surfaces or molecules is stabilized. It has furthermore been found that the presence of said metal nanoparticle in said nanoparticle (NP) enhances the photostability of such NP.

In one embodiment, said polymeric organic matrix is a solid matrix. As the skilled person will appreciate, said polymeric organic matrix is chemically inert with respect to the other components of the nanoparticle or the surroundings/milieu in which said nanoparticle is used. As the skilled person will appreciate, the polymeric organic matrix is optically inert (i.e. it does not affect the light used to excite the light emitter(s) or the light that is emitted by the light emitter(s)). In one embodiment, said polymeric organic matrix is transparent in the range of from 300 to 1600 nm.

In one embodiment, said polymeric organic matrix is composed of a material selected from the group consisting of polyacrylonitriles, polystyrenes, styrene copolymers, styrene-butadiene copolymers, polystyrene-based elastomers, polyethylenes and oligoethylenes, polypropylenes, polytetrafluoroethylenes, extended polytetrafluoroethylenes, polyacrylates, polymethylmethacrylates, ethylene-co-vinyl acetates, polysiloxanes, such as polymethylsiloxanes and polyphenylmethylsiloxanes, e.g. polydimethylsiloxane or polyphenylmethylsiloxane, their copolymers as well as substituted and modified polysiloxanes, polyethers, polyurethanes, polyether-urethanes, polyethylene terephthalates and polysulphones, particularly a material selected from the group consising of polystyrenes, polyacrylonitriles and polymethylmethacrylates, more particularly polymethylmethacrylate.

In one embodiment, said nanoparticle (NP) has a diameter in the range of from 10 to 1000 nm, particularly in the range of from 10 to 500 nm, more particularly in the range of from 10 to 200 nm, even more particularly in the range of from 10 to 100 nm.

In one embodiment, said at least one light emitter is distributed homogeneously within said polymeric organic matrix.

In one embodiment, said at least one light emitter is an organic molecule. In one embodiment, said at least one light emitter consists of one molecule (i.e. only one molecular species). In one embodiment, said at least one light emitter consists of a combination of more than one, in particular two, molecules.

In one embodiment, the light emitted by said at least one light emitter has a wavelength in the range of from 360 to 800 nm, particularly in the range of from 400 to 700 nm.

In one embodiment, said at least one light emitter is capable of emitting light by luminescence, in particular by fluorescence or by phosphorescence, more particularly by fluorescence. In particular said fluorescence is with high quantum yield when the emitter is in the nanoparticle. In one embodiment, said at least one light emitter is a fluorescent or phosphorescent emitter, in particular a fluorescent emitter. In nanoparticles that include both light emitter(s) and a sensitizer(s), the sensitizer molecule(s) are phosphorescent emitters can have highly populated excited triplet state (via strong intersystem crossing singlet-triplet). This triplet state can be emissive (phosphorescence) or not. This depends on the molecular structure.

In one embodiment, said at least one light emitter has a high quantum yield (in the NP matrix) of fluorescence when the light emitter is present within the nanoparticle. In one embodiment, said at least one light emitter is present in said nanoparticle at a high concentration. A relatively high emitter concentration in the confined nanoparticle has the advantage that a high photon outcome with high quantum yield is achieved. This is achieved via optimization of the molecular structure of the emitter and/or via adjustment of the matrix. As used herein, a "high quantum yield" refers to a quantum yield >60%.

In one embodiment, said at least one light emitter is a fluorescence chromophore (in particular having an emissive singlet state). In one embodiment, said at least one light emitter is a phosphorescent chromophore. In one embodiment, said at least one light emitter has a highly populated excited triplet state.

In one embodiment, the light emitted by said at least one light emitter has a wavelength in the range of from 360 to 850 nm, particularly in the range of from 420 to 700 nm. In one embodiment the excitation wavelength of said at least one light emitter is in the range of from 350 to 840 nm, particularly in the range of from 390 to 810 nm.

In one embodiment, said nanoparticle further includes at least one sensitizer. As the skilled person will appreciate, the presence of a sensitizer is obligatory for photon up-conversion (PUC) nanoparticles.

In one embodiment, said at least one sensitizer and said at least one light emitter are separate entities (i.e. the at least one sensitizer and the at least one light emitter are not covalently linked to each other and do not form part of the same molecule).

In one embodiment, said at least one sensitizer is distributed, in particular homogeneously, within said polymeric organic matrix.

In one embodiment, said at least one sensitizer is an organic molecule. In one embodiment, said at least one sensitizer consists of one molecule (i.e. only one molecular species). In one embodiment, said at least one sensitizer consists of a combination of more than one, particularly two, molecules.

In one embodiment, the light emitted by said at least one light emitter has a wavelength in the range of from 360 to 750 nm, particularly in the range of from 420 to 640 nm.

In one embodiment, said at least one sensitizer absorbs light at a wavelength in the range of from 450 to 1600 nm, in particular in the range of from 530 to 860 nm, more particularly in the range of from 620 to 750 nm.

In one embodiment, said at least one sensitizer is capable of absorbing light at a first wavelength region $w \leq \lambda_1 \leq x$, and said at least one light emitter is capable of emitting light at a second wavelength region $y \leq \lambda_2 \leq z$, wherein $\lambda_2 \leq \lambda_1$, wherein, upon absorption of light by said at least one sensitizer at said first wavelength region $w \leq \lambda_1 \leq x$, said at least one light emitter emits light at said second wavelength region $y \leq \lambda_2 \leq z$.

In one embodiment, said light emitted by said light emitter at said second wavelength region $\lambda_2$ is due to an up-conversion process based on triplet-triplet transfer (sensitizer triplet to emitter triplet) followed by triplet-triplet annihilation of the emitter triplets. Particularly, the up-conversion process occurs upon absorption of light by said sensitizer at said first wavelength region $\lambda_1$, or said light emitted by said light emitter at said second wavelength region) $\lambda_2$ is due to an up-conversion process based on a triplet-triplet transfer process between photoexcited molecules (in triplet state) of said sensitizer molecules to the triplet state of the emitter molecules followed by triplet-triplet annihilation process between photo-excited molecules of said emitter.

In a preferred embodiment, said second wavelength region $\lambda_2$ is in the range 360-750 nm and said first wavelength region $\lambda_1$ is in the range 450-1600 nm.

In one embodiment said light emitter is an organic dye molecule.

In one embodiment, said sensitizer is an organic dye or molecule having a populated triplet or mixed triplet-singlet state, a two-photon-absorbing (TPA)-dye, an optical limiting compound, another molecule with a populated triplet state or an optical limiting compound—e.g. a fullerene, or carbon nanotubes.

In one embodiment, said nanoparticle is capable of photon up-conversion.

In one embodiment, said light emitter in combination with said sensitizer is capable of, upon irradiation with light of appropriate wavelength, photon up-conversion emission (i.e. emission of light generated by photon up-conversion).

In one embodiment, said light emitter is capable of emitting light by luminescence, particularly by fluorescence. Particularly the fluorescence is with high quantum yield and/or high photon outcome when the emitter is in the nanoparticle.

In one embodiment, said at least one light emitter is a fluorescent chromophore.

In one embodiment, said at least one light emitter in combination with said at least one sensitizer is capable of, upon irradiation with light of appropriate wavelength (the excitation wavelength for photon up-conversion), photon up-conversion emission (i.e. emission of light generated by photon up-conversion).

In one embodiment, the energy levels of the triplet state of said at least one light emitter and of the triplet state of said at least one sensitizer are such that they allow for efficient triplet-triplet excitation transfer from the light sensitizer to the light emitter.

In one embodiment, said at least one light emitter is a molecule selected from the group consisting of anthracenes, perylenes, perylene derivatives such as perylene monoimides or perylene diimides, coumarins and BODIPY dyes. In particular, said at least one light emitter is a perylene, a substituted perylene or a perylene derivative, such as perylene monoimide or perylene diimide. A "substituted perylene" or a "perylene derivative" as used herein, refers to a structure having a perylene core. A "perylene derivative" may be a perylene that is substituted with appropriate substituents.

In one embodiment, said at least one light emitter has the structure represented by Formula (I) or (II) or includes a molecule having the structure represented by Formula (I) or (II):

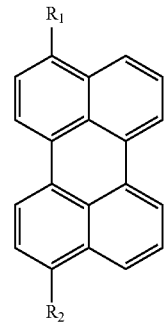

Formula (I)

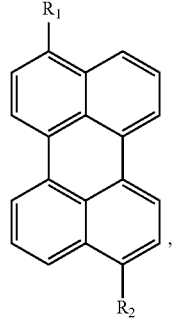

Formula (II)

wherein $R_1$ and $R_2$ are independently selected from the group consisting of hydrogen and a moiety with the structure represented by Formula (III), wherein at least one of $R_1$ and $R_2$ is a moiety with the structure represented by Formula (III):

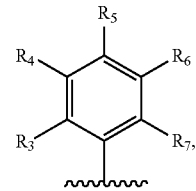

Formula (III)

wherein $R_3$, $R_4$, $R_5$, $R_6$ and $R_7$ are independently selected from the group consisting of H, F, and tri-fluoro-methyl (—$CF_3$), wherein at least one of $R_3$, $R_4$, $R_5$, $R_6$ and $R_7$ is F or tri-fluoro-methyl (—$CF_3$).

In one embodiment, $R_1$ and/or $R_2$ is the moiety represented by Formula (IV):

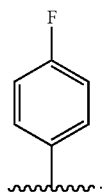

Formula (IV)

In one embodiment, $R_1$ and/or $R_2$ is the moiety represented by Formula (V):

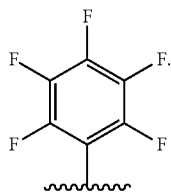

Formula (V)

In one embodiment, $R_1$ and/or $R_2$ is the moiety represented by Formula (VI):

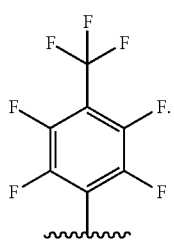

Formula (VI)

In one embodiment, said at least one light emitter has the structure represented by Formula (VII) or includes a molecule having the structure represented by Formula (VII):

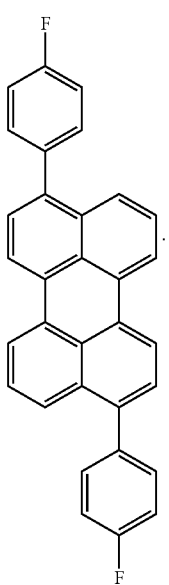

Formula (VII)

In another embodiment, said at least one light emitter has the structure represented by Formula (VIII) or includes a molecule having the structure represented by Formula (VIII):

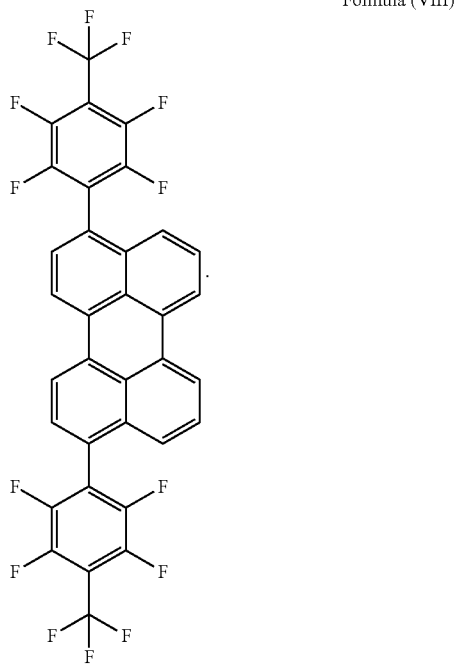

Formula (VIII)

In another embodiment, said at least one light emitter has the structure represented by Formula (IX) or includes a molecule having the structure represented by Formula (IX):

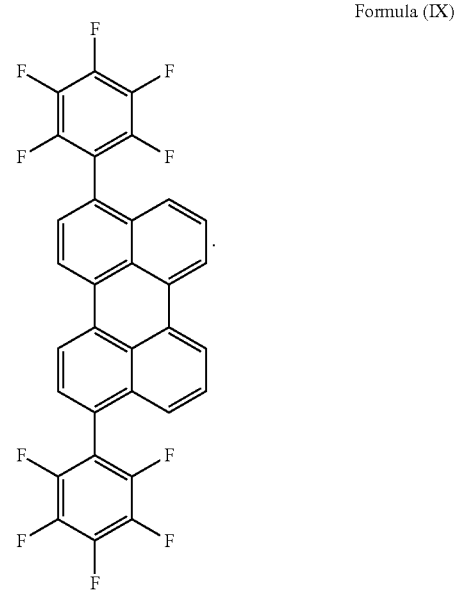 [SMILES: Fc1c(F)c(F)c(-c2ccc3c4ccc(-c5c(F)c(F)c(F)c(F)c5F)c5cccc(c6cccc2c63)c54)c(F)c1F]

Formula (IX)

In one embodiment, said at least one light emitter has the structure represented by Formula (X) or includes a molecule having the structure represented by Formula (X):

Formula (X)

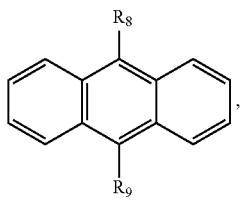

wherein $R_8$ and $R_9$ are independently selected from the group consisting of hydrogen and a moiety with the structure represented by Formula (XI), wherein at least one of $R_8$ and $R_9$ is a moiety with the structure represented by Formula (XI):

Formula (XI)

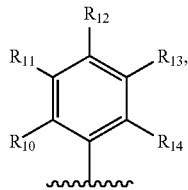

wherein $R_{10}$, $R_{11}$, $R_{12}$, $R_{13}$ and $R_{14}$ are independently selected from the group consisting of H, F, and tri-fluoro-methyl (—$CF_3$), wherein at least one of $R_{10}$, $R_{11}$, $R_{12}$, $R_{13}$ and $R_{14}$ is F or tri-fluoro-methyl (—$CF_3$).

In one embodiment, $R_8$ and/or $R_9$ is the moiety represented by Formula (XII):

Formula (XII)

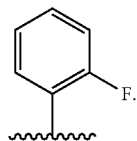

In one embodiment, $R_8$ and/or $R_9$ is the moiety represented by Formula (XIII):

Formula (XIII)

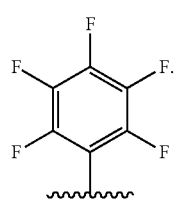

In one embodiment, $R_8$ and/or $R_9$ is the moiety represented by Formula (XIV):

Formula (XIV)

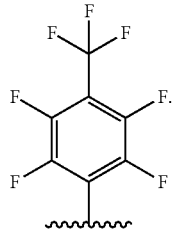

In one embodiment, $R_8$ and/or $R_9$ is the moiety represented by Formula (XV):

Formula (XV)

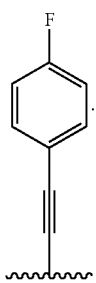

In one embodiment, $R_8$ and/or $R_9$ is the moiety represented by Formula (XVI):

Formula (XVI)

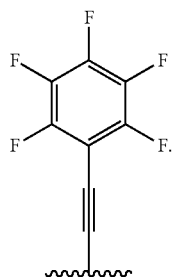

In one embodiment, said at least one light emitter has the structure represented by Formula (XVII) or includes a molecule having the structure represented by Formula (XVII):

Formula (XVII)

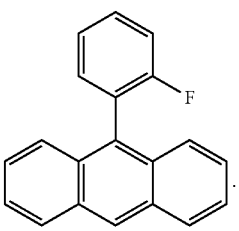

In another embodiment, said at least one light emitter has the structure represented by Formula (XVIII) or includes a molecule having the structure represented by Formula (XVIII):

Formula (XVIII)

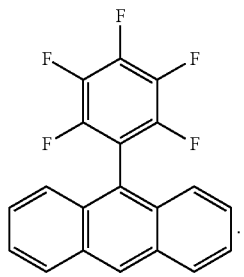

In another embodiment, said at least one light emitter has the structure represented by Formula (XIX) or includes a molecule having the structure represented by Formula (XIX):

Formula (XIX)

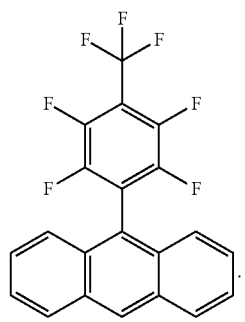

In another embodiment, said at least one light emitter has the structure represented by formula (XX) or includes a molecule having the structure represented by Formula (XX):

Formula (XX)

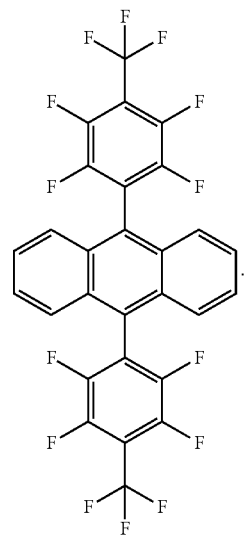

In preferred embodiment, said at least one light emitter has the structure represented by Formula (XXI) or includes a molecule having the structure represented by Formula (XXI):

Formula (XXI)

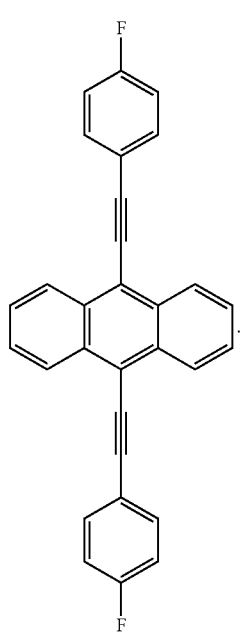

In another embodiment, said at least one light emitter has the structure represented by Formula (XXII) or includes a molecule having the structure represented by Formula (XXII):

Formula (XXII)

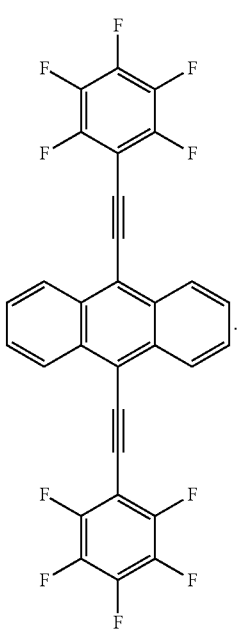

In one embodiment, said at least one light emitter has a structure represented by one of the following structures or includes a molecule having a structure represented by one of the following structures:

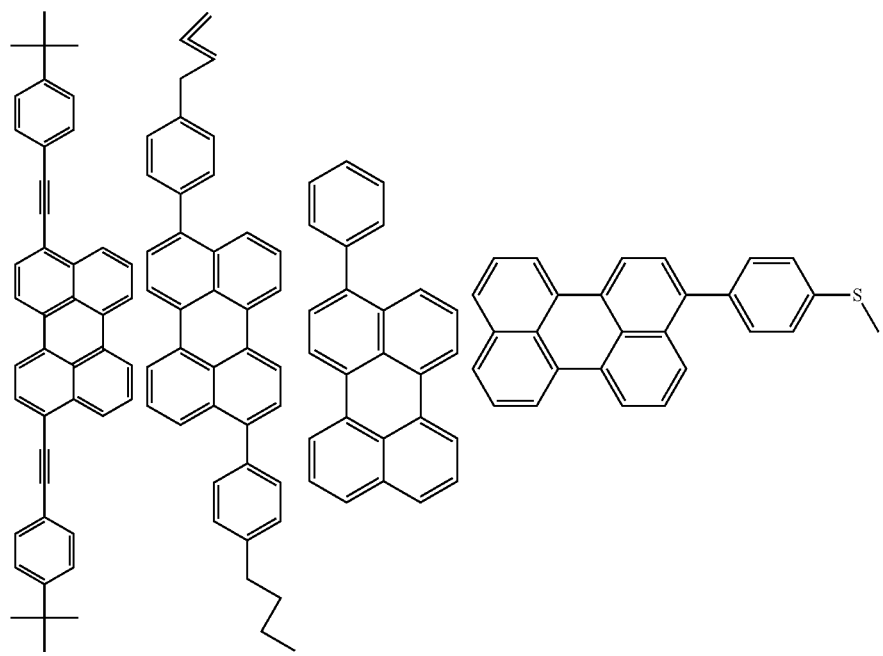
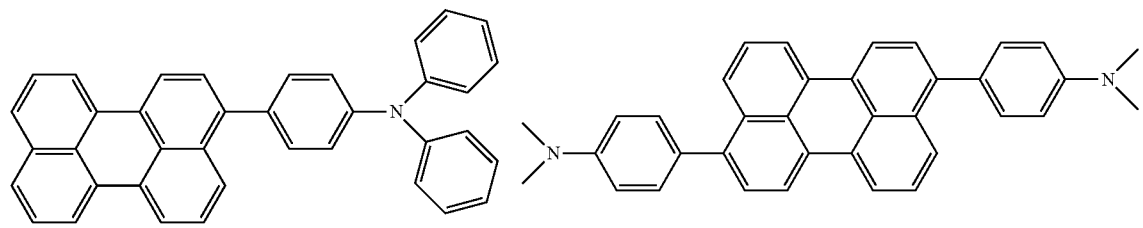
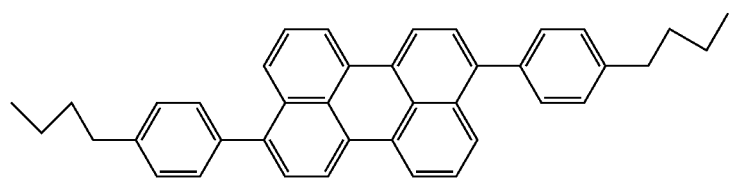
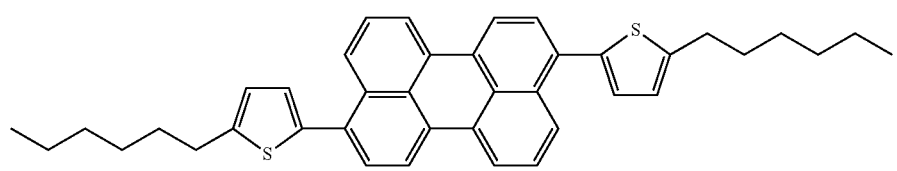

In one embodiment, said at least one light emitter has the structure represented by Formula (XXIII), (XXIV) or (XXV) or includes a molecule having the structure represented by Formula (XXIII), (XXIV) or (XXV):

Formula (XXIII)

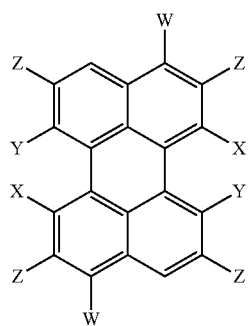

Formula (XXIV)

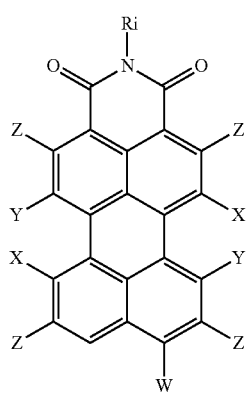

Formula (XXV)

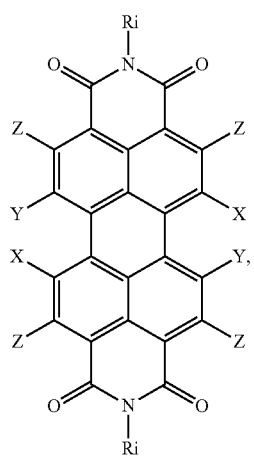

wherein W in formulae XXIII-XXV is selected from one of the following groups:

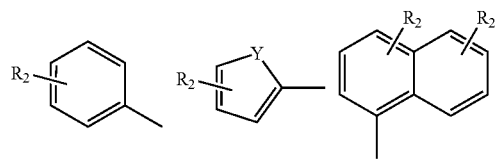

wherein Y, as used in the formulae of W, is selected from the group consisting of $CH_2$, S, O, Se and N—$R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, in particular, $R_2$ has not more than 6 carbon atoms, wherein X and Y in formulae XXIII-XXV are independently selected from the following groups:

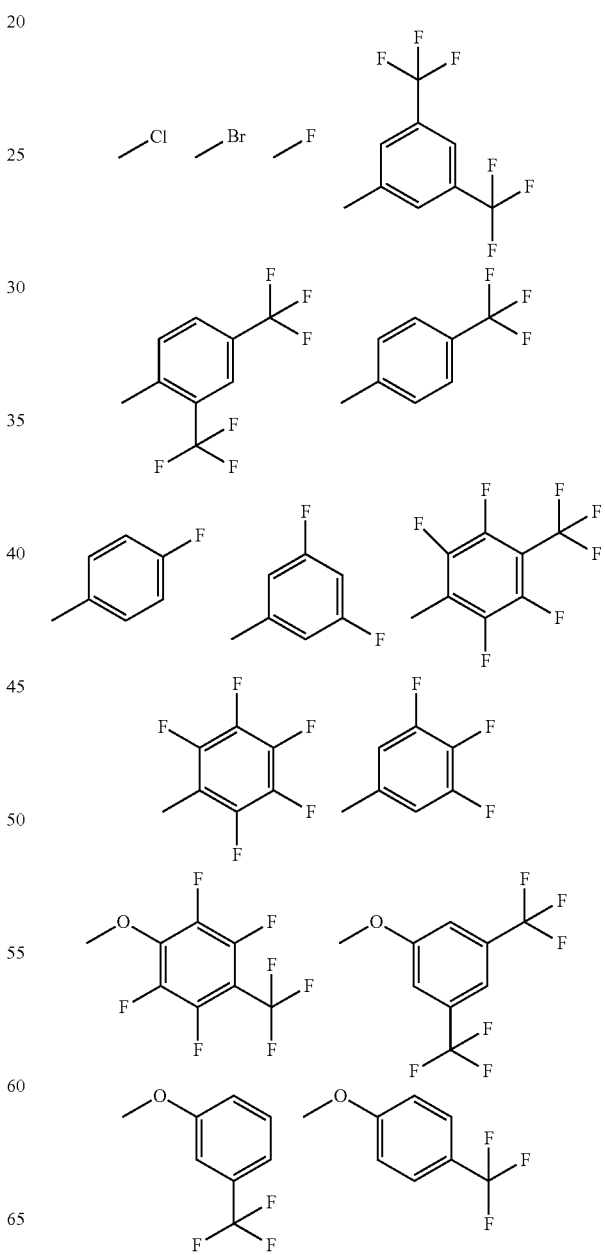

-continued

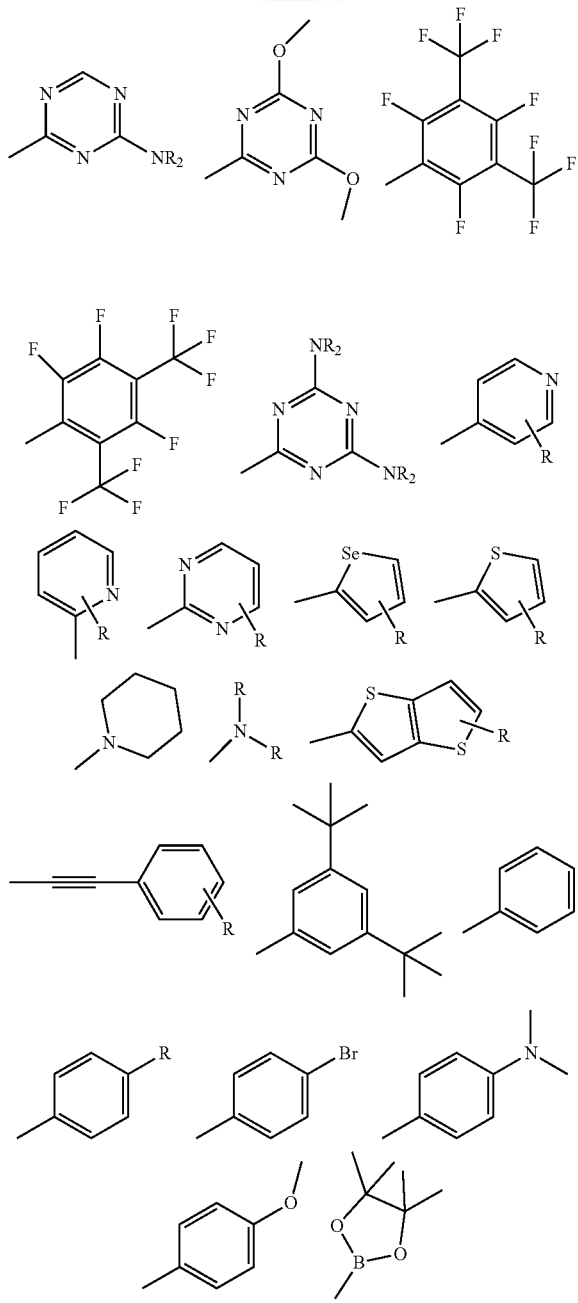

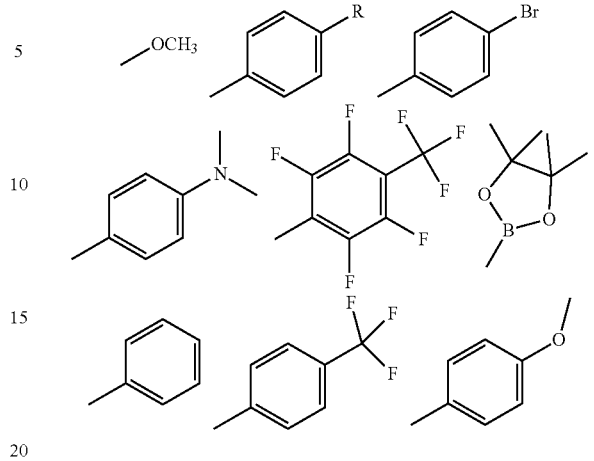

and wherein R is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, particularly, R has not more than 6 carbon atoms, wherein Z in formulae XXIII-XXV is selected from the following groups:

and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, in particular, $R_2$ has not more than 6 carbon atoms, wherein Ri in formulae XXIII-XXV is selected from the following groups:

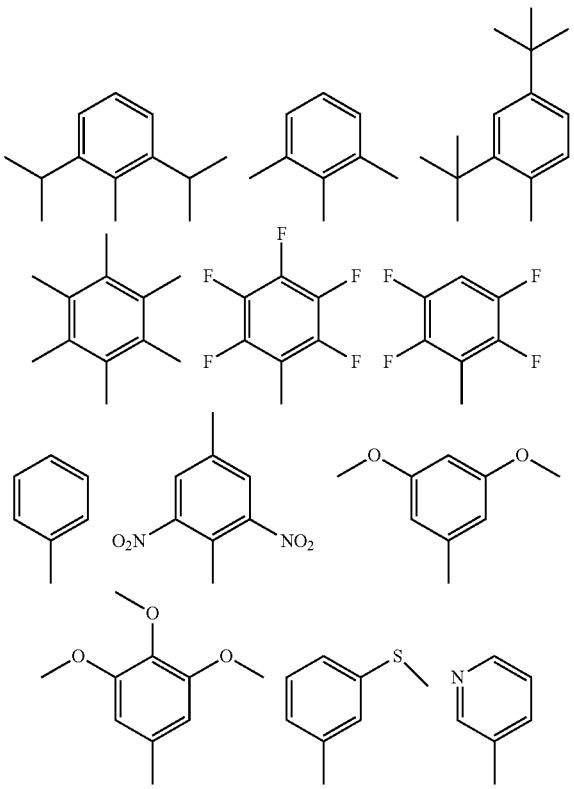

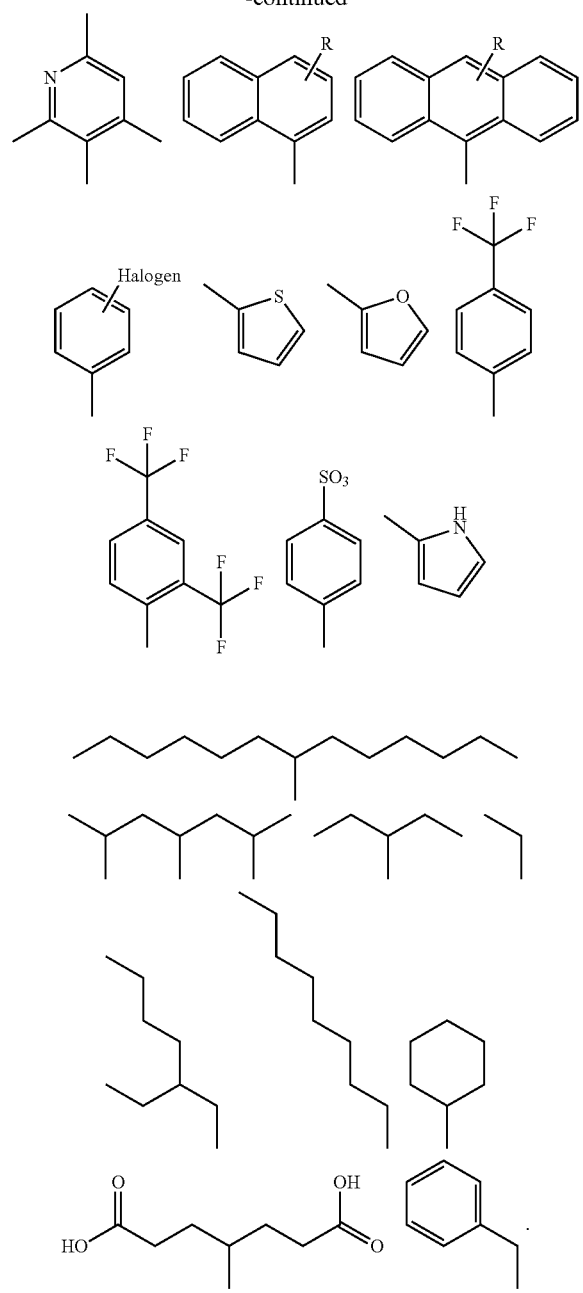
In one embodiment, W is selected from the following groups:
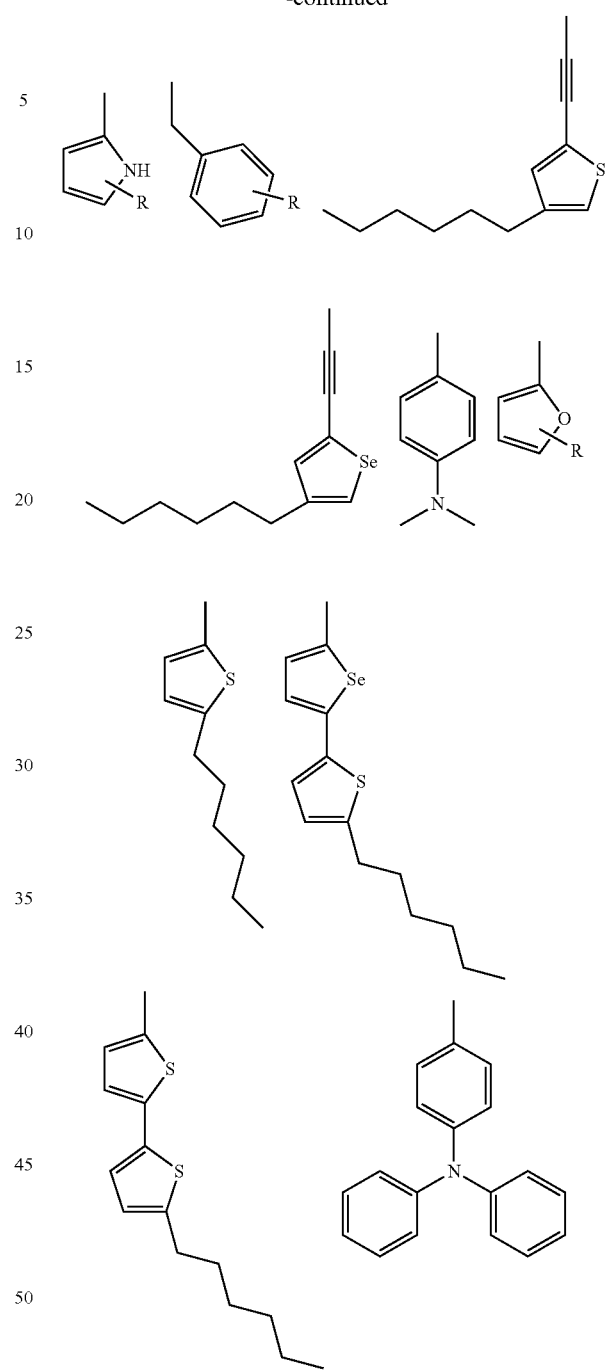

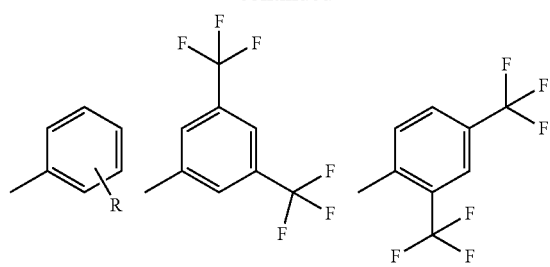
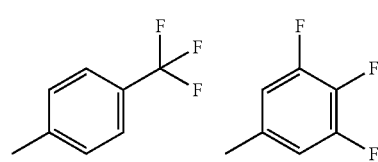
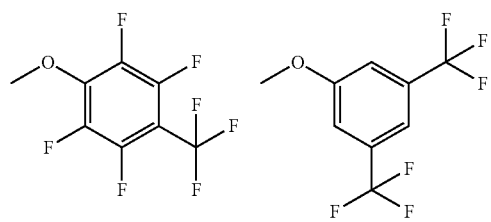
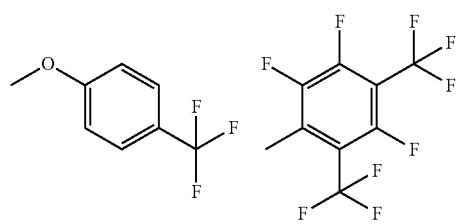
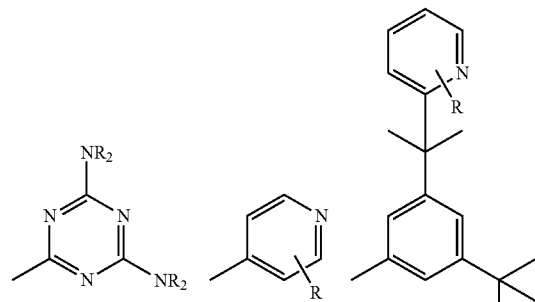
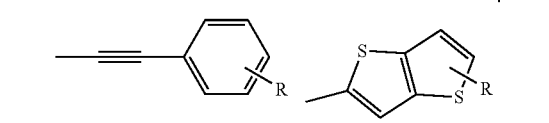
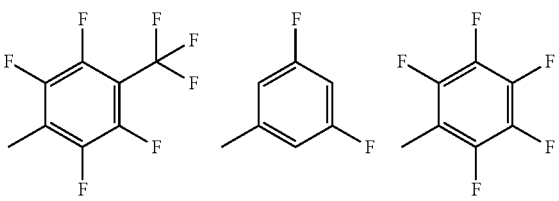
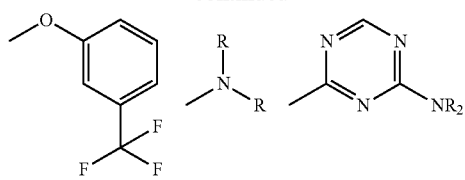
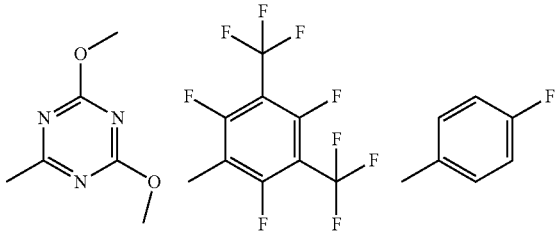
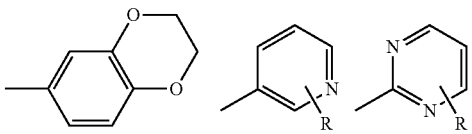
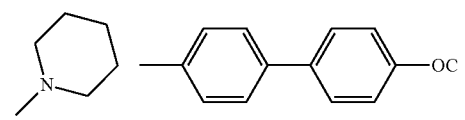
In one embodiment, said at least one light emitter has a structure selected from one of the following:
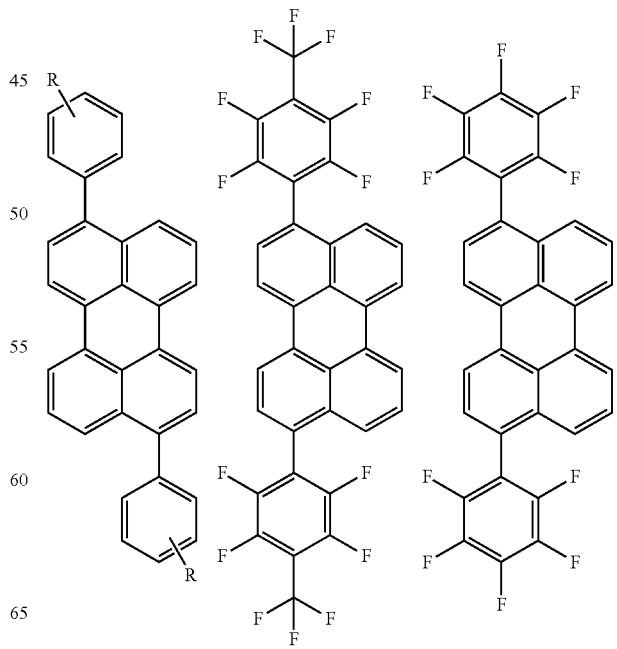

wherein R is a linear or branched alkyl group, particularly with not more than 6 carbon atoms.

In one embodiment, said at least one light emitter has the structure represented by Formula (XXVI) or includes a molecule having the structure represented by Formula (XXVI):

Formula (XXVI)

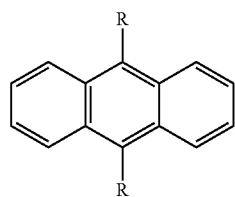

wherein R is selected from the following groups:

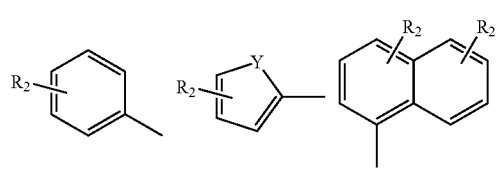

wherein Y is selected from the group consisting of $CH_2$, S, O, Se and N—$R_2$,
and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group,
wherein, particularly, $R_2$ has not more than 6 carbon atoms,
or wherein R is selected from the following groups:

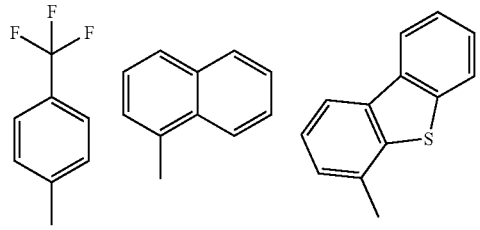

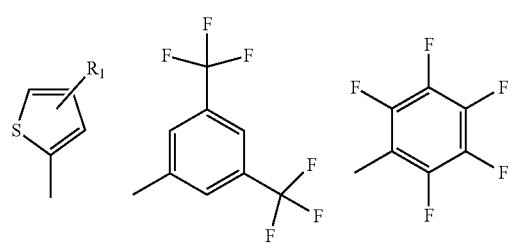

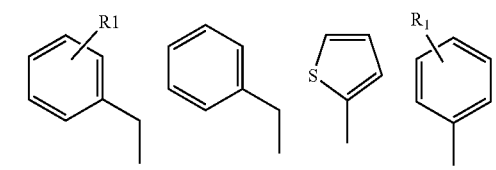

wherein $R_1$ is a linear or branched alkyl group, particularly with not more than 6 carbon atoms.

In one embodiment, said at least one light emitter has a structure selected from one of the following or includes a molecule having a structure selected from one of the following:

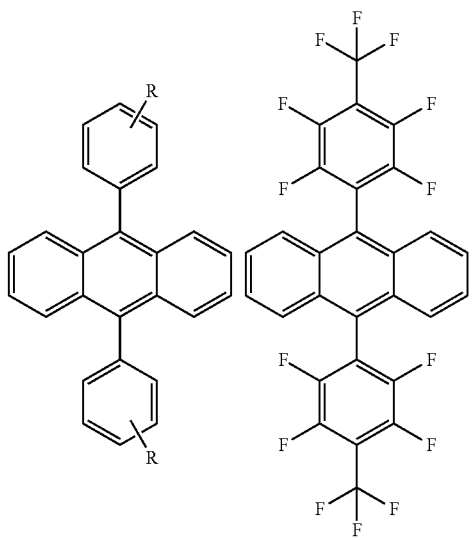
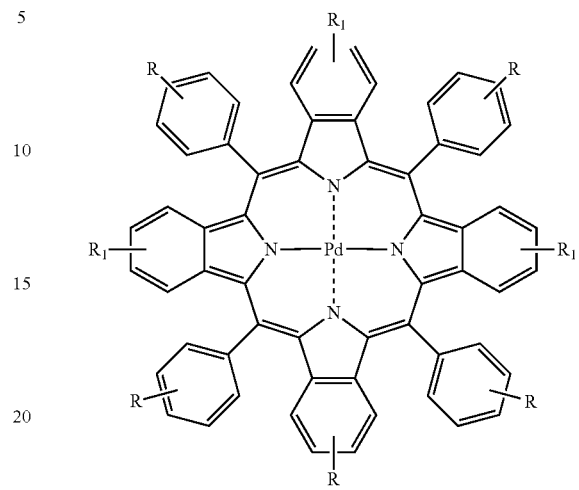
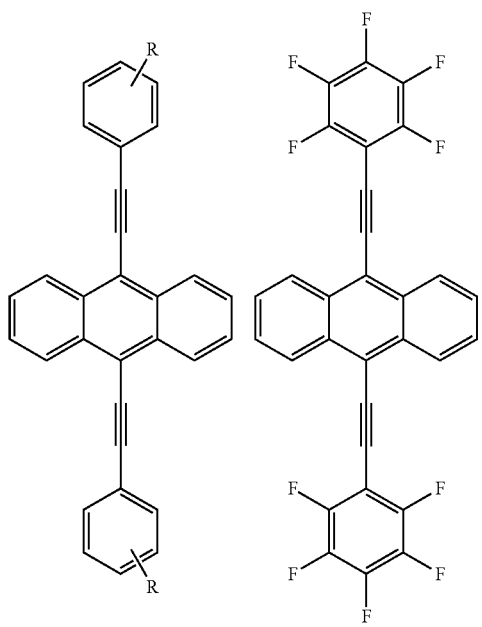

wherein R is a linear or branched alkyl group, particularly with up to 6 carbon atoms.

Said at least one sensitizer may be any dye with high intersystem crossing resulting in highly populated triplet state.

In one embodiment, said at least one sensitizer is or includes a porphyrin, particularly a benzo porphyrin or naphto porphyrins, or a phthalocyanine.

In one embodiment, said at least one sensitizer has the structure represented by Formula (XXVII) or includes a molecule having the structure represented by Formula (XXVII):

wherein $R_1$ is hydrogen, a linear or branched alkyl group, in particular with up to 6 carbon atoms, or a benzene ring, and wherein R is a linear or branched alkyl group, in particular with up to 6 carbon atoms.

In one embodiment, said at least one sensitizer has a structure represented by Formula (XXVIII), Formula (IXXX), Formula (XXX) or Formula (XXXI) or includes a molecule having a structure represented by Formula (XXVIII), Formula (IXXX), Formula (XXX) or Formula (XXXI):

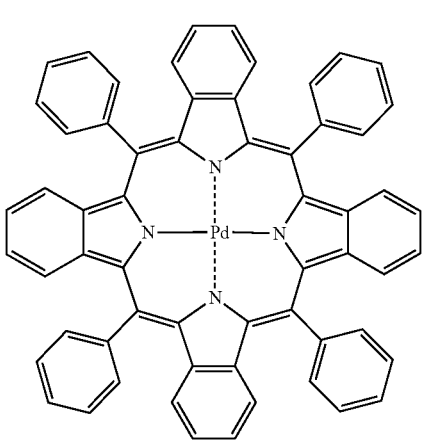

-continued

Formula (IXXX)

Formula (XXX)

Formula (XXXI)

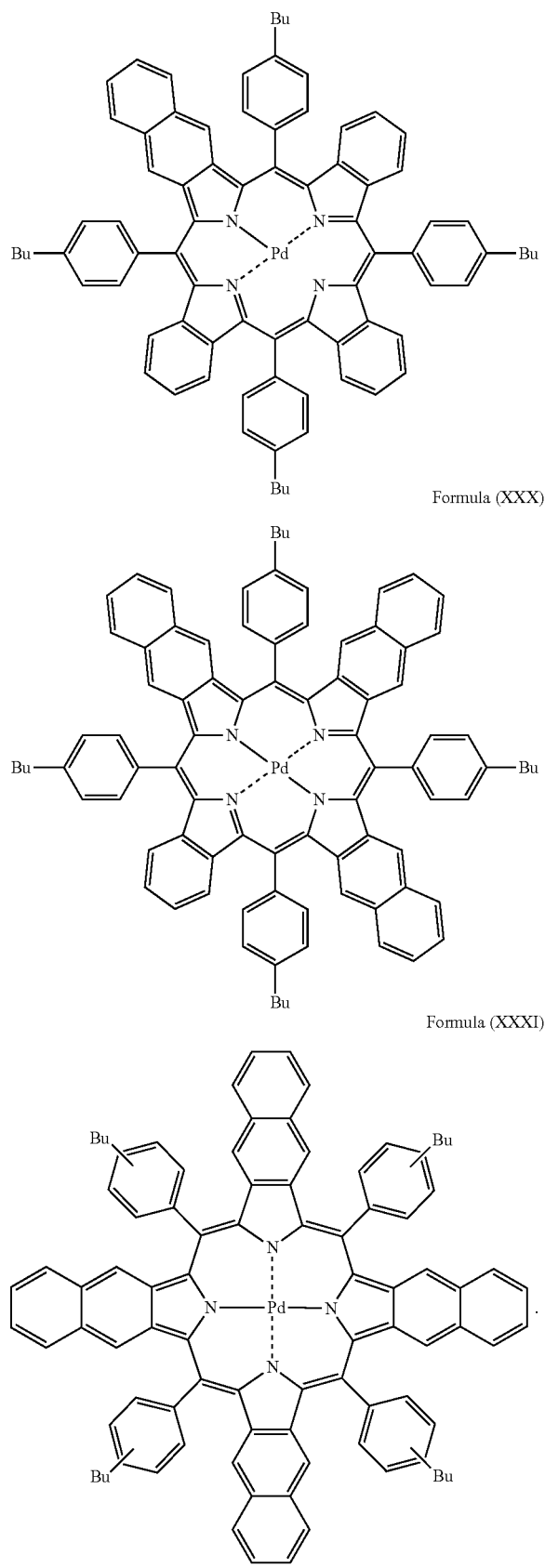

In one embodiment, said sensitizer has the structure represented by Formula (XXVIII):

Formula (XXVIII)

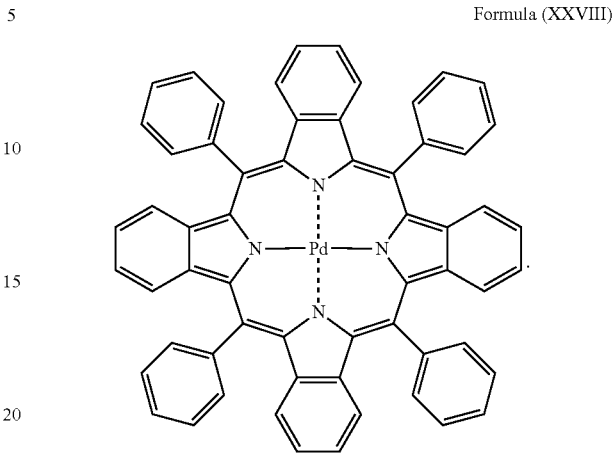

In one embodiment, said nanoparticle (NP) includes 1 to 4 metal nanoparticles (i.e. at least one but not more than 4 metal nanoparticles).

In one embodiment, the nanoparticle (NP) includes more than one metal nanoparticle.

In one embodiment, said nanoparticle (NP) does not include metal nanoparticles that are in contact with each other.

In one embodiment, said metal (plasmonic) nanoparticles are magnetic.

In one embodiment, said metal particles are plasmonic in that they are metal nanoparticles.

In one embodiment, said metal nanoparticles include or are composed of cobalt.

In one embodiment, said at least one metal nanoparticle has a diameter in the range of from 1 to 100 nm, particularly in the range of from 10 to 100 nm, more particularly in the range of from 10 to 50 nm.

As the skilled person will appreciate, for the plasmonic nanoparticles any metal particles with plasmon may be used, e.g. plasmonic metal nanoparticles. Typically, such metal nanoparticles have a plasmon and are herein also referred to as "plasmonic" metal nanoparticles. Without wishing to be bound by any theory, the present inventors believe that the electron density of such plasmonic metal nanoparticles can couple with radiation. i.e. plasmonic nanoparticles are used as particles whose electron density can couple with electromagnetic radiation of wavelengths that are far larger than the particle itself. In such a way plasmonic nanoparticles are capable of enhancing the emission of the emitters distributed in the nanoparticles.

In one embodiment, said metal (plasmonic) nanoparticles have a diameter in the range of from 1 to 100 nm, particularly in the range of from 4 to 80 nm, more particularly in the range of from 10 to 60 nm, more particularly in the range of from 10 to 50 nm. In one embodiment, such metal nanoparticle has an average diameter in the range of from 1 nm to 50 nm, particularly 1 nm to 30 nm, more particularly 1 nm to 20 nm. In one embodiment, it has an average diameter of from 10 nm to 50 nm, particularly 10 nm to 30 nm. In another embodiment, such metal nanoparticle has an average diameter of from 1 nm to 40 nm, particularly 5 nm to 30 nm. Typically, such metal nanoparticle having an average diameter of from 1 nm to 100 nm or an average diameter of any subrange therein is a plasmonic nanoparticle. If the present application indicates that a diameter, e.g. of metal nanoparticles, is in a certain range, this means that the average diameter of said metal nanoparticles falls in that certain range. In one embodiment, the diameter of individual metal nanoparticles varies by not more than 30%, particularly by not more than 20%, more particularly by not more than 10%.

In one embodiment, said nanoparticle (NP) includes a single metal nanoparticle. In one embodiment, said single metal nanoparticle forms the core of said nanoparticle (NP), wherein said polymeric organic matrix forms a shell around said core.

The metal particles may be composed of any metal or materials with plasmonic properties—and in this way are plasmonic nanoparticles (e.g. nanospheres, nanoshells, nanocubes, nanorods and nanoplates). In one embodiment, said at least one plasmonic nanoparticle consists of a material selected from the group consisting of Ag, Au and Co, Al, Cu, metal alloys/layered structures like Ag/Au or of nitrides of transition metals (TiN, ZrN). In one embodiment, said at least one plasmonic (metal) nanoparticle is composed of Ag.

In one embodiment, said at least one metal nanoparticle consists of only one element (i.e. it is composed of a pure chemical substance consisting of a single type of atom).

In one embodiment, said at least one metal nanoparticle does not include or consist of a rare-earth metal, rare-earth metal ions or compounds/material formed from a rare-earth element.

In one embodiment, said nanoparticle (NP) does not include rare-earth metal, rare-earth metal ions or compounds/material formed from a rare-earth element.

In one embodiment, said metal nanoparticles are massive particles (i.e. the interior of each metal nanoparticle is completely filled by the metal which said metal particle is made of, and the metal particle does not enclose any other material than said metal nor does it enclose any void space).

In one embodiment, the nanoparticle further (NP) includes at least one antioxidant. Inclusion of an antioxidant improves/optimizes the chromophore distribution and increases emission yield and photostability (emission enhancement and photostability enhancement). In one embodiment, said at least one antioxidant is an organic antioxidant. In one embodiment, said at least one antioxidant is soluble in an organic, water-miscible solvent, more particularly in THF or DHF. In one embodiment In wherein one embodiment, said at least one antioxidant is distributed homogeneously within said polymeric organic matrix. In one embodiment In one embodiment, said at least one antioxidant is selected from the group consisting of lipoic acid, vitamin E, a carotenoid and a ascorbic acid ester.

Different antioxidants—singlet oxygen scavengers or other reactive oxygen species scavengers (ROS scavengers) can be used. Generally, any antioxidant, especially singlet oxygen scavenger/quencher, can be used as far as it is soluble in an organic phase. The antioxidant does not need to be soluble in water (or at best only needs to have very limited solubility in water), but it should be well soluble in THF, DMF or ethanol (or other water miscible organic solvents which are also used as solvents for the other NP components). The following exemplary antioxidants can be used but the application is not limited to these examples: ascorbic acid palmitate (6-O-Palmitoyl-L-ascorbic acid), ascorbic acid esters, caffeic acid esters, lipoic acid (all racemic forms), lauryl gallate and other galic acid esters—octyl, butyl, ethyl esters; Vitamin E (α-Tocopherol, δ- or γ-Tocopherol and tocopherol acetates)—all racemic forms; Tocotrienol—all racemic forms, resveratrol; Pyrocatechol; 3-ethylbenzophenone; Magnolol, carnosol; Vitamin A—retinol (retinoic acid), retinol palmitate, retinol acetate, retinol esters, vitamin A aldehyde (retinal), carotene s—e.g. beta-carotene I and II, carotenal, mixtures of beta-carotenes, also lycopene; Ubiquinone (Coenyme Q-10), bromadiolon, vitamin K2, vitamin K3, flavones/flavonols (catehins, etc.), eugenol and others.

Designed combinations thereof—e.g. ascorbic acid palmitate with lipoic acid—can also be used.

In one embodiment, the nanoparticle (NP) includes functional groups at its surface that allow to covalently couple a molecule to the nanoparticle. In one embodiment, said functional groups are selected from the group consisting of —COOH (carboxylate), —NH$_2$, —SH (thiol), —NHS, alkynyl, —N$_3$, aldehyde, ketone and biotin group, more particularly said functional groups are —COOH or —NH$_2$.

In one embodiment, the nanoparticle (NP) includes molecules or chemical groups attached to its surface that are capable of specifically binding to an analyte molecule or that have an enzymatic activity that allows to detect an analyte molecule. In one embodiment, said molecules attached to the surface of the nanoparticle are protein molecules. In one embodiment, said molecules attached to the surface of the nanoparticle are antibody molecules. In one embodiment, said analyte molecule is a biomolecule. In one embodiment, said analyte molecule is selected from the group consisting of a nucleic acid/(poly-) nucleotide, such as DNA or RNA, (poly-)peptide/protein, carbohydrate, lipid, glycoprotein, lipoprotein, viral and/or bacterial antigen, and pharmaceutical.

In a situation where said molecules attached to the surface of the nanoparticle are antibody molecules, the skilled person will appreciate that a requirement for the detection of an antigen as analyte is the stable binding (covalent or non-covalent) of the antibody on the surface of the nanoparticles without losing the selectivity of the antibody (i.e. a free active site is needed). If the antigen is attached to the fluorescent label, detection can be achieved by a competition assay.

In one embodiment, said nanoparticle (NP) has a modified surface such that their uptake by cells is increased. In one embodiment, the surface of said nanoparticles is modified by attachment of proteins. Such a surface modification that allows for increased uptake by cells facilitates is advantageous if the nanoparticles are to be used for cell imaging after uptake or for flow cytometry after uptake.

In one embodiment, the surface of said nanoparticles is modified by attachment of specific antibodies or with functional moieties. Such a surface modification allows for attachment of the nanoparticles to the surface of different cells, when the nanoparticles are used for flow cytometry or fluorescence assisted cell sorting.

An example for detection of an analyte upon binding to the surface of a nanoparticle (NP) according to the present disclosure may, for example, be a protein like bovine serum albumin (BSA), which may be detected via luminescence resonance energy transfer (LRET) in up-conversion regime. The nanoparticle (NP) has analyte-specific surface modifications like carboxy- or amino groups. Specific binding of the analyte can be supported also e.g. by antibody, affibody or aptamers. In case of luminescence resonance energy transfer (LRET) the size of the analyte is small, particularly 1-10 nm. The conjugation of an analyte onto the photon up-conversion nanoparticle surface allows a LRET in presence of a fluorescent label. In the absence of the analyte, no photon up-conversion signal is observed.

The nanoparticles according to the disclosure may detect the presence of analytes by effects on the photon up-conversion of the particles upon binding of the analyte to the surface of the nanoparticles.

As discussed above, the present disclosure also provides a sensing layer including nanoparticles according to the present disclosure as defined in any of the embodiments above.

The nanoparticles (NP) according to the present disclosure may be included in a layer prepared from a biodegradable material that allows to detect the presence of analyte molecules, i.e. in a sensing layer. Such sensing layer or "emissive layer" or "emissive sensing layer" (ESL) may form part of a sensor. A "sensor", as used herein, refers to an arrangement of an "emissive sensing layer" on a substrate. Such sensor may include one or several additional layers, as necessary, adding functionality e.g. selected from cell adhesion layers, coating layers, enhancement layers for enhancing the intensity of the light emitted from the emissive layer, attachment layers etc.

The polymeric organic matrix of said nanoparticles may be prepared from a biodegradable material. In one embodiment, said biodegradable material is a material that is degraded by cells growing on said layer or nanoparticles or in proximity to said layer or nanoparticles.

By detecting the disappearance over time of the fluorescence/phosphorescence/up-conversion emission of the layer/nanoparticles, the presence of such cells can be detected.

As discussed above, the present disclosure also provides a method of producing nanoparticles (NP) as defined in any of the embodiments above, said nanoparticles (NP) including
  a polymeric organic matrix,
  at least one light emitter distributed within said matrix,
  optionally at least one sensitizer and/or at least one antioxidant distributed within said matrix,
  a stabilizing agent, and
  at least one plasmonic metal nanoparticle enclosed within said matrix,
wherein said at least one metal nanoparticle is capable of enhancing the intensity of the light emitted by said light emitter(s) by way of plasmon enhancement, said method including the steps of:
  providing a polymer or combination of polymers or combination of polymers with small molecules from which the polymeric organic matrix is to be formed, a stabilizing agent, at least one light emitter, plasmonic metal nanoparticles, and optionally at least one sensitizer and/or at least one antioxidant,
  preparing a dispersion of said plasmonic metal nanoparticles in an organic water-miscible solvent, particularly upon ligand exchange of said plasmonic metal nanoparticles,
  preparing a mixture of said polymer or combination of polymers or combination of polymers with small molecules from which the polymeric organic matrix is to be formed, said stabilizing agent, said light emitter(s) and optionally said sensitizer(s) and/or said antioxidant in an organic water-miscible solvent,
  adding said mixture of said polymer or combination of polymers or combination of polymers with small molecules, said stabilizing agent, said light emitter(s) and optionally said sensitizer(s) and/or said antioxidant(s) to said dispersion of metal nanoparticles or vice versa, thus forming a mixture including said metal nanoparticles,
  inducing said mixture including said plasmonic metal nanoparticles to form nanoparticles (NP), thus forming a dispersion of nanoparticles (NP) wherein said nanoparticles (NP) include a polymeric organic matrix with said light emitter(s) and, optionally, said sensitizer(s) and/or said antioxidant(s), distributed therein, and wherein said metal nanoparticles are enclosed in said polymeric organic matrix.

In this method of producing nanoparticles (NP), said nanoparticles (NP), said polymeric organic matrix, said at least one light emitter, said at least one sensitizer, said at least one antioxidant, said metal nanoparticles and said stabilizing agent are as defined in any of the embodiments above.

Said mixture including said plasmonic metal nanoparticles may be induced to form nanoparticles (NP) by adding cold water. Upon formation of said dispersion of nanoparticles (NP), said organic, water-miscible solvent(s) may be removed again from said dispersion of nanoparticles by evaporation from the dispersion with a rotary evaporator at low pressure, e.g. subatmospheric pressure, and elevated temperature.

Subsequently, said dispersion may be subjected to centrifugation using a filter with a molecular weight exclusion limit of <7 000 Da (such that the nanoparticles (NP) are recovered, whereas water and components with a molecular weight below the exclusion limit of the filter (e.g. not used surfactant molecules, some emitter aggregates or matrix components not incorporated in the nanoparticles) are removed).

Upon obtaining said nanoparticles (NP) from the centrifugation step, said nanoparticles can be re-distributed in pure distilled water. Optionally, the nanoparticles may be purified by dialysis or with HiTrap filters (desalting).

In one embodiment, in the step of providing said polymer or combination of polymers or combination of polymers with small molecules from which the polymeric organic matrix is to be formed, said stabilizing agent, said at least one light emitter, said plasmonic metal nanoparticles, and optionally said at least one sensitizer and/or said at least one antioxidant, all these components are provided dissolved/suspended in an organic, water-miscible solvent, wherein, more particularly, said organic, water-miscible solvent is THF or DMF.

In one embodiment, prior to inducing said mixture including said metal (plasmonic) nanoparticles to form nanoparticles (NP) said mixture including said plasmonic metal nanoparticles is brought to a temperature of 0° C.

In one embodiment, said step of inducing said mixture including said plasmonic metal nanoparticles to form nanoparticles (NP) is achieved by adding water, particularly cold water, more particularly water having a temperature of 4° C.

In one embodiment, upon formation of said dispersion of nanoparticles (NP), said organic, water-miscible solvent(s) is removed again from said dispersion of nanoparticles (NP), e.g. by evaporation.

As discussed above, the present disclosure provides the use of nanoparticles (NP) as defined in any of the embodiments described above in a biological application selected from the group consisting of labeling and/or detection of cells, biological (macro-)molecules or other analytes, fluorescence microscopy, (flow) cytometry, fluorescence-activated cell sorting (FACS), fluorescence resonance energy transfer (FRET), immunohistochemistry, clinical immunoassays, fluorescence-quenching-based enzyme-activity assays, high-throughput screening, molecular diagnostics, sensing of temperature, sensing of pressure and sensing of oxygen.

In this use, said nanoparticles (NP) are as defined in any of the embodiments above.

The nanoparticles (NP) according to the present disclosure have various advantages that allow to use them in diverse applications. Thus, nanoparticles according to the present disclosure show for example fluorescent and/or up-conversion emisson with increased brightness, increased emission stability and increased signal-to-noise ratio compared to known nanoparticles in the art. Such advantages are achieved, to a differing extent, by the features of the different embodiments described above as well as by combinations thereof. The light emitters according to the present disclosure show a higher brightness/higher fluorescence quantum yield and a higher stability compared to known light emitters in the art. The inclusion of a radical scavenger, such as an antioxidant into the nanoparticles has the further advantage that protection of all chromophores (emitter(s) and sensitizer(s) (when used)) against reactive radicals and reactive oxygen species is provided. Additionally, the radical scavenger, e.g. the antioxidant hinders the transfer of any excited triplet state to oxygen molecules, which stops the singlet oxygen formation as well.

Different antioxidants—singlet oxygen scavengers or other reactive oxygen species scavengers (ROS scavengers) can be used. Generally, any antioxidant, especially singlet oxygen scavenger/quencher, can be used as far as soluble in the organic phase. They need to be not soluble, or have very limited solubility, in water but be well soluble in THF, DMF or ethanol (or other water miscible organic solvents which are also solvents for the other NP components). The following antioxidants can be used but the application is not limited to these examples: ascorbic acid palmitate (6-O-Palmitoyl-L-ascorbic acid), ascorbic acid esters, caffeic acid esters, lipoic acid (all racemic forms), lauryl gallate and other galic acid esters—octyl, butyl, ethyl esters; Vitamin E ($\alpha$-Tocopherol, $\delta$- or $\gamma$-Tocopherol and tocopherol acetates)—all racemic forms; Tocotrienol—all racemic forms, resveratrol; Pyrocatechol; 3-ethylbenzophenone; Magnolol, carnosol; Vitamin A—retinol (retinoic acid), retinol palmitate, retinol acetate, retinol esters, vitamin A aldehyde (retinal), carotene s—e.g. beta-carotene I and II, carotenal, mixtures of beta-carotenes, also lycopene; Ubiquinone (Coenyme Q-10), bromadiolon, vitamin K2, vitamin K3, flavones/flavonols (catehins, etc.), eugenol and others Designed combinations thereof—e.g. ascorbic acid palmitate with lipoic acid—can also be used.

Furthermore, the nanoparticles according to the present disclosure can have a functional surface and/or be biocompatible or biodegradable. Such nanoparticles can be used for e.g. flow cytometry (or any cytometry in general, including imaging). Moreover, they can be used for live cell imaging (e.g. after uptake of the nanoparticles into the cells). In addition, the nanoparticles can be optimized specifically via attachment of proteins, antibodies, enzymes and other specific groups on their surface and used for sensing/imaging of oxygen (photon up-conversion nanoparticles), temperature (typically by using an emitter that is a phosphorescent chromophore—i.e. the sensitizer type of molecules as emitter), biologically active molecules, e.g. in neurotransmitters sensing (photon up-conversion nanoparticles or fluorescence intensity change), or the detection of singlet oxygen. The sensing/imaging/detection can be carried out in/around live cells or in any other biotechnological context. Moreover, the nanoparticles according to the present disclosure can be incorporated into biocompatible/cell compatible sensing layers. Alternatively, the nanoparticles can be made cell-permeable for imaging/sensing inside live cells.

The term "polymeric organic matrix", as used herein, is meant to refer to a matrix that includes a polymer or is made up of a polymer which includes carbon-carbon bonds For example it may include or be composed of a polysiloxane. In one embodiment, the term refers to a polymer that has a carbon chain backbone. A "polymer" is a substance composed of molecules characterized by the multiple repetition of one or more species of monomers. In this context, a "multiple repetition of monomers" is meant to refer to 10 or more, particularly 50 or more, more particularly 100 or more monomers linked to each other.

If the present application states that a component A is "chemically inert" with respect to a component B, this means that component A does not chemically react with component B.

The term "light emitter", as used herein, refers to a molecule or combination of molecules that, upon irradiation with light of a certain excitation wavelength, is capable of emitting light of a certain emission wavelength. The emitted light may be generated by luminescence, particularly fluorescence.

A "metal nanoparticle", as used herein, is a metal particle having an average diameter <1 µm. As the skilled person will appreciate, for the metal nanoparticles any metal particles with plasmon may be used, e.g. metal nanoparticles. Typically, such metal nanoparticles have a plasmon and are herein also sometimes referred to as "plasmonic" metal nanoparticles. Without wishing to be bound by any theory, the present inventors believe that the electron density of such plasmonic metal nanoparticles can couple with electromagnetic radiation of wavelengths that are far larger than the particle itself.

In one embodiment, said metal nanoparticles have a diameter in the range of from 1 to 100 nm, particularly in the range of from 4 to 80 nm, more particularly in the range of from 10 to 60 nm, more particularly in the range of from 10 to 50 nm. In one embodiment, such metal nanoparticle has an average diameter in the range of from 1 nm to 50 nm, particularly 1 nm to 30 nm, more particularly 1 nm to 20 nm. In one embodiment, it has an average diameter of from 10 nm to 50 nm, particularly 10 nm to 30 nm. In another embodiment, such metal nanoparticle has an average diameter of from 1 nm to 40 nm, particularly 5 nm to 30 nm. Typically, such metal nanoparticle having an average diameter of from 1 nm to 100 nm or an average diameter of any subrange therein is a plasmonic nanoparticle. If the present application indicates that a diameter, e.g. of metal nanoparticles, is in a certain range, this means that the average diameter of said metal nanoparticles falls in that certain range. In one embodiment, the diameter of individual metal nanoparticles when prepared in different runs from the same composition of the organic phase and the same mixing conditions varies by not more than 30%, particularly by not more than 20%, more particularly by not more than 10%.

If the present disclosure refers to a metal particle being "enclosed within" a matrix, this designates a situation where said metal particle is surrounded at all sides by said matrix, such that the surface of said metal particle is completely covered by said matrix. If more than one metal particle is enclosed within the organic nanoparticle—they are enclosed as single particles with no contact to each other which is essential for keeping their plasmon intact to ensure plasmon enhancement.

If the present disclosure refers to a metal nanoparticle being capable of "enhancing the intensity" of light emitted by a light emitter, this designates a situation where said metal nanoparticle is capable of enhancing the number of photons emitted per number of photons absorbed and/or the photostability. If the present disclosure refers to a metal nanoparticle being capable of "enhancing the luminescence or photon up-conversion emission" of the nanoparticles (NP) by plasmon enhancement, this designates a situation where said metal nanoparticle is capable of enhancing the intensity (number of photons emitted per number of photons absorbed) and/or the photostability of said nanoparticle (NP). With the nanoparticles (NP) according to the disclosure, such effects are even more pronounced at higher excitation intensities, i.e. where the photostability is more difficult to keep otherwise.

A "perylene", as used herein, is a molecule having the following structure:

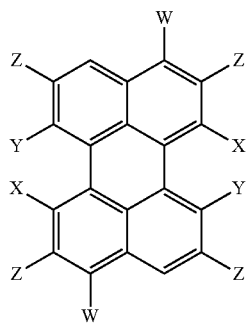

wherein W, X, Y and Z are suitable substituents.

A "perylene monoimide", as used herein, is a molecule having the following structure:

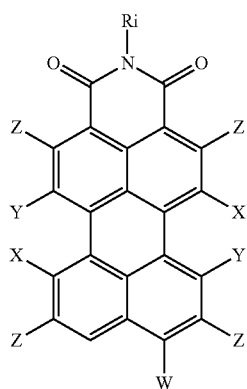

wherein W, X, Y, Z and Ri are suitable substituents.

A "perylene diimide", as used herein, is a molecule having the following structure:

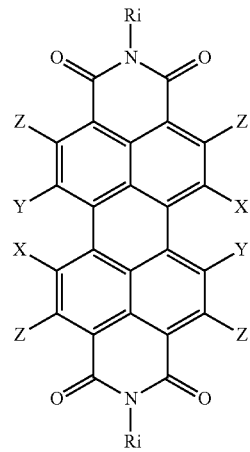

wherein X, Y, Z and Ri are suitable substituents. "Suitable" substituents" are manifold and can be determined by a person skilled in the art.

A "sensitizer" is a chromophore molecule which is able to absorb light, particularly with high populated triplet states, and capable to transfer the excited triplet state to a suitable light emitter. The combination of sensitizer and emitter molecules with triplet-triplet transfer can achieve photon up-conversion—also as described in EP 2298849 or US 2010/0330026 A1. The sensitizer may be a metal-organic complex. Upon irradiation, the sensitizer absorbs light at the excitation wavelength. By an up-conversion process e.g. based on direct or sequential two-photon excitation or on direct or sequential multi-photon excitation or on excitation of molecules populating high vibrational state(s) ("hot-band absorption"), or an up-conversion process based on a triplet-triplet annihilation process between photoexcited molecules of said light emitter and/or based on a triplet-triplet annihilation process between photo-excited molecules of said sensitizer, a higher energy state is generated, leading to emission of light at the emission wavelength by the light emitter.

Examples of sensitizers suitable for photon up-conversion are the compounds shown in Formulas IXXX-XXXI above. Examples of light emitters suitable for photon up-conversion are the compounds shown in Formulas VII-IX and XVII-XXII.

A "stabilizing agent", as used herein, is a non-ionic or ionic surfactant (surface active molecule or polymer) and ensures the nanoparticle formation/dispersion and the functional groups on the surface (COOH or $NH_2$, or other) of the nanoparticles. The stabilizing agent occupies the surface of the organic nanoparticles (NP). Through its hydrophobic part, the stabilizing agent interacts with the organic core of the nanoparticle (NP) (where the chromophores, which are not water-soluble, are present). Through its hydrophilic part, the stabilizing gent is exposed to the aqueous/polar environment surrounding the nanoparticles (NP). Thus, the stabilizing agent allows for formation of nanoparticles and stabilizes the nanoparticles in the dispersion.

A "metal nanoparticle", as used herein, is used synonymously with "plasmonic" nanoparticle. Plasmon enhancement of emission by plasmonic nanoparticle is the target. Without wishing to be bound by any theory, the term "plasmonic nanoparticles" refers to nanoparticles whose electron density can couple with electromagnetic radiation of wavelengths that are far larger than the particle. It refers to a plasmonic nanoparticle consisting of a metal, a combination of different metals or a metal alloy or a nitride of transition metal. In one embodiment, a "metal nanoparticle" consists of one metal (i.e. of atoms of only one chemical element)—Ag.

If the present disclosure refers to a metal nanoparticle being "enclosed within" a matrix, this designates a situation where said metal particle is surrounded at all sides by said matrix, such that the surface of said metal particle is completely covered by said matrix.

At some instances, the present application may refer to metal particles or metal nanoparticles "that are in contact with each other". If a metal nanoparticle A "is in contact with" a metal nanoparticle B, this designates a situation where metal nanoparticle A and metal nanoparticle B directly touch each other, i.e. there is no intervening layer of a material that is neither part of metal nanoparticle A nor part of metal nanoparticle B, nor a gap, between said metal nanoparticle A and said metal nanoparticle B.

If the present disclosure indicates that a molecule is capable of "specifically binding" to a certain analyte, this refers to a situation where the dissociation constant for the interaction of said molecule and said analyte is <1 µM, particularly <100 nM, more particularly <10 nM.

A molecule with an "enzymatic activity that allows to detect an analyte molecule" is a molecule that catalyzes an enzymatic reaction that is dependent on or strongly influenced by the presence/absence of the analyte molecule to be detected (e.g. because it is a substrate of the catalyzed reaction or because the catalytic activity of the molecule with enzymatic activity is strongly influenced by the presence/absence of the analyte molecule to be detected), such that by monitoring the reaction catalyzed by said molecule with enzymatic activity of said molecule changes regarding the presence/absence of the analyte molecule with an enzymatic activity that allows to detect said analyte molecule, conclusions about the presence/absence of said analyte molecule or about changes in the concentration of said analyte molecule can be detected.

As the skilled person will appreciate, the detection of an analyte via enzyme activity requires the stable binding (covalent or non-covalent) of the enzyme to the surface of the nanoparticle without losing the activity of the enzyme (i.e. a free active site is needed). The molecule with an enzymatic activity that allows to detect the analyte molecule may for example be an oxidase that is covalently attached to the nanoparticle surface, and the analyte to be detected the substrate of said oxidase. In the presence of the analyte, the oxidase reaction generates light that excites the light emitter(s) (or sensitizer(s)) in the nanoparticle, wherein the light eventually emitted by the nanoparticle is further enhanced by the metal particles present in the nanoparticle The tetra "biomolecule" and "biological molecule" are used interchangeably herein and refer to any molecule produced by a living cell or a living organism (including viruses). This may include, but is not limited to macromolecules such as proteins, polysaccharides, lipids, and nucleic acids (including DNA and RNA), as well as small molecules such as primary metabolites, secondary metabolites, and natural products. In particular, it refers to neurotransmitters, oxygen and reactive oxygen species, hormones, antioxidants and vitamins, The term "biologically active molecule" refers to a molecule that is capable of facilitating or inducing a specific cellular or tissue response.

Note that the present technology can also be configured as described below in the following embodiments:

Embodiments

1. A nanoparticle (NP) including a polymeric organic matrix, at least one light emitter distributed within said matrix, a stabilizing agent, and at least one metal nanoparticle enclosed within said matrix, wherein said at least one metal nanoparticle is a plasmonic nanoparticle.

2. The nanoparticle according to embodiment 1, wherein said polymeric organic matrix is composed of a material or a combination of materials selected from the group consisting of polyacrylonitriles, polystyrenes and oligostyrenes, styrene copolymers, styrene-butadiene copolymers, polystyrene-based elastomers, polyethylenes and oligoethylenes, polyphenylenes and polyphenylene dendrimers, polypropylenes, polytetrafluoroethylenes, extended polytetrafluoroethylenes, polyacrylates, polymethylmethacrylates, ethylene-co-vinyl acetates, polysiloxanes, such as polymethylsiloxanes and polyphenylmethylsiloxanes, e.g. polydimethylsiloxane or polyphenylmethylsiloxane, their copolymers as well as substituted and modified polysiloxanes, polyethers, polyurethanes, polyether-urethanes, polyethylene terephthalates and polysulphones, or any copolymers of the listed polymers, particularly a material selected from the group consisting of polystyrenes, polyacrylonitriles and polymethylmethacrylates, more particularly polymethylmethacrylate.

3. The nanoparticle according to any of the foregoing embodiments, wherein said light emitter is capable of emitting light by luminescence, in particular by fluorescence or by phosphorescence, more particularly by fluorescence.

4. The nanoparticle according to any of the foregoing embodiments, wherein said nanoparticle is capable of photon up-conversion.

5. The nanoparticle according to any of the foregoing embodiments, wherein said nanoparticle further includes at least one sensitizer, wherein, in particular, said at least one sensitizer is capable of absorbing light at a first wavelength region $w \leq \lambda_1 \leq x$, and said at least one light emitter is capable of emitting light at a second wavelength region $y \leq \lambda_2 \leq z$, wherein $\lambda_2 \leq \lambda_1$, wherein, upon absorption of light by said at least one sensitizer at said first wavelength region $w \leq \lambda_1 \leq x$, said at least one light emitter emits light at said second wavelength region $y \leq \lambda_2 \leq z$.

6. The nanoparticle according to any of the foregoing embodiments, wherein said at least one light emitter is a molecule selected from the group consisting of anthracenes, perylenes, perylene derivatives such as perylene monoimides or perylene diimides, coumarins and BODIPY dyes, wherein, in particular, said at least one light emitter has a structure represented by Formula (I) or (II) or includes a molecule having the structure represented by Formula (I) or (II):

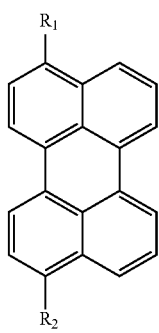

Formula (I)

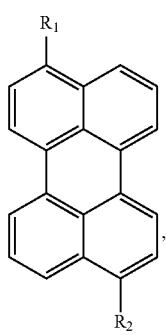

Formula (II)

wherein $R_1$ and $R_2$ are independently selected from the group consisting of hydrogen and a moiety with the structure represented by Formula (III), wherein at least one of $R_1$ and $R_2$ is a moiety with the structure represented by Formula (III):

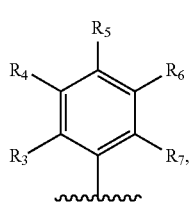

Formula (III)

wherein $R_3$, $R_4$, $R_5$, $R_6$ and $R_7$ are independently selected from the group consisting of H, F, and tri-fluoro-methyl (—$CF_3$), wherein at least one of $R_3$, $R_4$, $R_5$, $R_6$ and $R_7$ is F or tri-fluoro-methyl (—$CF_3$), wherein, in particular, $R_1$ and/or $R_2$ is a moiety represented by Formula (IV), Formula (V) or Formula (VI):

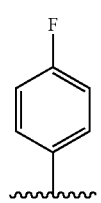

Formula (IV)

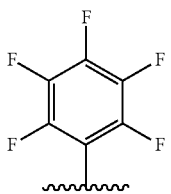

Formula (V)

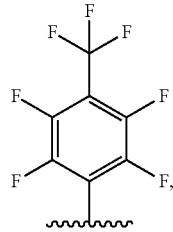

Formula (VI)

wherein, more particularly, said at least one light emitter has a structure represented by Formula (VII), Formula (VIII) or Formula (IX), or includes a molecule having the structure represented by Formula (VII), Formula (VIII) or Formula (IX):

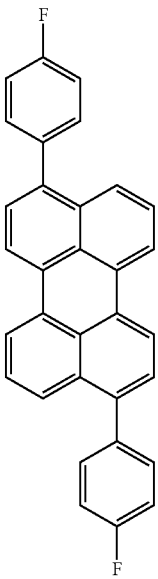

Formula (VII)

-continued

Formula (VIII)

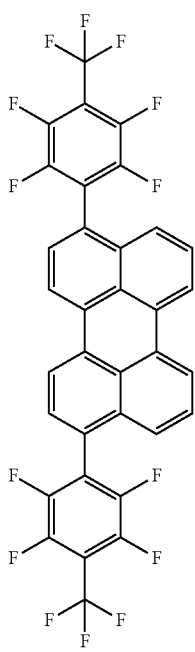

or wherein said at least one light emitter has the structure represented by Formula (X) or includes a molecule having the structure represented by Formula (X):

Formula (X)

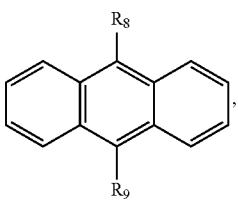

wherein $R_8$ and $R_9$ are independently selected from the group consisting of hydrogen and a moiety with the structure represented by Formula (XI), wherein at least one of $R_8$ and $R_9$ is a moiety with the structure represented by Formula (XI):

Formula (XI)

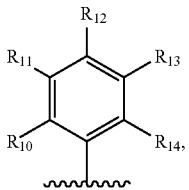

wherein $R_{10}$, $R_{11}$, $R_{12}$, $R_{13}$ and $R_{14}$ are independently selected from the group consisting of H, F, and tri-fluoro-methyl (—$CF_3$), wherein at least one of $R_{10}$, $R_{11}$, $R_{12}$, $R_{13}$ and $R_{14}$ is F or tri-fluoro-methyl (—$CF_3$), wherein, more particularly, $R_8$ and/or $R_9$ is the moiety represented by Formula (XII), Formula (XIII), Formula (XIV), Formula (XV) or Formula (XVI):

Formula (XII)

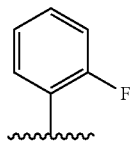

Formula (XIII)

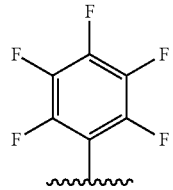

Formula (XIV)

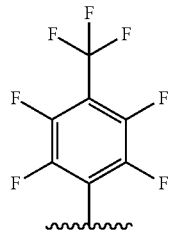

Formula (XV)

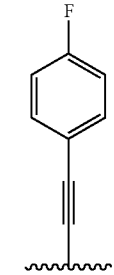

Formula (IX)

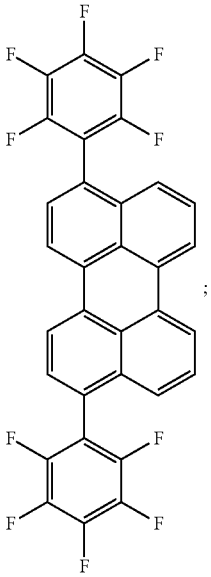

;

Formula (XVI)

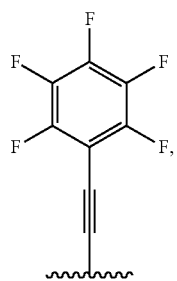

or wherein, more particularly, said at least one light emitter has the structure represented by Formula (XVII), Formula (XVIII), Formula (XIX), Formula (XX), Formula (XXI) or Formula (XXII), or includes a molecule having the structure represented by Formula (XVII), Formula (XVIII), Formula (XIX), Formula (XX), Formula (XXI) or Formula (XXII):

Formula (XVII)

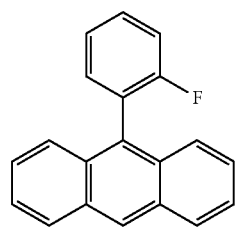

Formula (XVIII)

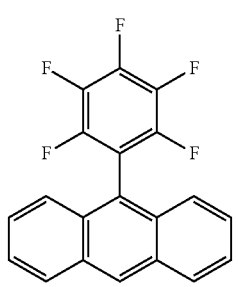

Formula (XIX)

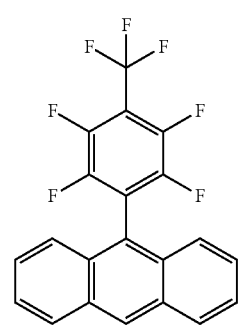

Formula (XX)

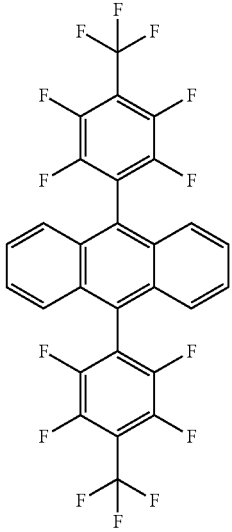

Formula (XXI)

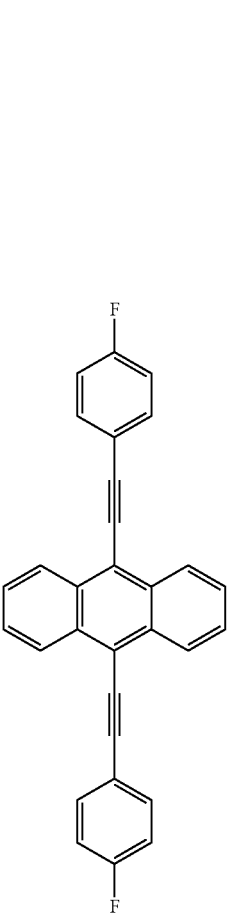

Formula (XXII)
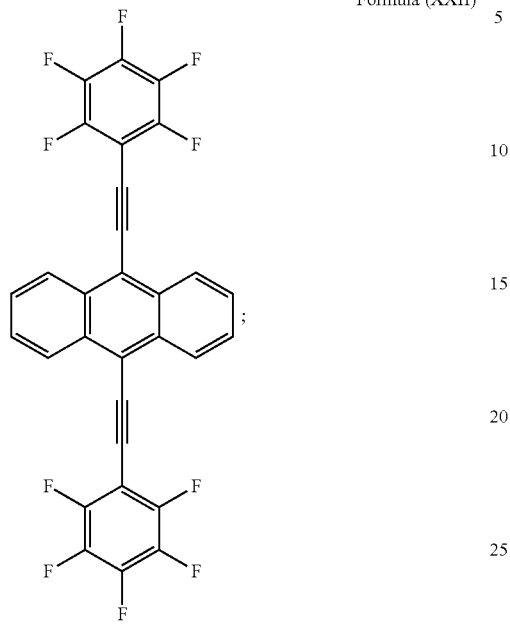
or wherein said at least one light emitter has a structure represented by one of the following structures or includes a molecule having a structure represented by one of the following structures:
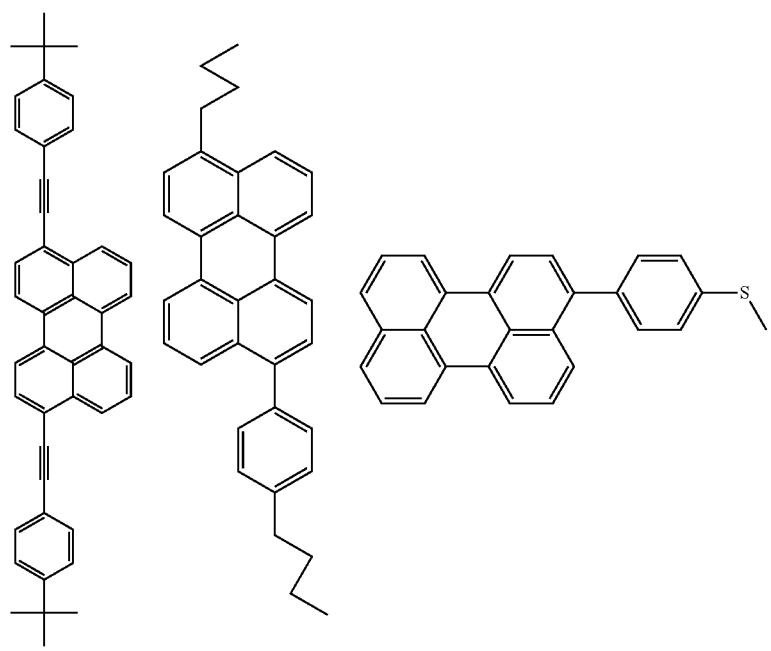

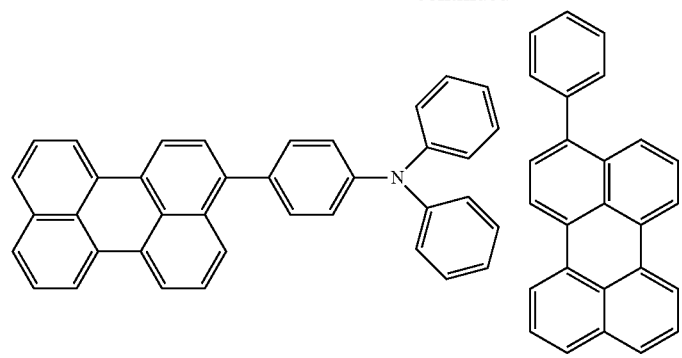
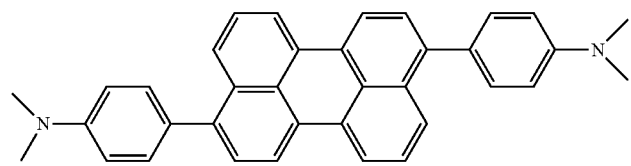
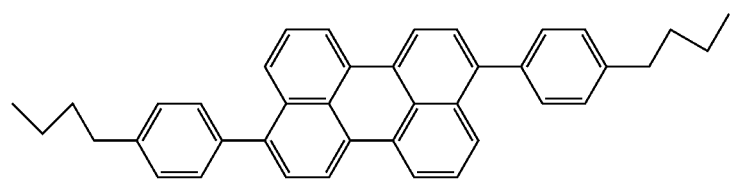
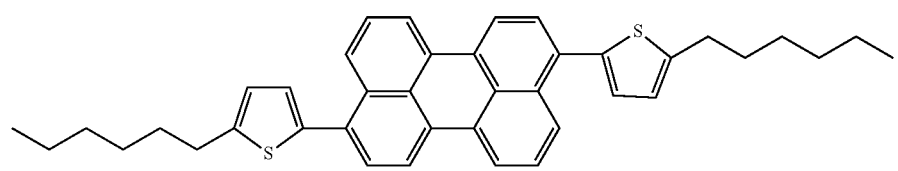

or wherein said light emitter has the structure represented by Formula (XXIII), (XXIV) or (XXV) or includes a molecule having the structure represented by Formula (XXIII), (XXIV) or (XXV):

Formula (XXIII)

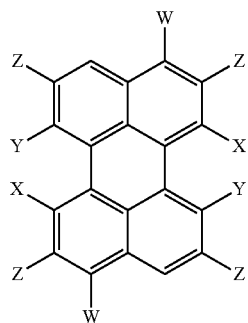

Formula (XXIV)

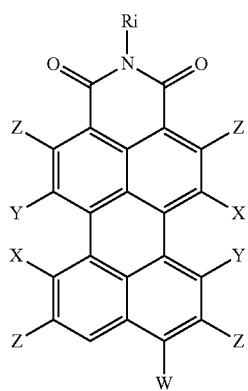

Formula (XXV)

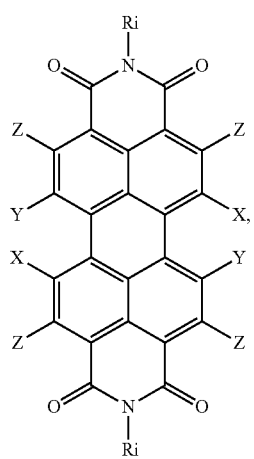

wherein W in formulae XXIII-XXV is selected from one of the following groups:

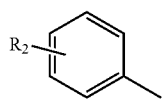 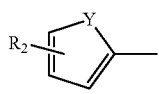 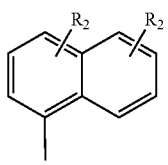

wherein Y as used in formula W is selected from the group consisting of $CH_2$, S, O, Se and $N-R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group $-O-R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, particularly, $R_2$ has not more than 6 carbon atoms;

wherein X and Y in formulae XXIII-XXV are independently selected from the following groups:

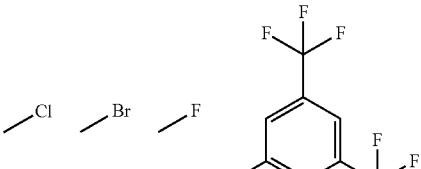

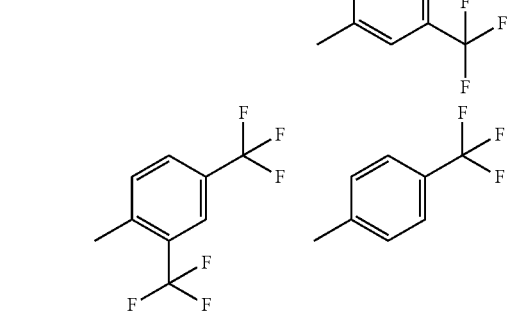

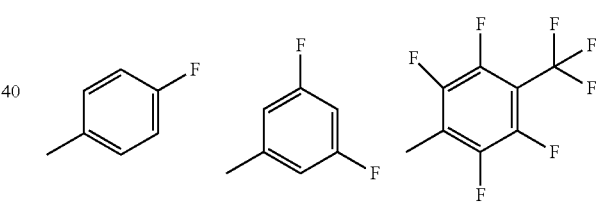

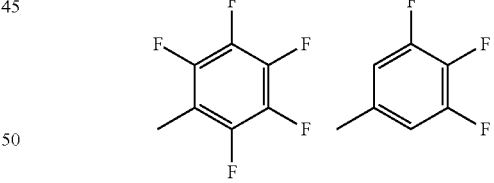

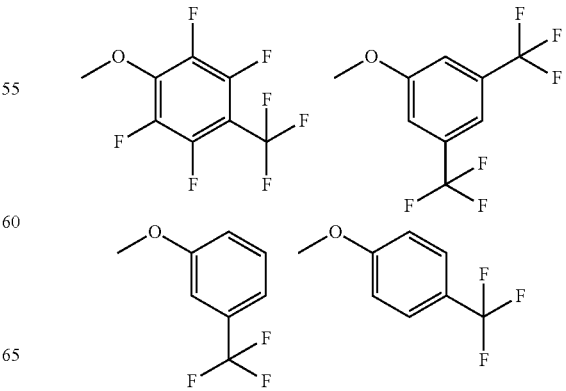

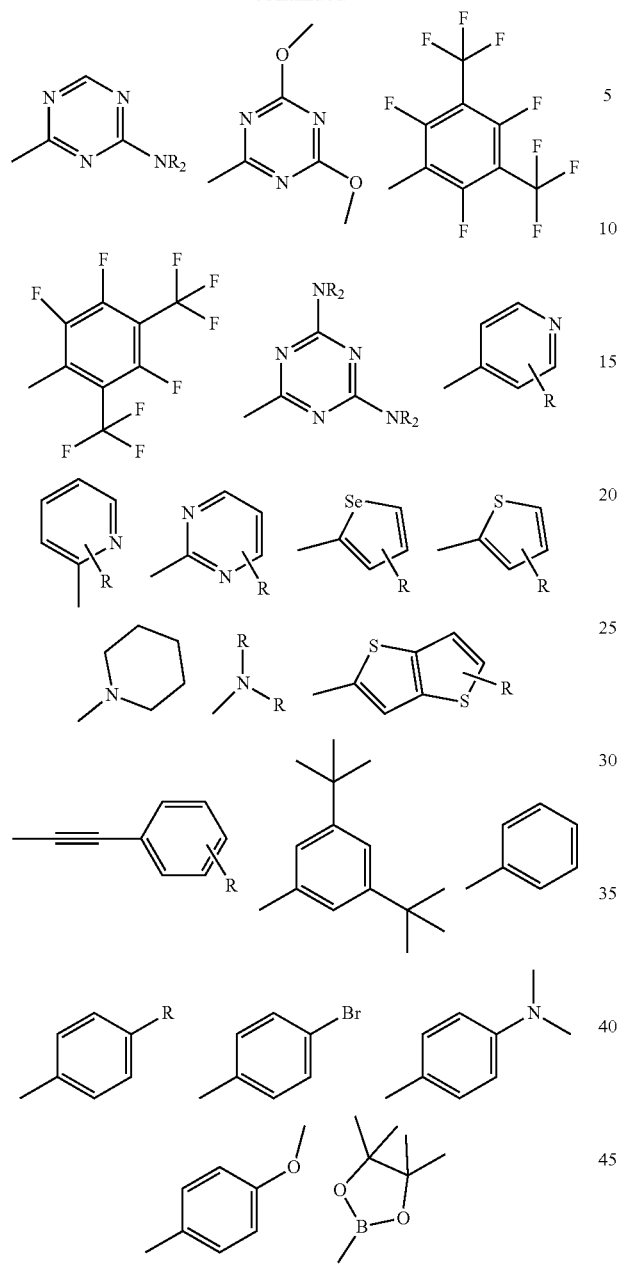

and wherein R is selected from the group consisting of H, a linear alkyl group, a branched alkyl group, a cycloalkyl group, a halogenated alky group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, particularly, R has not more than 6 carbon atoms, wherein Z in formulae XXIII-XXV is selected from the following groups:

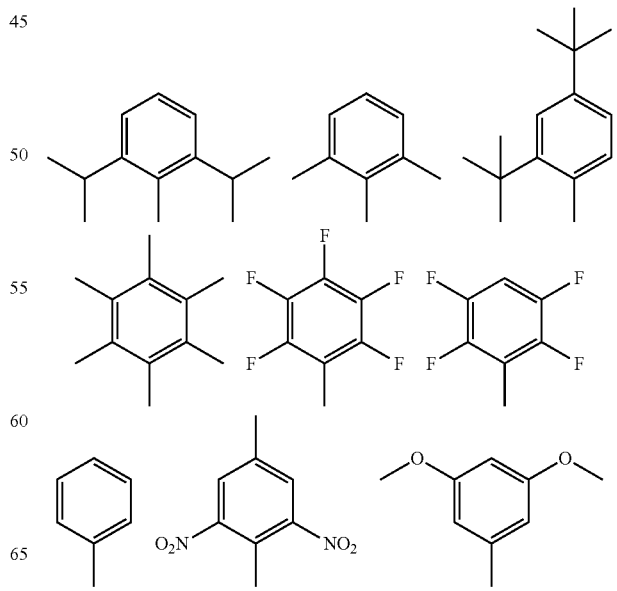

and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, in particular, $R_2$ has not more than 6 carbon atoms, wherein Ri is selected from the following groups:

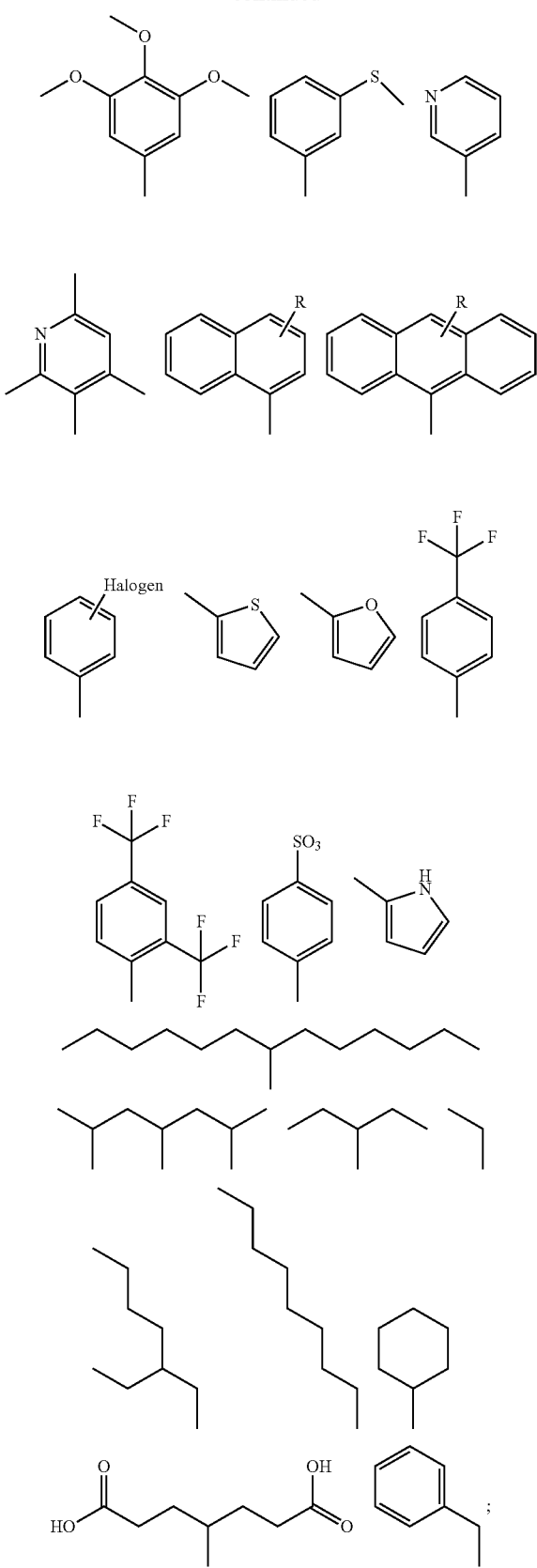
wherein, particularly, W is selected from the following groups:

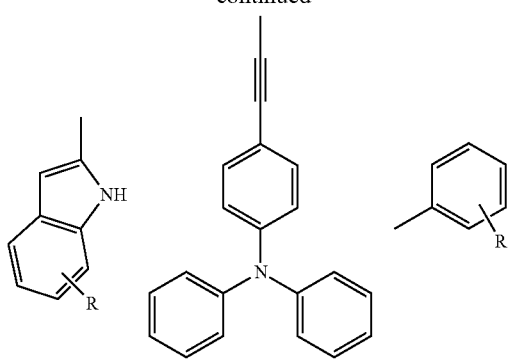
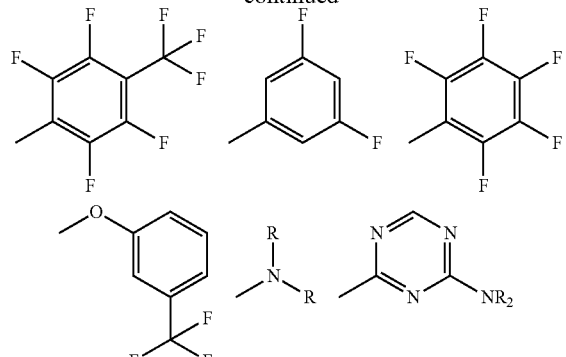
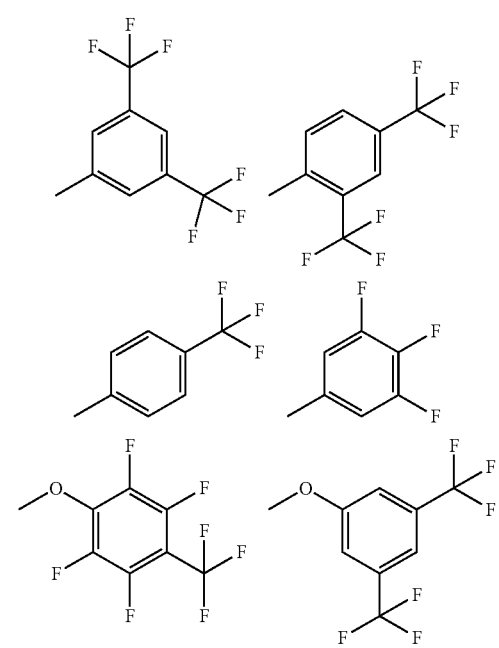
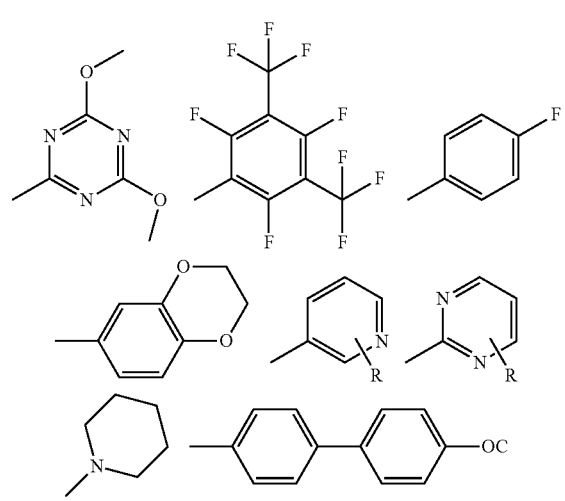
With R, $R_i$, $R_2$ being as defined above;
or wherein said at least one light emitter has a structure selected from one of the following:
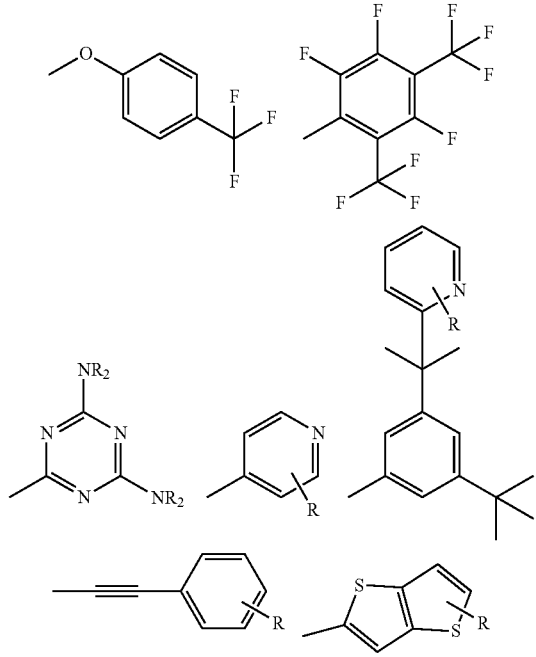
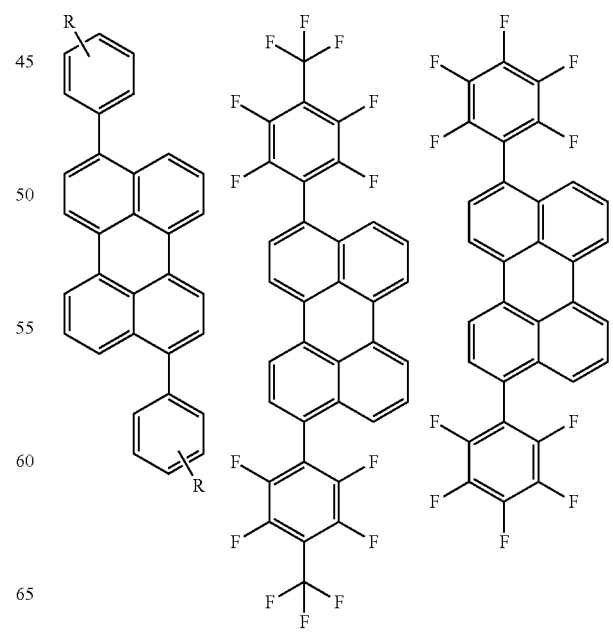

-continued

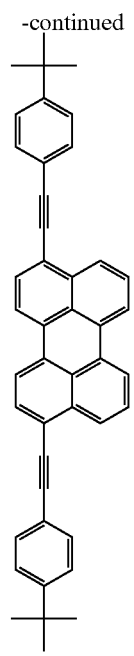

wherein R is a linear or branched alkyl group, particularly with not more than 6 carbon atoms;
or wherein said light emitter has the structure represented by Formula (XXVI) or includes a molecule having the structure represented by Formula (XXVI):

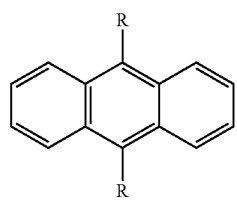

Formula (XXVI)

wherein R is selected from the following groups:

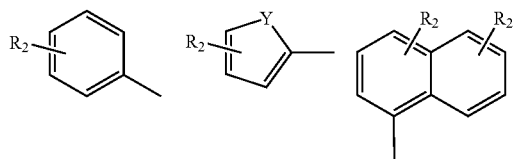

wherein Y is selected from the group consisting of $CH_2$, S, O, Se and N—$R_2$, and wherein $R_2$ is selected from the group consisting of H, a linear alkyl group, a branched alkyl group, a cycloalkyl group, a halogenated alky group, a halogen atom, an alkyl sulfanyl group, an aryl sulfanyl group, an amino alkyl group, an amino aryl group, an aryl group, a heteroaryl group, a fluorenyl group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, particularly, $R_2$ has not more than 6 carbon atoms;

or wherein R is selected from the following groups:

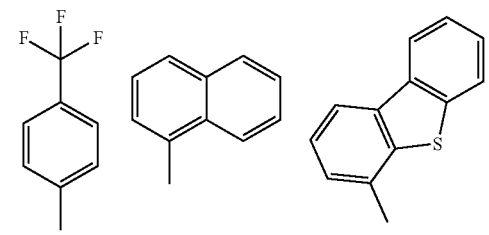

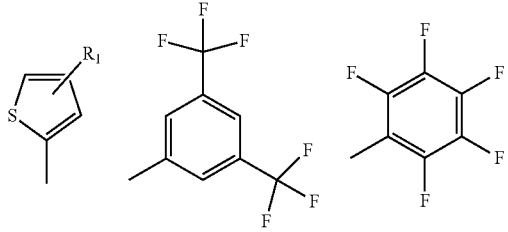

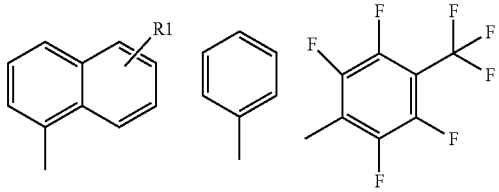

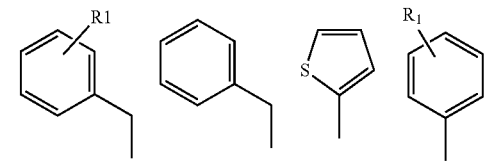

wherein $R_1$ is a linear or branched alkyl group, particularly with not more than 6 carbon atoms;

or wherein said at least one light emitter has a structure selected from one of the following or includes a molecule having a structure selected from one of the following:

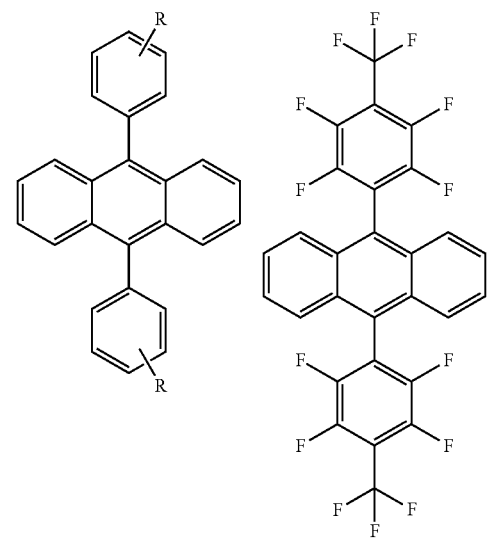

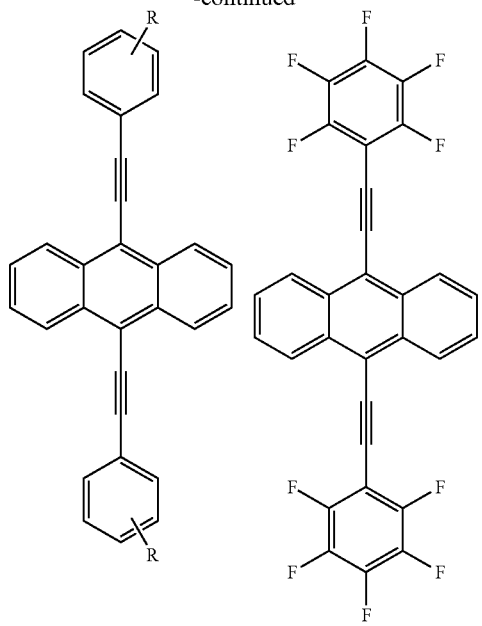

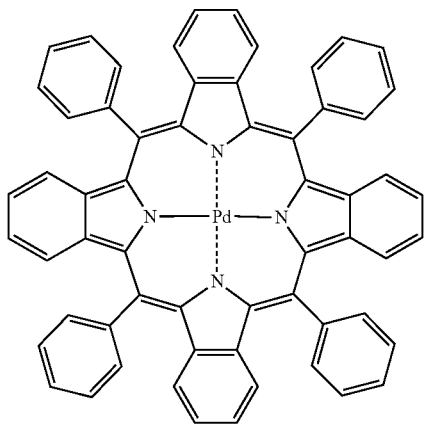

Formula (XXVIII)

wherein R is a linear or branched alkyl group, particularly with up to 6 carbon atoms.

7. The nanoparticle according to any of embodiments 5 and 6, wherein said at least one sensitizer is or includes a porphyrin or a phthalocyanine, wherein, in particular, said at least one sensitizer has a structure represented by Formula (XXVII), Formula (XXVIII), Formula (IXXX), Formula (XXX) or Formula (XXXI) or includes a molecule having a structure represented by Formula (XXVIII), Formula (IXXX), Formula (XXX) or Formula (XXXI):

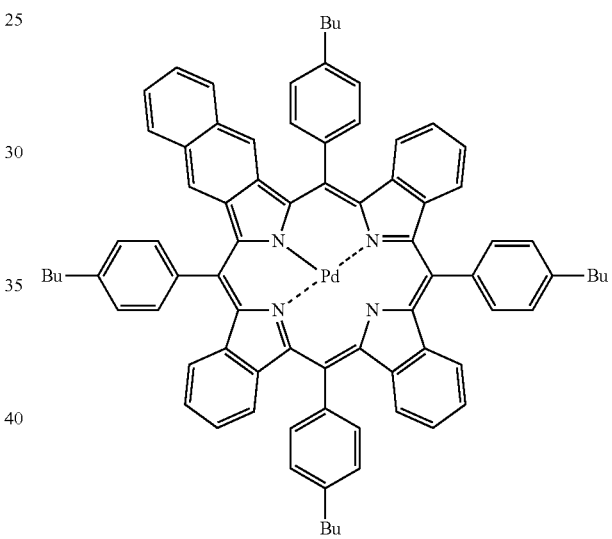

Formula (IXXX)

Formula (XXVII)

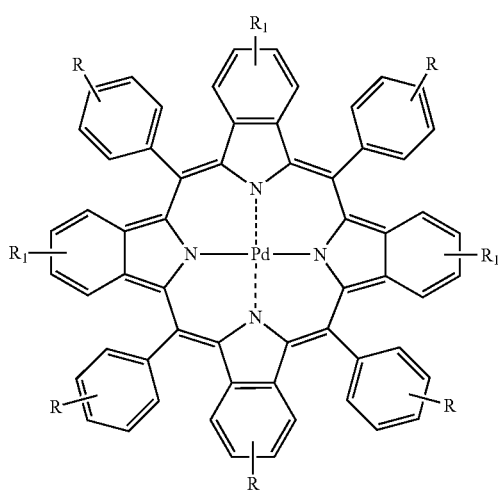

wherein $R_1$ is hydrogen, a linear or branched alkyl group, in particular with up to 6 carbon atoms, or a benzene ring, and wherein R is a linear or branched alkyl group, in particular with up to 6 carbon atoms;

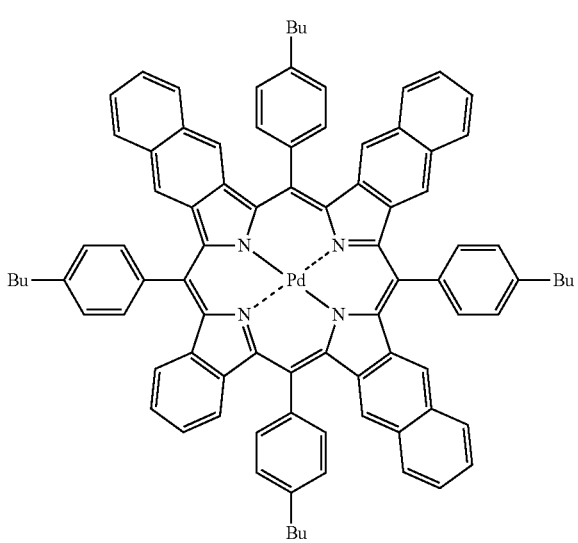

Formula (XXX)

-continued

Formula (XXXI)

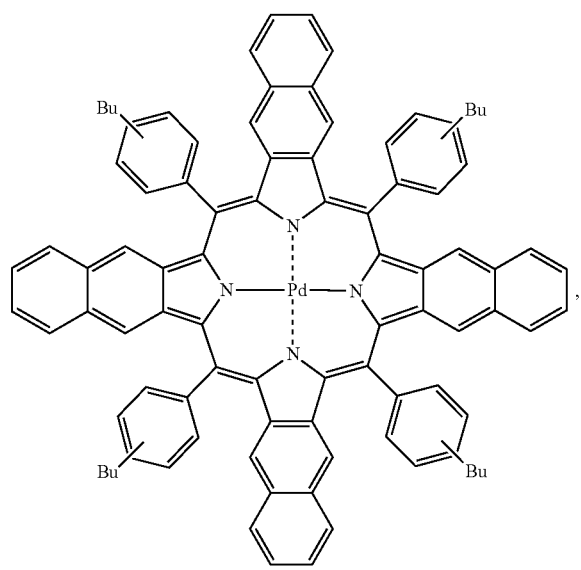

wherein, in particular, said sensitizer has the structure represented by Formula (XXVIII):

Formula (XXVIII)

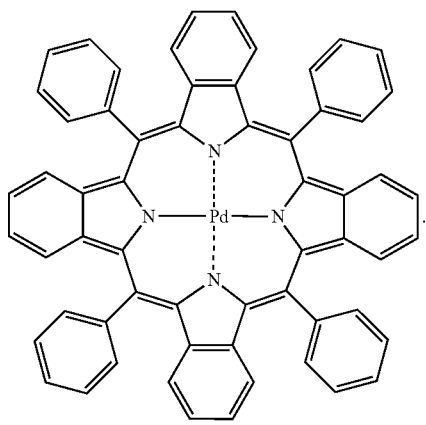

8. The nanoparticle according to any of the foregoing embodiments, wherein said nanoparticle (NP) includes 1 to 4 metal nanoparticles, and/or wherein said nanoparticle (NP) does not include metal nanoparticles that are in contact with each other.

9. The nanoparticle according to any of the foregoing embodiments, wherein said at least one metal nanoparticle has a diameter in the range of from 1 to 100 nm, in particular in the range of from 10 to 100 nm, more particularly in the range of from 10 to 50 nm, and/or wherein said at least one metal nanoparticle consists of a material selected from the group consisting of Ag, Au and Co, and/or wherein said metal nanoparticle(s) is(are) plasmonic and/or magnetic.

10. The nanoparticle according to any of the foregoing embodiments, wherein said nanoparticle further includes at least one antioxidant, in particular a singlet oxygen scavenger or reactive oxygen scavenger (ROS), particularly a singlet oxygen scavenger/quencher, wherein, in particular, said at least one antioxidant is selected from the group consisting of lipoic acid, vitamin E, a carotenoid, ascorbic acid derivatives soluble in organic solvents, particularly an ascorbic acid palmitate.

11. The nanoparticle according to any of the foregoing embodiments, wherein said nanoparticle includes functional groups at its surface that allow to covalently couple a molecule to the nanoparticle, wherein, in particular, said functional groups are selected from the group consisting of —COOH (carboxylate), —NH$_2$, —SH (thiol), —NHS, alkynyl, —N$_3$, aldehyde, ketone and biotin group, wherein, more particularly, said functional groups are —COOH and/or —NH$_2$.

12. The nanoparticle according to any of the foregoing embodiments, wherein said nanoparticle includes molecules or chemical groups attached to its surface that are capable of specifically binding to an analyte molecule or that have an enzymatic activity that allows to detect an analyte molecule, wherein, in particular, said molecules attached to the surface of the nanoparticle are antibody molecules, and wherein, in particular, said analyte molecule is a biomolecule.

13. A sensing layer including nanoparticles as defined in any of the foregoing embodiments.

14. A method of producing nanoparticles (NP) as defined in any of embodiments 1-13, said nanoparticles (NP) including
a polymeric organic matrix,
at least one light emitter distributed within said matrix,
optionally at least one sensitizer and/or at least one antioxidant distributed within said matrix,
a stabilizing agent, and
at least one metal nanoparticle enclosed within said matrix,
wherein said at least one metal nanoparticle is a plasmonic nanoparticle, said method including the steps of:
providing a polymer or combination of polymers or combination of polymers with small molecules from which the polymeric organic matrix is to be formed, a stabilizing agent, at least one light emitter, plasmonic metal nanoparticles, and optionally at least one sensitizer and/or at least one antioxidant,
preparing a dispersion of said plasmonic metal nanoparticles in an organic water-miscible solvent, particularly upon ligand exchange of said plasmonic metal nanoparticles,
preparing a mixture of said polymer or combination of polymers or combination of polymers with small molecules from which the polymeric organic matrix is to be formed, said stabilizing agent, said light emitter(s) and optionally said sensitizer(s) and/or said antioxidant in an organic water-miscible solvent,
adding said mixture of said polymer or combination of polymers or combination of polymers with small molecules, said stabilizing agent, said light emitter(s) and optionally said sensitizer(s) and/or said antioxidant(s) to said dispersion of metal nanoparticles or vice versa, thus forming a mixture including said metal nanoparticles,
inducing said mixture including said plasmonic metal nanoparticles to form nanoparticles (NP), thus forming a dispersion of nanoparticles (NP) wherein said nanoparticles (NP) include a polymeric organic matrix with said light emitter(s) and, optionally, said sensitizer(s) and/or said antioxidant(s), distributed therein, and wherein said metal nanoparticles are enclosed in said polymeric organic matrix.

15. Use of nanoparticles according to any of embodiments 1-13 in a biological application selected from the group consisting of labeling and/or detection of cells, biological (macro-)molecules or other analytes, fluorescence microscopy, (flow) cytometry, fluorescence-activated cell sorting (FACS), fluorescence resonance energy transfer (FRET), immunohistochemistry, clinical immunoassays, fluorescence-quenching-based enzyme-activity assays, high-throughput screening, molecular diagnostics, sensing of temperature, sensing of pressure and sensing of oxygen.

EXAMPLES

Example 1

Preparation of Nanoparticles

This example describes the optimised production of examples of multicomponent nanoparticles in accordance with the present disclosure. These special, original designed nanoparticles are prepared by rapidly mixing water into a cooled, stirring, solution of an optimised organic matrix, optimised surface stabiliser or dispersant, dyes—including specially developed hydrophobic dyes with even more efficient incorporation) an emitter and a sensitizer in dry THF under an inert atmosphere. In addition to the organic components, silver nanoparticles can be added to the organic phase before mixing. The procedure and the components of the nanoparticles were optimized for sensitivity, increase in upconversion signal and size, which also effects transparency of the solution.

The size and size distribution of the nanoparticles produced in this method is very good if the aqueous phase and organic phase are chilled and mixed very rapidly. To accomplish this two electronically controlled valves, that quickly move from fully closed to fully open in under 0.2 s are used. A partial vacuum of 30 mbar in the mixing chamber also facilitates the very fast addition of the aqueous phase to the organic phase. This, along with rapid stirring of the solution, allows a colloidal solution to be formed upon the water addition. The dispersion was then stirred under inert atmosphere for over an hour and the organic solvent evaporated under reduced pressure. Following cooling overnight the dispersion was filtered to remove large masses, and centrifuged within a concentrator tube remove small molecules and aggregates and collect the organic particles. Nanoparticles were collected in water (2 ml or 0.5 ml) and stored at 4° C.

What is described in this example is a representative procedure.

Purpose/Aim:
This example details a method for the controlled, repeatable, formation of nanoparticles with consistent size and polydispersity index (PDI). This procedure was developed to yield methods, which allows for the inclusion of fluorescent dye(s), or upconversion systems (sensitizers & emitters) into the nanoparticles—especially as aqueous dispersions.

Figure 1:
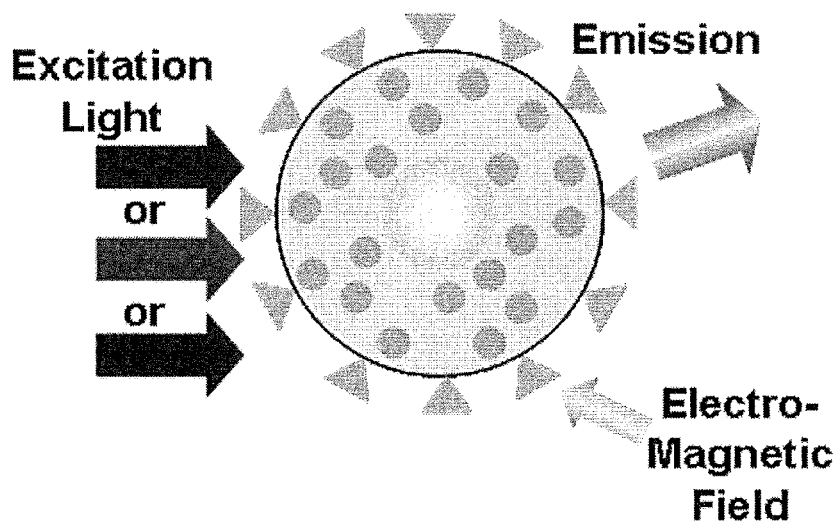
FIG. 1 shows examples of nanoparticles according to the present disclosure. (A) Luminescent organic nanoparticles. Emitters could be singlet or triplet emitters, or a combination thereof. The circles shown in different shades of grey illustrate different types of emitters as also shown in the text. The different shades of grey mean that the emitters can have variable absorption/emission wavelengths as described in the embodiments/claims. (B) Luminescent organic nanoparticles for photon upconversion. An emitter and a sensitizer are included. The darkest grey circles are the sensitizer molecules. Also these sensitizers can have variable absorption wavelengths as described in the embodiments/claims. Again, for the emitters which are shown in differently shaded lighter grey circles, the different shades of grey mean that the emitters can have variable absorption/emission wavelengths as described in the embodiments/claims. Both in A and B in the center of the nanoparticle, there is the enhancing plasmonic nanoparticle; additionally, the matrix can contain an antioxidant.
Figure 1:
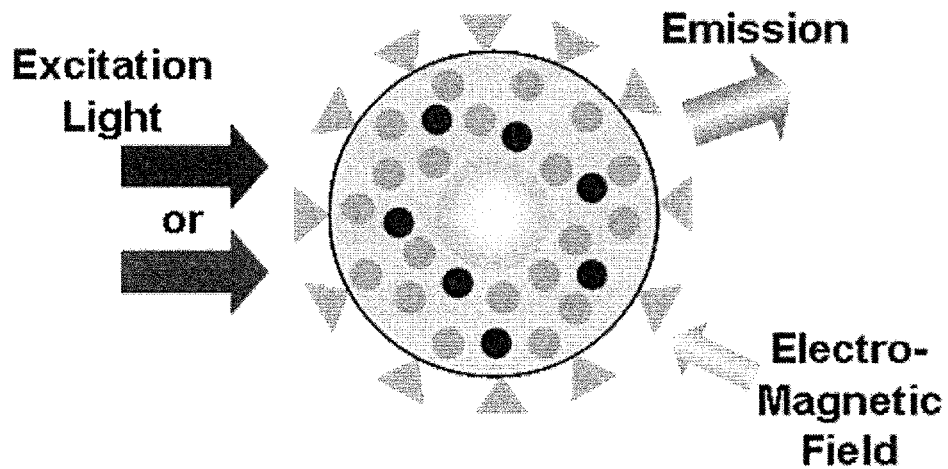
Figure 4:
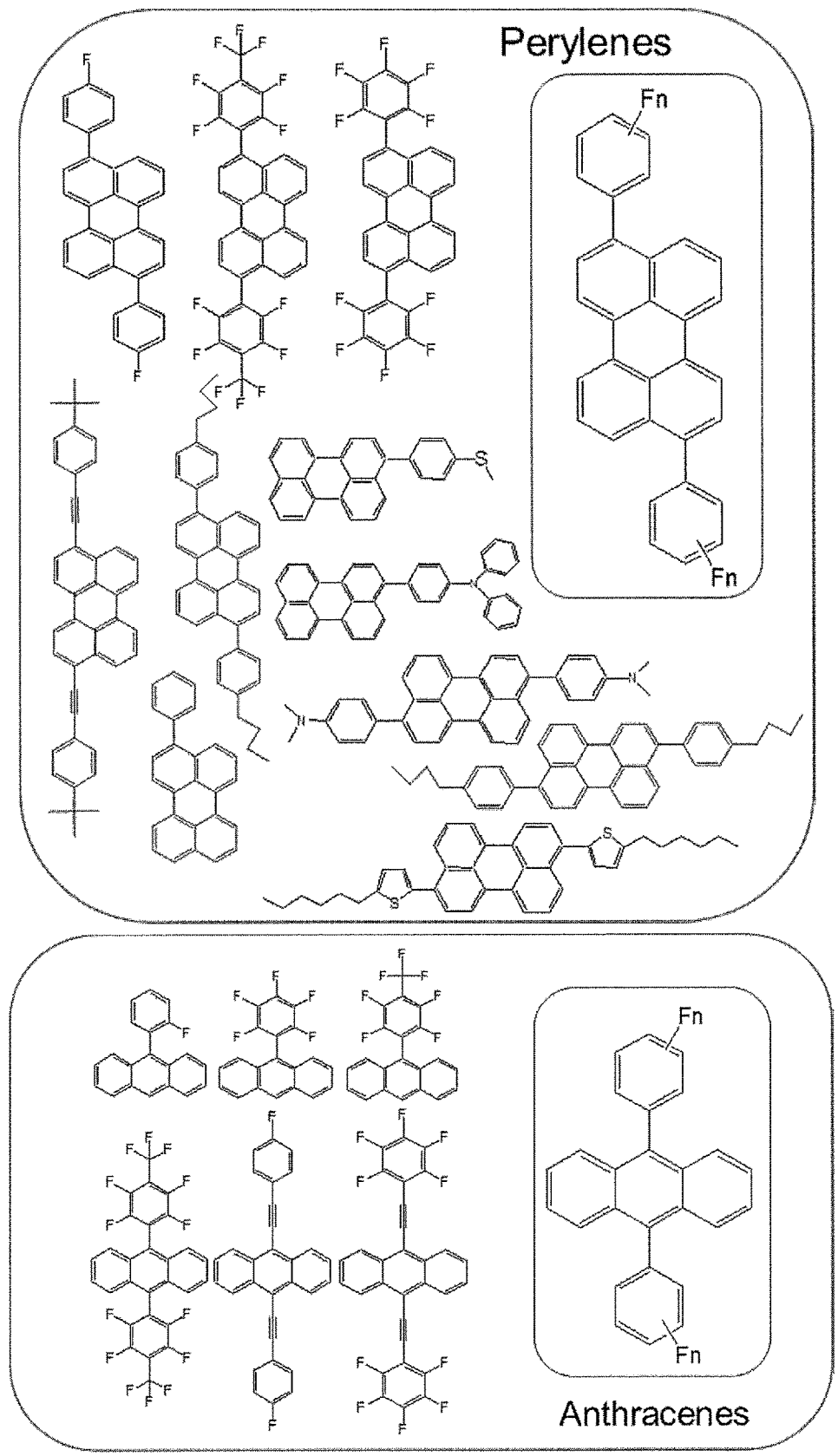
FIG. 4 shows examples for light emitters suitable for use in nanoparticles according to the present disclosure.
Figure 5:
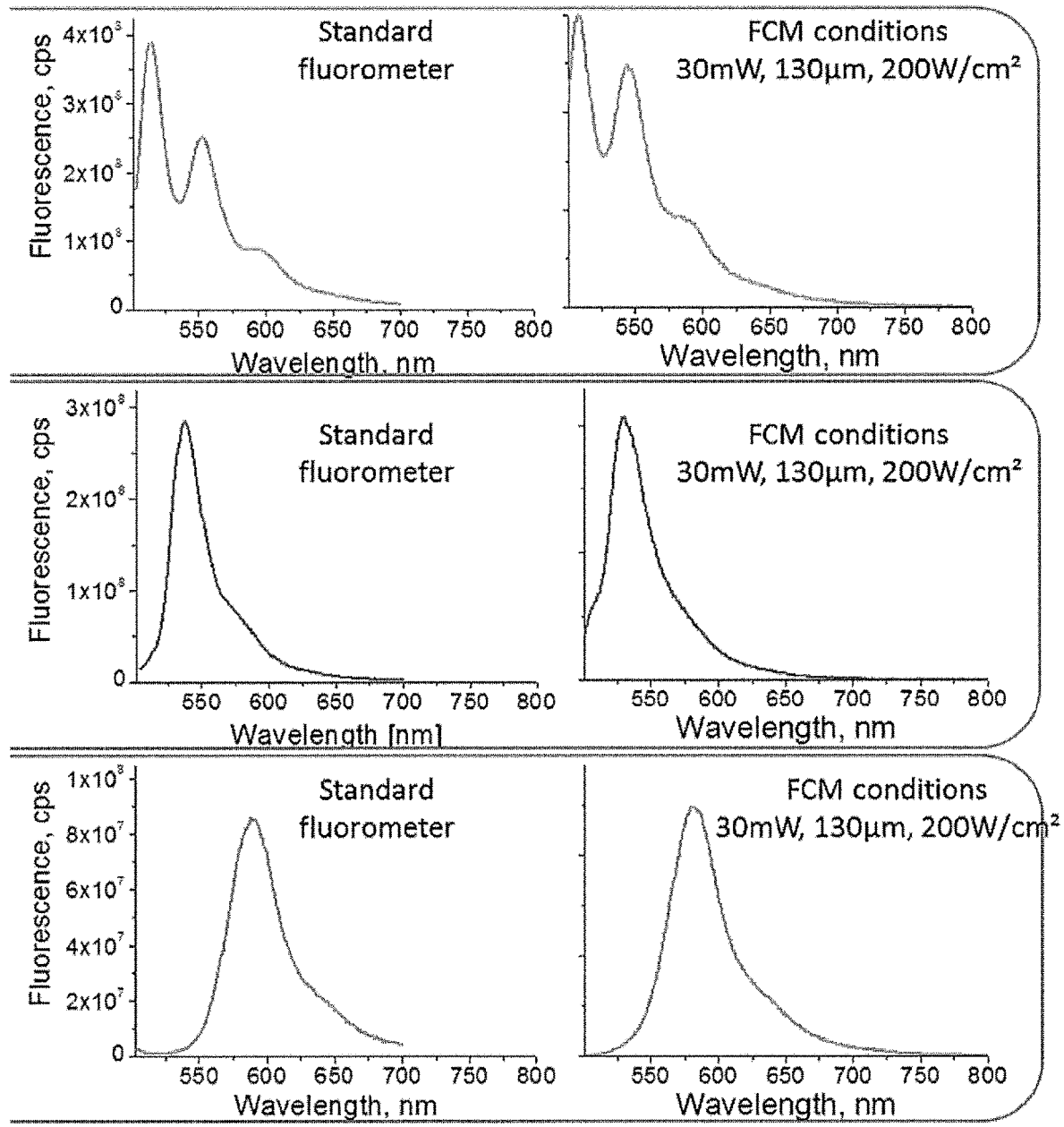
FIG. 5 shows examples of emission spectra and maximum wavelengths in nanoparticles with different light emitter/sensitizer/metal nanoparticle combinations. The graphs on the left side are the spectra as measured by standard fluorometer (with a big spot of ca few $mm^2$ area, low excitation intensity). The graphs on the right side are the spectra as measured in flow cytometry relevant (FCM) conditions (i.e. a small spot, ca. 130 μm diameter, 30 mW or 200/W/cm2 excitation intensity).

The applications of such dye-loaded nanoparticles are diverse (including fluorescence, or PUC, or both in combination), for example:
To manufacture bright, stable, with controllable size emissive nanoparticles in aqueous dispersions—for application as labels for e.g. proteins and cells. In a similar manner the water soluble dyes are used.
For direct uptake by cells—imaging of live cells or their flow cytomteric investigations (following the uptake of the NPs by the cells)
For attachment to cells surface—flow cytometry/sorting—after the NPs are attached on the cell surface (here polystyrene (PS) microparticles are used in the examples as cell model)
The formation of sensing/imaging layers, e.g. in the development of a sensing layer which can be (is) used in combination with neuronal cell cultures as non-invasive neuroimaging system for the visualization of neuronal activities. To manufacture PUC-NPs to sense the NT dopamine or other NTs like serotonin, as well as other biomolecules which can scavange/quench singlet oxygen—as added to the NPs dispersion—as released by neuronal cells or from any other source.
To control the PUC outcome from the NPs as well as their incorporation in ESL—for control of sensitivity and dynamic range of ESL for dopamine sensing
Solution/Procedure (Experimental):
The main optimisation pathways of the NPs core:
Variation of the components:
Variation of the ratio/amount of the matrix components e.g. PMMA (polymethylmethacrylate) and PHD (heptadecyl benzene)
Variation of the surface stabilizer and its concentration
Variation also combinations of the emitter molecules and there concentration
Variation also combination of the sensitizer molecules also their concentration
Addition/variation also combinations of antioxidant(s) (singlet oxygen scavenger/quencher or ROS scavenger) and their concentration,
Variation of the mixing conditions
Air vs. inert atmosphere
Temperature of the organic solution and the water and as follows influence also the size and the surface potential of the nanoparticls as well as on their emissive/sensing properties and their further attachment/functionalisation properties.
The following procedure details the production of nanoparticles. Typically 4 to 6 variations (nanoparticles comprised of, for example, differing Ag nanoparticles and antioxidant concentration as shown in FIGS. 2 and 3) are typically prepared in one day. This method of preparing the nanoparticles is to inject cold water into an organic phase containing the matrix components, the stabiliser, the antioxidants (if any), the metal nanoparticles and the dye molecules. Then by adding water, quickly and with a large amount of agitation, to this phase nanoparticles of consistent size and polydispersity index (PDI) are produced in a controlled, repeatable manner for the corresponding combination of components.
Typical Materials:
Surface stabilizer: CoPEG (Glycolic acid ethoxylate 4-nonylphenyl ether)
Matrix: PHD(Heptadecylbenzene), and PMMA
Emitters: e.g. 3,10-Bis((4-tert-butylphenyl)ethynyl) perylene or 3,9-diphenyl-perylene Or 3,9-Bis-(4-butyl-phenyl)-perylene or further see FIG. 4 or all molecular structures Sensitizer: PdTBP
Organic Solvent: THF
Additional Nanoparticles 4 nm AgNP in 1 mg/ml THF
Antioxidant: 6-O-Palmitoyl-L-ascorbic acid or lipoic acid, or other (see the description above),
The general components of exemplary nanoparticles in accordance with the present disclosure are depicted in FIG. 1. See FIG. 1A—for luminescent, e.g. fluorescent NPs, and FIG. 1B for photon upconversion nanoparticles (PUC NPs).

Results on size and polydispersity (briefly):
Typical results are shown in the table below.

|  | NP1 | NP2 |
|---|---|---|
| Silver Nanoparticles added | No | Yes |
| Average Size/nm | 126 ± 1 | 144 ± 1 |
| PDI | 0.20± | 0.22± |
| Zeta Potential/mv (neutral | −51.5 ± 0.7 | −54.8 ± 0.8 |
| Conductivity (µS/cm) | 11.3 ± 2.4 | 8.7 ± 0.04 |
| Mobility (µmcm/Vs) | −4.0 ± −0.1 | −4.3 ± 0.1 |

The polydispersity index (PDI) is a measure of the size consistency of the nanoparticles. For nanoparticle batches prepared via this method, the PDI is around 0.2, which is good. The Zeta potential is a measure of colloidal stability. The Zeta potential is calculated from the measured conductivity of the solution, and the mobility of the particles. In general Zeta potential values of a magnitude greater than 40 mV are indicative of a stable colloid, furthermore, values above 60 mV are indicative of excellent stability. Typically, for nanoparticles prepared via this method the Zeta potential is ~50 mV this indicated that these colloidal solutions are not likely to aggregate. Upon further optimisation of the NPs components and their ration up to −65 mV were achieved.

As an example of stability, the nanoparticles were measured for size distribution following storage for 5 days to check their stability and degree of aggregation—there was no change beyond that within the region of the error of the measurement, indicating stable nanoparticles.

|  | Average size difference/nm | PDI difference |
|---|---|---|
| NP1 | 4.68 ± 3.00 | 0.0288 ± 0.0212 |
| NP2 | 1.82 ± 2.90 | −0.0077 ± 0.0076 |

Exemplary Nanoparticle Preparation Method Overview Summary:

Nanoparticles are prepared in this method by firing water [e.g. MilliQ, with controlled temperature and high speed (through electronic valves) into a temperature controlled, stirring solution of an organic phase [e.g. glycolic acid, heptadecylbenzene, polymethylmethacrylate, and Pd tetrabenzoporphyrin (PdTBP) sensitizer in dry THF under an inert $N_2$ atmosphere. Silver nanoparticles, [e.g. 4 nm Ag-Dodecanethiole NP or 50 nm SiO2 capped Ag nanoparticles are compared in FIG. 9] and antioxidant (e.g. lipoic acid in 2 different concentrations is shown in FIG. 9) can be added to the organic phase before mixing. The dispersion was then stirred under inert atmosphere for over an hour and the organic solvent (THF) evaporated under reduced pressure. The dispersion was filtered (Whatman 1 filter paper) to remove and large masses, and then centrifuged (100 K MWCO Corning Spin-X UF Concentrator 20 ml, to remove small molecules and particles. Nanoparticles of interest were collected in MilliQ water and stored cool (4° C.). This yields stable nanoparticles with a good polydispersity index (e.g. 0.2) and good zeta potential (e.g. −50 mV or higher).

Conclusion:

Organic nanoparticles with reproducible, controllable, repeatable size and optimised size distribution are successfully prepared via this method. Dyes and smaller nanoparticles have been successfully incorporated into the nanoparticles.

A protocol for NP synthesis was developed and optimized step by step. The set-up for the optimised procedure incorporates pressure and temperature control as well as fast speed mixing valves. Nanoprobes with completely reproducible and controlled variable properties (e.g. size and surface potential) were synthesized with the given set-up.

The nanoparticle dispersions developed by this method are highly emissive, biocompatible and can be used in a variety of biotechnological applications, especially for flow cytometry, live cell imaging, or—live cell functions imaging—e.g. neurotransmitters (or antioxidants) visualisation/imaging in neuronal or any other tissue or cell culture and/or as released by neuronal cells Example 2

Preparation of an Example of a Sensor Comprising an Emissive Sensing Layer

Here an exemplary method is presented to produce transparent emissive sensing layers (ESLs) composed of emissive nanoparticles as prepared in accordance with the present disclosure, i.e. photon upconversion nanoparticles (PUC NPs) embedded into a polymer matrix. The ESLs aim for the quantitative detection of different biomolecules secreted from living cells in cell culture with high spatiotemporal resolution. To achieve these goals the layers necessitate to exhibit excellent homogeneity, good stability under cell culture conditions as well as a high sensitivity and selectivity towards the target molecules.

This example describes an optimization of the sensing layer. Especially the homogeneity and the upconversion (UC) signal achieved by the layers in this example are very good. Additionally, stiffness of the layers can be tuned easily. The optimization includes change from a biopolymer matrix towards an organic polymer matrix. FIG. 10 shows the general structure and composition of an embodiment of an ESL, in particular a schematic drawing showing the general composition and structure of an emissive sensing layer (ESL). The ESL is prepared on a modified glass support and is afterwards functionalized with extracellular matrix proteins (ECM matrix proteins), such as collagen which facilitate biocompatibility of the layers.

Purpose/Aim:

The overall target is to develop a non-invasive tool to image cellular functions such as neurotransmitter release from neuronal cells (also in response to stimulation in real-time) using a standard epifluorescence microscopic setup. The layers are optimized for the use with neuronal cell models like PC-12 cells or human induced pluripotent stem cells. To achieve detection of target molecules from living cells the layers need to be permeable for the target molecules and in close proximity to the side of release. Furthermore the layers need to be stable for the duration of the cell culture.

Solution/Procedure (Experimental):

1. Procedure:

For optimization of ESLs an organic polymer matrix of polyacrylamide was used. This polymer forms an elastic hydrogel and can be varied in stiffness, which could also be of interest for cell culture applications. Polyacrylamide is used for cell culture applications like traction force microscopy. A detailed structure of the ESL and its components is shown in FIG. 10 which shows a schematic drawing showing the composition and structure of an emissive sensing layer (ESL).

1.1 Preparation of Activated Aminosilane-Coated Glass Slides:

To achieve attachment of the ESL to the glass support, the glass support is chemically modified. Aminofunctionalized glass slides (e.g NEXTERION A+, Schott GmbH, Jena) are used here as a starting point. Further activation is done by glutaraldehyde.

Preparation of hydrophobic coverslips:

Hydrophobic coverslips are needed to cover the polymerizing gel solution on the activated aminosilane-coated coverslips to prevent oxygen diffusion into the solution, which prevents polymerization and to achieve a flat surface of the final gel. Making the coverslips hydrophobic makes it easier to remove the glass slips after polymerization and helps to avoid damage to the gel. Different standard procedures for hydrophobisation can be used, e.g. using RainX.

1.2 Preparation of Gel:

To prepare the ESL solution one needs the PUC NPs, the enhancer (Plasmonic) nanoparticles (Ag or Au nanoparticles) and polyacrylamide (PAA) gel stock solution. The stock solution can be prepared in different acrylamide/bisacrylamide solutions to adapt gel stiffness and density. The mixtures, which have been used, are summarized in the below table. Further mixtures can be found in Plotnikov et al. (Plotnikov et al., Methods in Cell Biology, 2014; "High-resolution Traction Force Microscopy" in Methods in Cell Biology, Volume 123, 2014, ISSN 0091-679X)

TABLE

| Mixtures of PAA gel stock solutions | | |
|---|---|---|
| Component | 4 kPa stock solution | 30 kPa stock solution |
| Acrylamide 40% | 3.75 ml | 3 ml |
| Bisacrylamid 2% | 0.75 ml | 1.4 ml |
| MilliQ | 0.50 ml | 0.60 ml |
| Total volume | 5.00 ml | 5.00 ml |

The PAA gel stock solution can be stored at 4° C. for at least a year.

In a first step, Ag NPs (40 nm, plasmonic nanoparticles) are added to PUC NP solution in an 1.5 ml Eppendorf cup under sterile conditions. Then, PAA gel stock solution are added to the NP mixture and the complete solution is degassed either under argon or nitrogen atmosphere for 1 h. Furthermore, a 4% (w/w) ammonium-peroxosulfate (APS) solution is prepared in MilliQ. When everything is ready prepared, polymerization is induced by addition of TEMED and APS solution. The solution is quickly mixed using the 100 μl pipette and the gel solution is added per well as a small droplet on the surface of an 8-well sticky slide on an activated aminosilane-coated glass slide. The droplet is quickly covered by a hydrophobic coverslip. The rest of the solution is used as a polymerization control. After 30 minutes of incubation at room temperature, polymerization is complete and the hydrophobic coverslips are removed carefully using a tweezer. The gels are washed 3 times with MilliQ before they are stored at 4° C.

Further modification of the ESL can be achieved by various measures, e.g. coating with e.g. polydopamine and ECM proteins. Details about functionalization procedures can be found in the parallel application concurrently filed with and copending with the present application under applicant's reference number S32783EP.

2. Results of ESLs (Briefly):

2.1 Emissive Sensing Layers: Phase Contrast, Fluorescence and Upconversion

The emissive sensing layers prepared according to the aforementioned protocol were tested for fluorescence intensity at 488 nm and also upconversion intensity at 638 nm illumination wavelength under standardized conditions. Tests were conducted at the MSL imaging platform (Zeiss Axiovert inverted microscope, HXP lamp, 10× (tiled images) or 40× objective). To acquire the upconversion of the ESL, the layers were incubated for 2 h under $N_2$-atmosphere at 37° C. to remove molecular oxygen.

2.2 Emissive Sensing Layers: Dopamine Sensing

The layers were also tested for their sensing capabilities towards the targeted neurotransmitter dopamine. The results are shown in the figures, in particular FIGS. 11-14. Dopamine hydrochloride solution was dissolved either in PBS or HBSS.

Conclusion:

To improve homogeneity and sensitivity of the ESL polyacrylamide was used as matrix component. Two different acrylamide/bisacrylamide ratios were tested and both resulted in ESL with improved homogeneity, upconversion signal and transparency. Also the stability of gels under standard cell culture conditions could be validated. The ESL preparation is highly reproducible. ESLs are also stable over 3 weeks of incubation under cell culture conditions (see FIG. 15 for 24 h and 2 weeks stability results). Dopamine could be detected at relevant concentrations in the μM range. To facilitate growth of cell cultures or iPS cells, layers are further functionalized.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, define, in part, the scope of the foregoing claim terminology such that no inventive subject matter is dedicated to the public.

The invention claimed is:

1. A nanoparticle, comprising:
   a polymeric organic matrix;
   at least one light emitter distributed within said matrix;
   a stabilizing agent; and
   at least one metal nanoparticle enclosed within said matrix,
   wherein said at least one metal nanoparticle is a plasmonic nanoparticle.

2. The nanoparticle according to claim 1, wherein said polymeric organic matrix comprises at least one material selected from the group consisting of a polyacrylonitrile, a polystyrene, an oligostyrene, a styrene copolymer, a styrene-butadiene copolymer, a polystyrene-based elastomer, a polyethylene, an oligoethylene, a polyphenylene, a polyphenylene dendrimer, a polypropylene, a polytetrafluoroethylene, an extended polytetrafluoroethylene, a polyacrylate, a polymethylmethacrylate, an ethylene-co-vinyl acetate, a polysiloxane, a polysiloxane copolymer, a substituted polysiloxane, a modified polysiloxanes, a polyether, a polyurethane, a polyether-urethane, a polyethylene terephthalate, a polysulphone, and a copolymer thereof.

3. The nanoparticle according to claim 1, wherein said light emitter that emits light by luminescence.

4. The nanoparticle according to claim 1, wherein said nanoparticle is a photon up-conversion nanoparticle.

5. The nanoparticle according to claim 1, further comprising:
at least one sensitizer that absorbs light at a first wavelength region $w \leq \lambda_1 \leq x$, and said at least one light emitter emits light at a second wavelength region $y \leq \lambda_2 \leq z$, where $\lambda_2 \leq \lambda_1$, upon absorption of light by said at least one sensitizer at said first wavelength region $w \leq \lambda_1 \leq x$, said at least one light emitter emits light at said second wavelength region $y \leq \lambda_2 \leq z$.

6. The nanoparticle according to claim 5, wherein said at least one sensitizer has a structure of Formula (XXVIII), Formula (XXVIII)

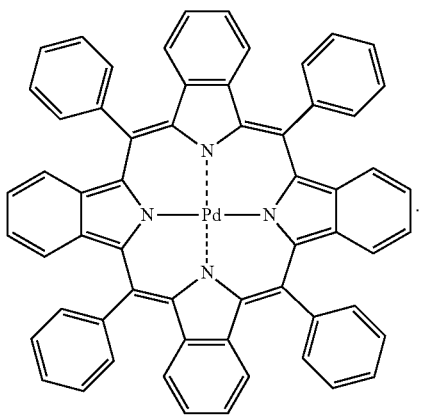

7. The nanoparticle according to claim 5, wherein said at least one sensitizer has a structure of Formula (XXVII), Formula (XXVIII), Formula (IXXX), Formula (XXX) or Formula (XXXI) or includes a molecule having the structure of Formula (XXVIII), Formula (IXXX), Formula (XXX) or Formula (XXXI), Formula (XXVII)

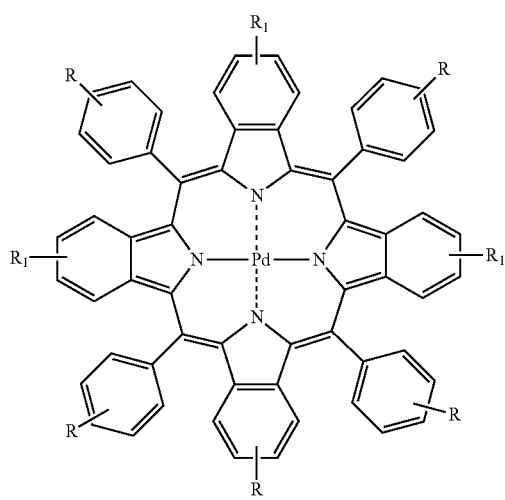

wherein $R_1$ is hydrogen, a linear or branched alkyl group, in particular with up to 6 carbon atoms, or a benzene ring, and wherein R is a linear or branched alkyl group, with up to 6 carbon atoms, Formula (XXVIII)

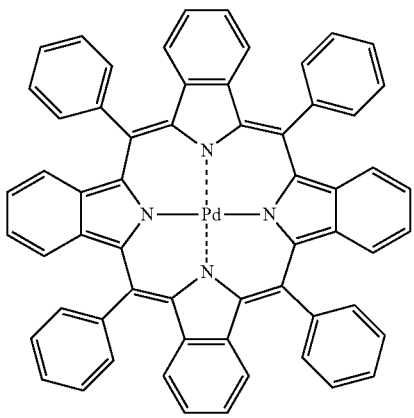

Formula (IXXX)

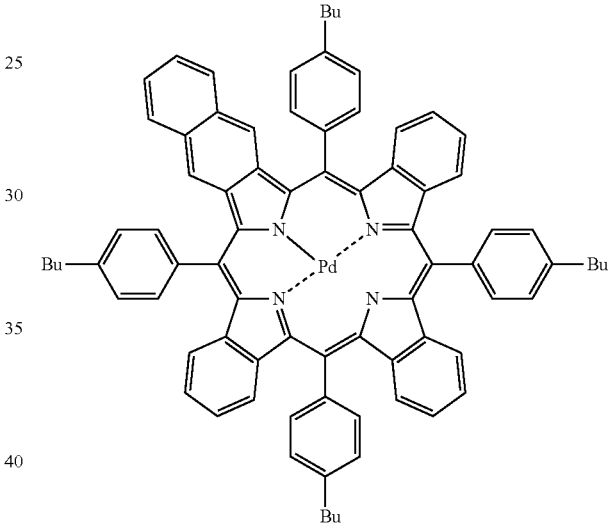

Formula (XXX)

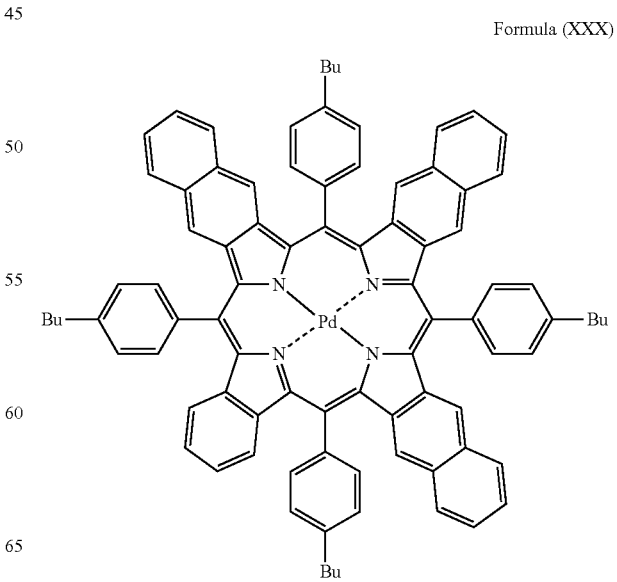

Formula (XXXI)

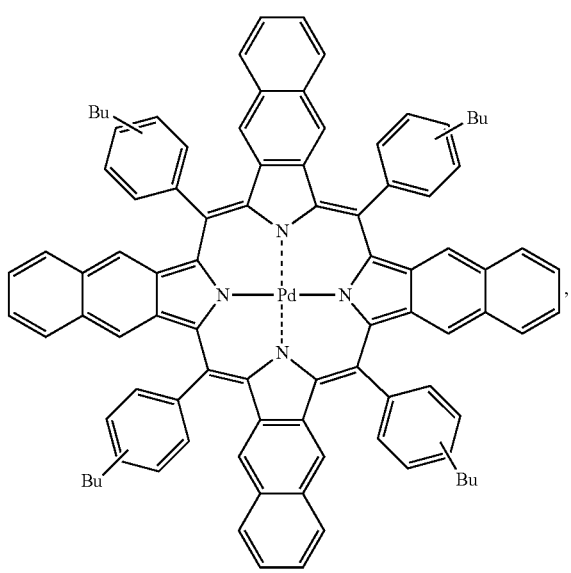

8. The nanoparticle according to claim 1, wherein said at least one light emitter is a molecule selected from the group consisting of an anthracene, a perylene, a perylene derivative, a coumarin and a BODIPY dye, said at least one light emitter has a structure of Formula (I) or (II) or includes a molecule having the structure of Formula (I) or (II), Formula (I)

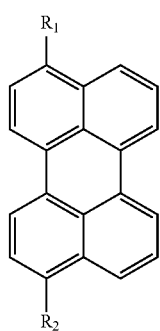

Formula (II)

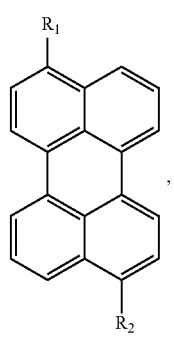

wherein $R_1$ and $R_2$ are independently selected from the group consisting of hydrogen and a moiety with a structure of Formula (III), at least one of $R_1$ and $R_2$ is a moiety with the structure of Formula (III), Formula (III)

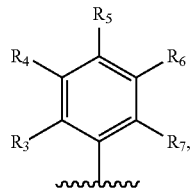

wherein $R_3$, $R_4$, $R_5$, $R_6$ and $R_7$ are independently selected from the group consisting of H, F, and tri-fluoro-methyl (—$CF_3$), and wherein at least one of $R_3$, $R_4$, $R_5$, $R_6$ and $R_7$ is F or tri-fluoro-methyl (—$CF_3$);

or wherein said at least one light emitter has a structure of Formula (X) or includes a molecule having the structure of Formula (X), Formula (X)

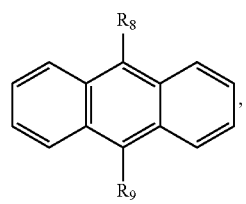

wherein $R_8$ and $R_9$ are independently selected from the group consisting of hydrogen and a moiety with a structure of Formula (XI), wherein at least one of $R_8$ and $R_9$ is a moiety with the structure of Formula (XI), Formula (XI)

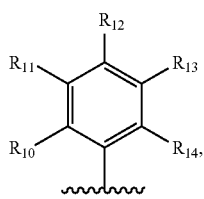

wherein $R_{10}$, $R_{11}$, $R_{12}$, $R_{13}$ and $R_{14}$ are independently selected from the group consisting of H, F, and tri-fluoro-methyl (—$CF_3$), and wherein at least one of $R_{10}$, $R_{11}$, $R_{12}$, $R_{13}$ and $R_{14}$ is F or tri-fluoro-methyl (—$CF_3$);

or wherein said at least one light emitter has one of structures or includes a molecule having one of the structures,

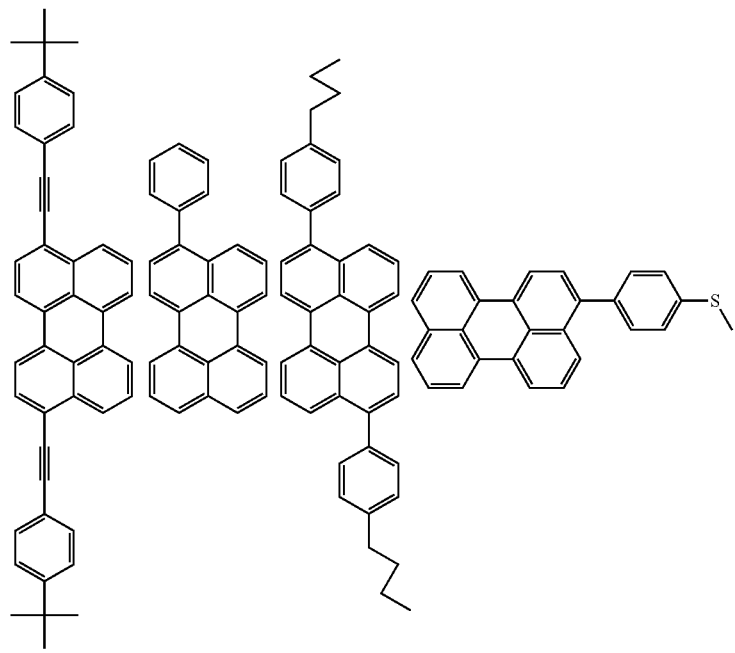
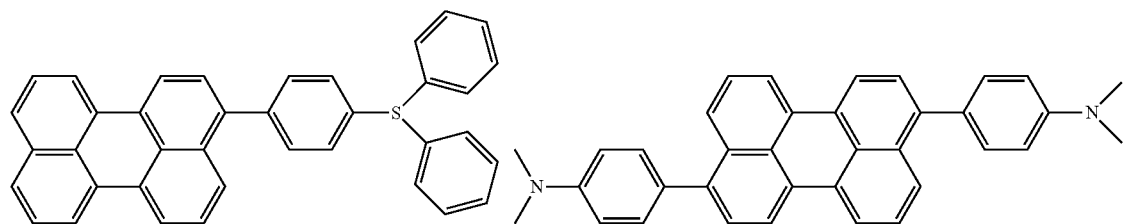
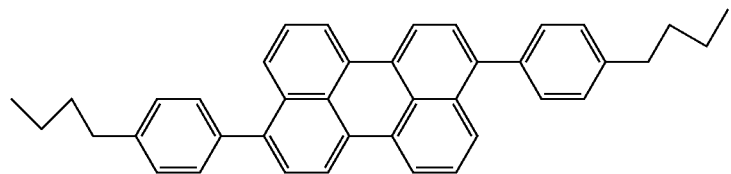
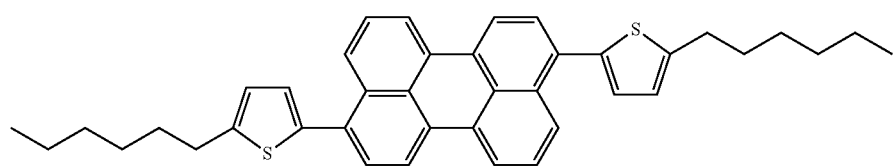

or wherein said light emitter has a structure of Formula (XXIII), (XXIV) or (XXV) or includes a molecule having the structure of Formula (XXIII), (XXIV) or (XXV), Formula (XXIII)

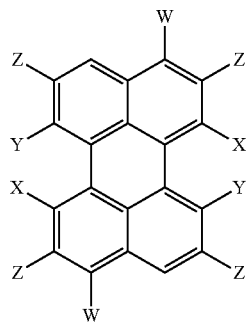

Formula (XXIV)

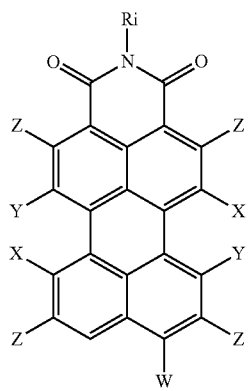

Formula (XXV)

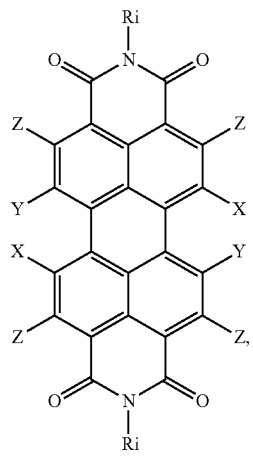

wherein W in Formulas (XXIII-XXV) is one selected from groups,

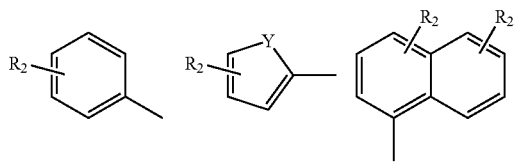

wherein Y as used in formula W is selected from the group consisting of $CH_2$, S, O, Se and N—$R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein X and Y in Formulas (XXIII-XXV) are independently selected from groups,

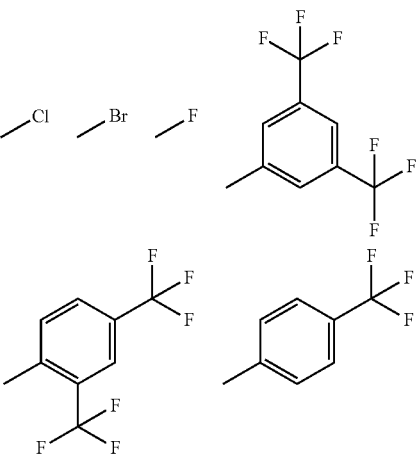

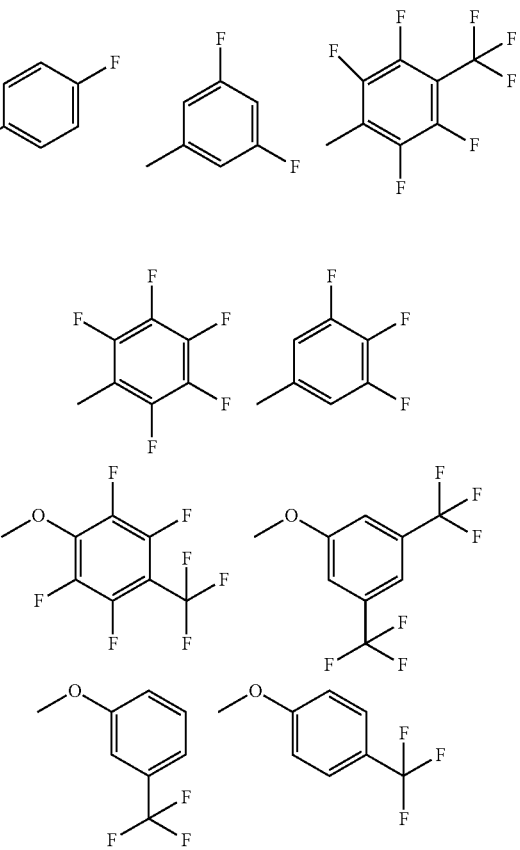

-continued

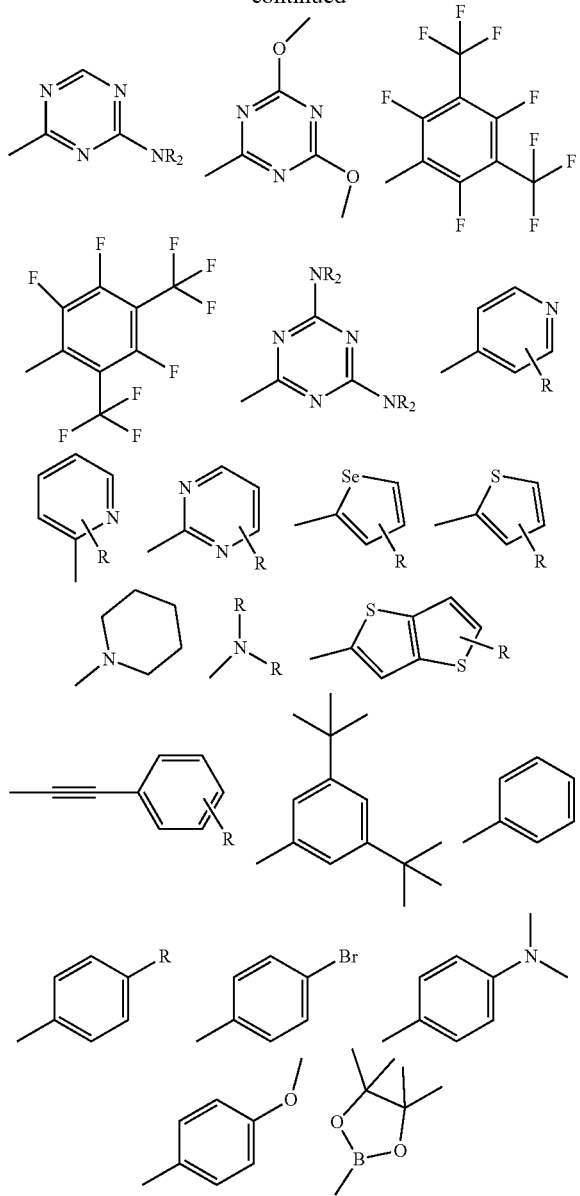

wherein R is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein Z in Formulas (XXIII-XXV) is selected from groups, -continued

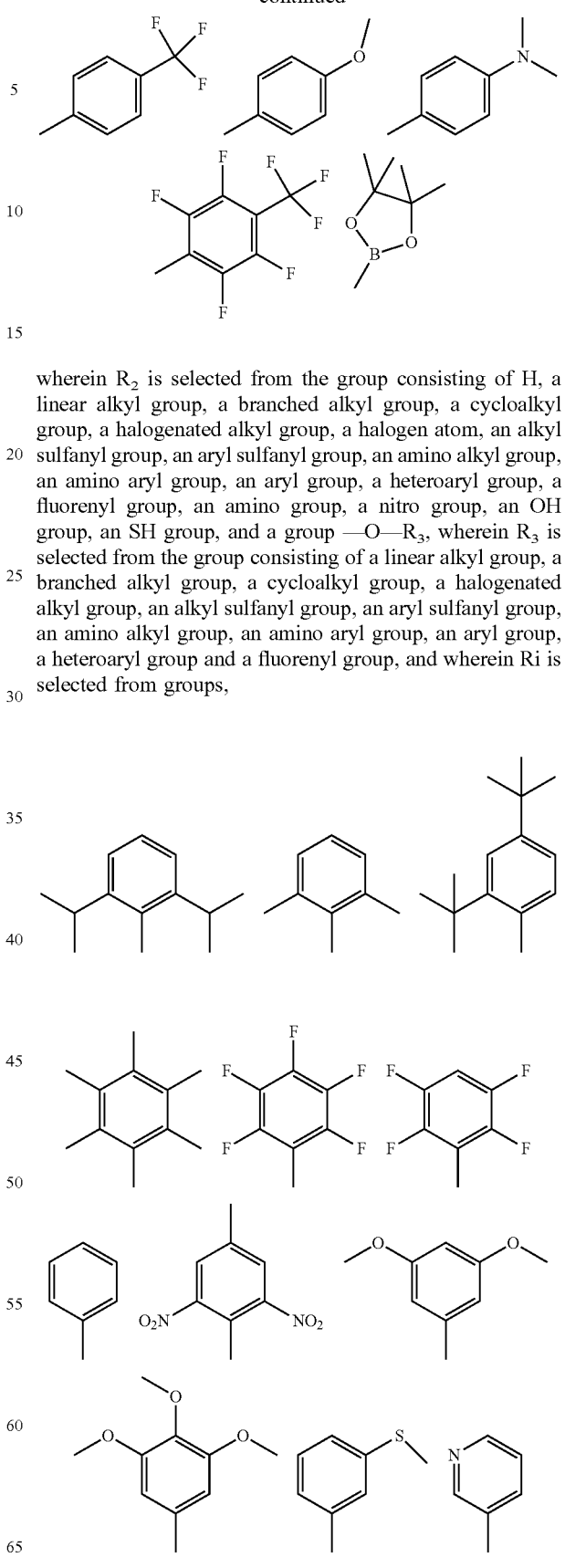

wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, and wherein Ri is selected from groups, -continued
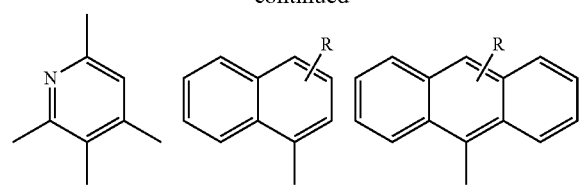
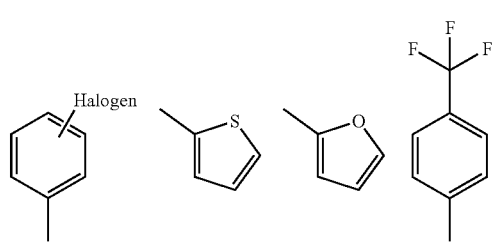
or wherein said at least one light emitter has one of structures,
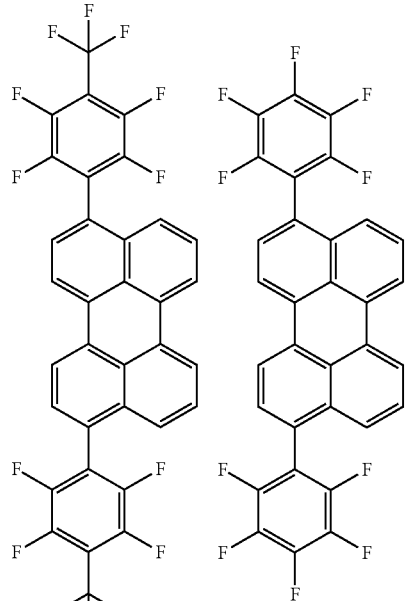
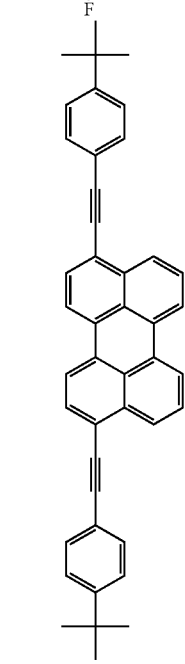
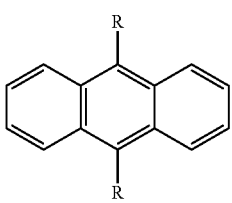
wherein R is a linear or branched alkyl group;
or wherein said light emitter has a structure of Formula (XXVI) or includes a molecule having the structure of Formula (XXVI)
Formula (XXVI)

wherein R is selected from groups,

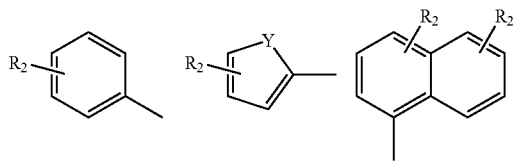

wherein Y is selected from the group consisting of $CH_2$, S, O, Se and N—$R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an OH group, an SH group, and a group —O—$R_3$, and wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, or wherein R is selected from groups,

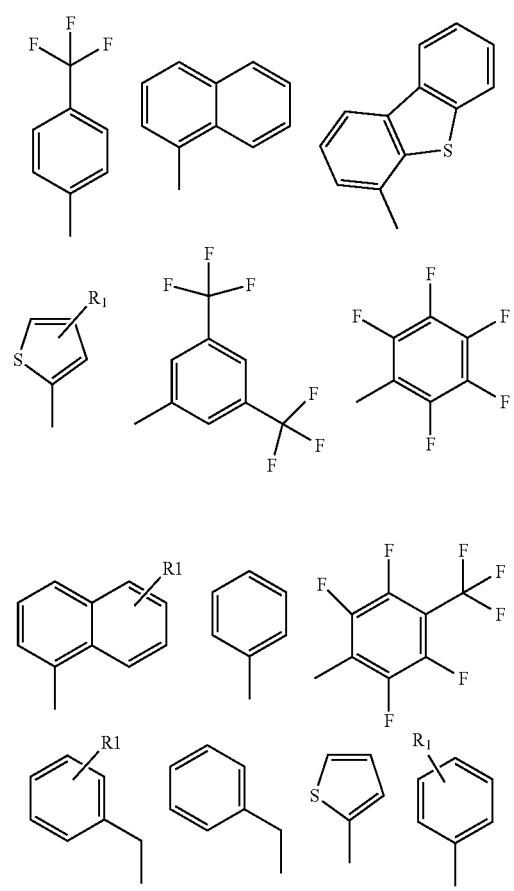

wherein $R_1$ is a linear or branched alkyl group;
or wherein said at least one light emitter has one of structures or includes a molecule having one of the structures,

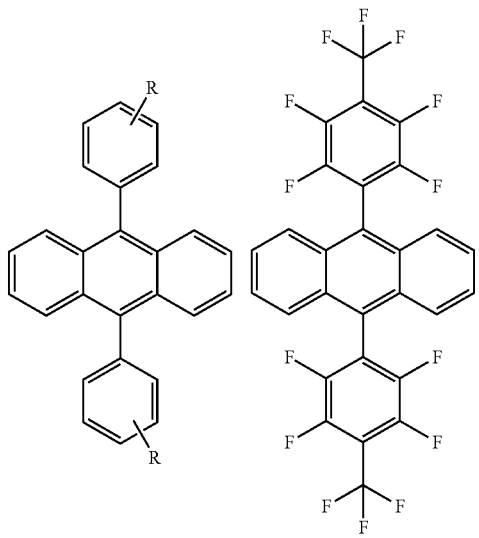

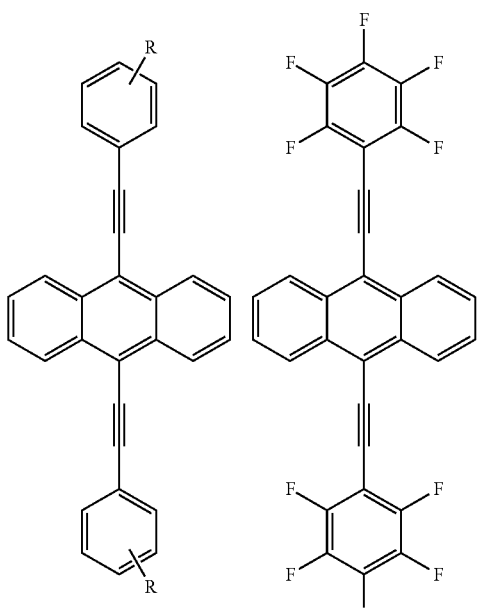

wherein R is a linear or branched alkyl group.

9. The nanoparticle according to claim 1, wherein said nanoparticle includes 1 to 4 metal nanoparticles and/or does not include metal nanoparticles that are in contact with each other.

10. The nanoparticle according to claim 1, wherein said at least one metal nanoparticle has a diameter in a range of from 1 to 100 nm and/or consists of a material selected from the group consisting of Ag, Au and Co and/or is magnetic.

11. The nanoparticle according to claim 1, further comprising:
at least one antioxidant selected from the group consisting of lipoic acid, vitamin E, a carotenoid, an ascorbic acid derivative soluble in an organic solvent.

12. The nanoparticle according to claim 1, further comprising:
   at least one functional group positioned at a surface of said matrix and selected from the group consisting of —COOH, —NH$_2$, —SH (thiol), —NHS, alkynyl, —N$_3$, aldehyde, ketone and biotin group.

13. The nanoparticle according to claim 1, further comprising:
   antibody molecules that are attached to a surface of said matrix and binds to a biomolecule.

14. The nanoparticle according to claim 1, further comprising:
   at least one antioxidant distributed in the said matrix.

15. The nanoparticle according to claim 1, wherein said polymeric organic matrix comprises one of a combination of a polystyrene and an oligostyrene, a combination of a polyethylene and an oligoethylene, and a combination of a polyphenylene and a polyphenylene dendrimer.

16. The nanoparticle according to claim 1, wherein said at least one light emitter is a molecule selected from the group consisting of an anthracene, a perylene, a perylene derivative, a coumarin and a BODIPY dye.

17. The nanoparticle according to claim 1, wherein said at least one light emitter has a structure of Formula (VII), Formula (VIII) or Formula (IX), or includes a molecule having the structure of Formula (VII), Formula (VIII) or Formula (IX):

Formula (VII)

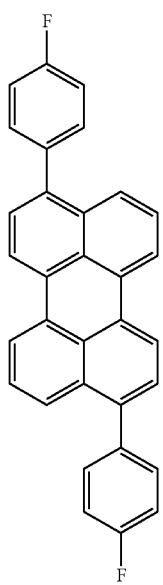

-continued

Formula (VIII)

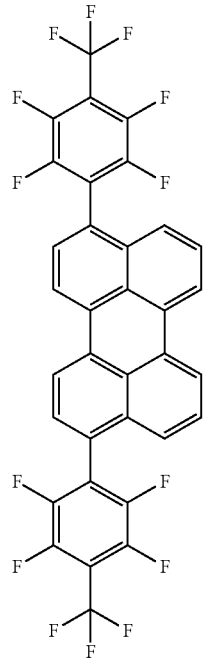

Formula (IX)

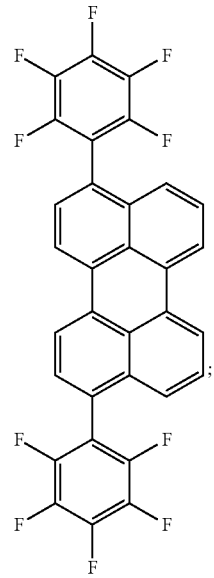

or wherein said at least one light emitter has a structure of Formula (XVII), Formula (XVIII), Formula (XIX), Formula (XX), Formula (XXI) or Formula (XXII), or includes a molecule having the structure of Formula (XVII), Formula (XVIII), Formula (XIX), Formula (XX), Formula (XXI) or Formula (XXII), Formula (XVII)
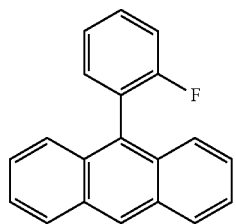
Formula (XVIII)
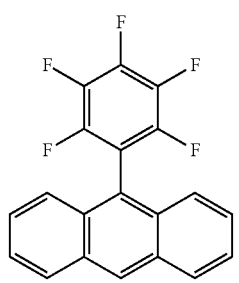
Formula (XIX)
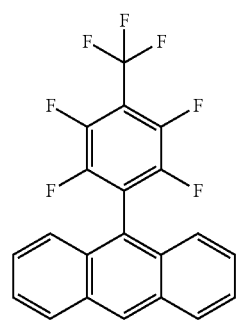
Formula (XX)
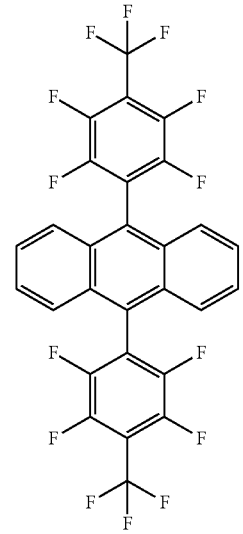
Formula (XXI)
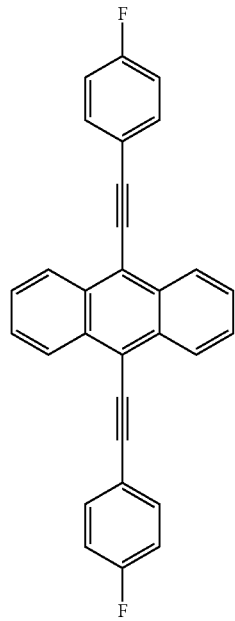
Formula (XXII)
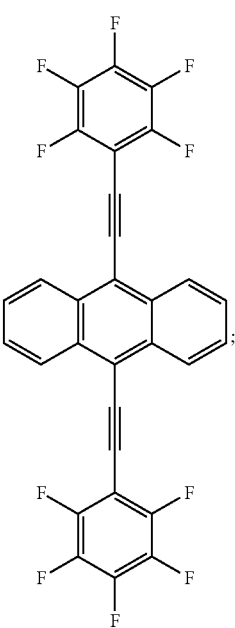
or wherein said at least one light emitter has one of structures or includes a molecule having one of the structures,

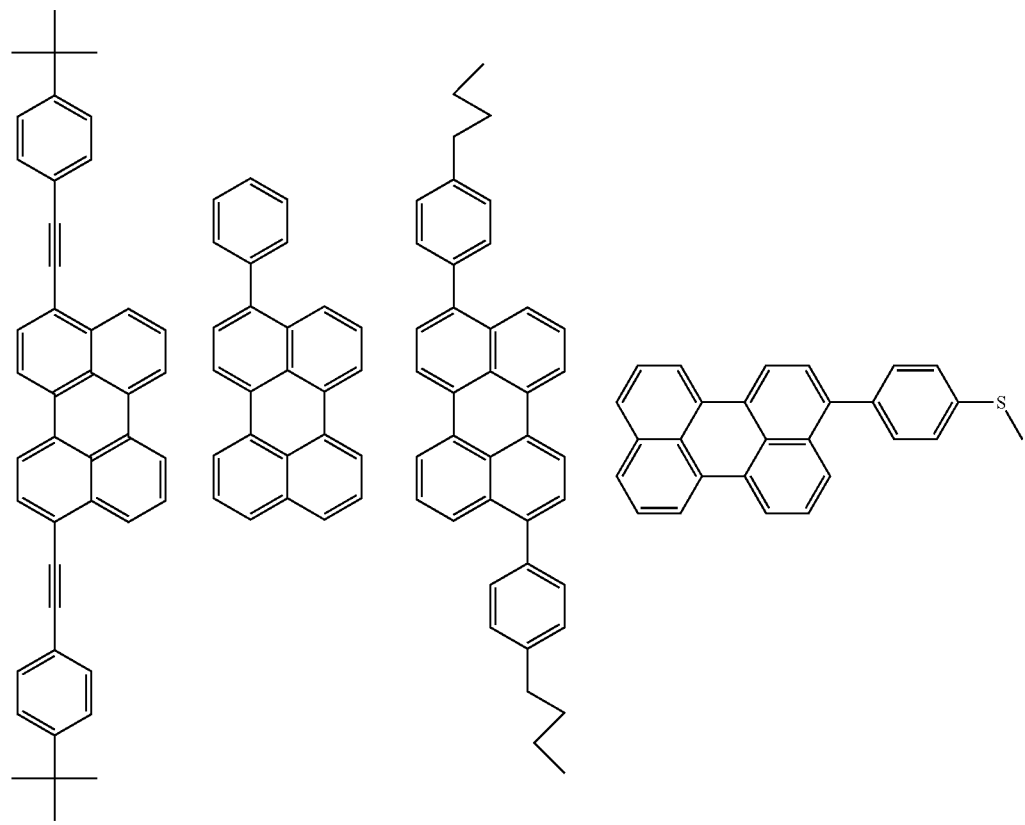
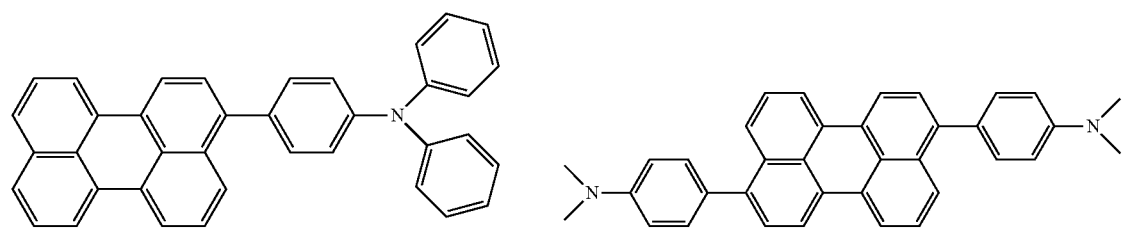
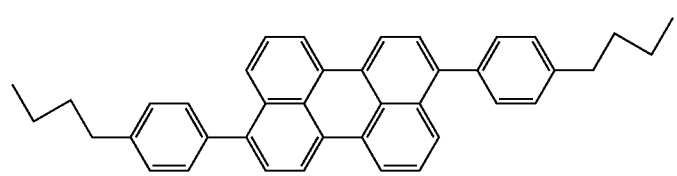
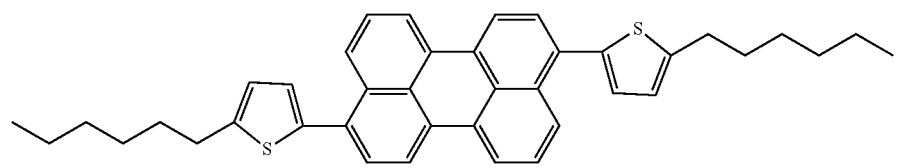

or wherein said light emitter has a structure of Formula (XXIII), (XXIV) or (XXV) or includes a molecule having the structure of Formula (XXIII), (XXIV) or (XXV),
Formula (XXIII)
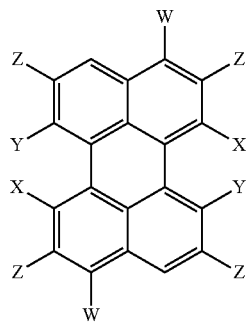
Formula (XXIV)
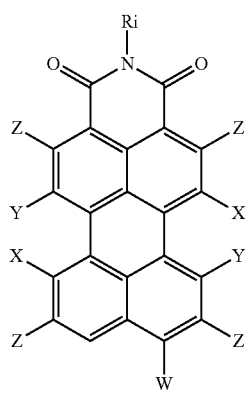
Formula (XXV)
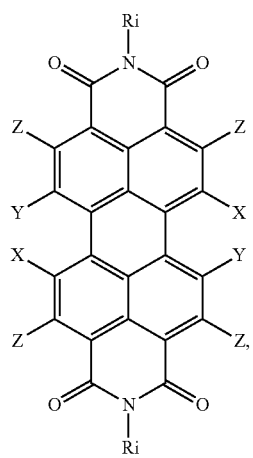
wherein X and Y in Formulas (XXIII-XXV) are independently selected from groups,
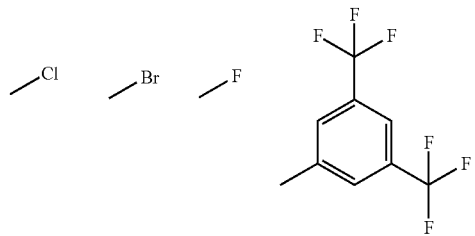
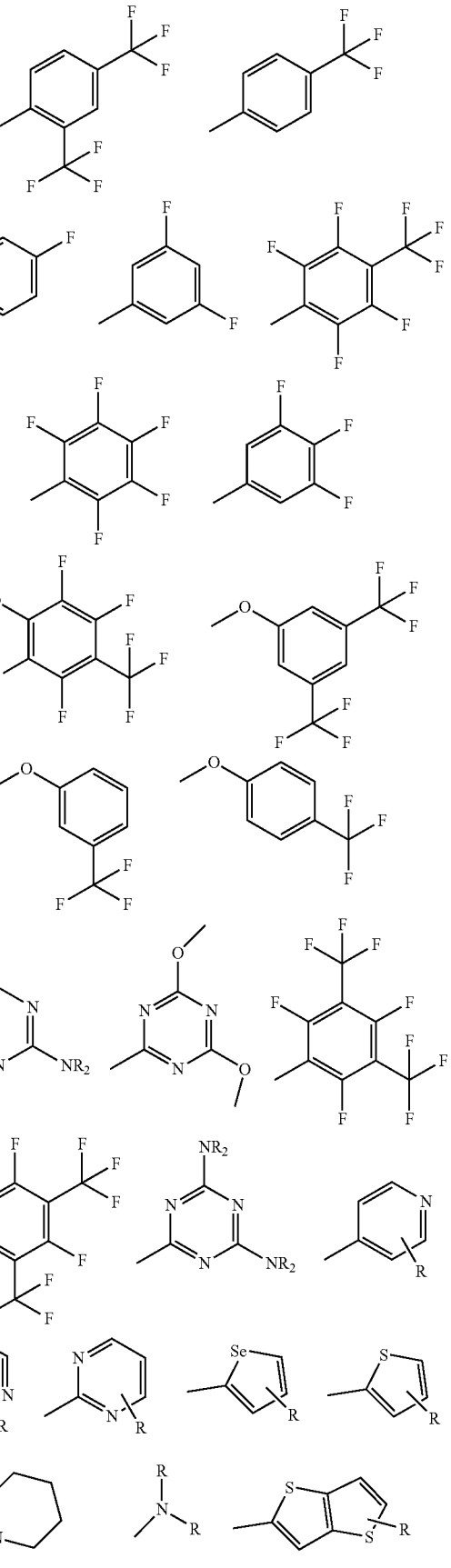

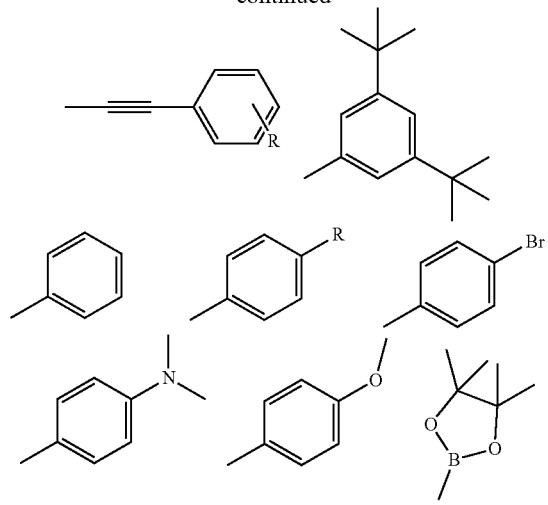

wherein R is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein Z in Formulas (XXIII-XXV) is selected from groups,

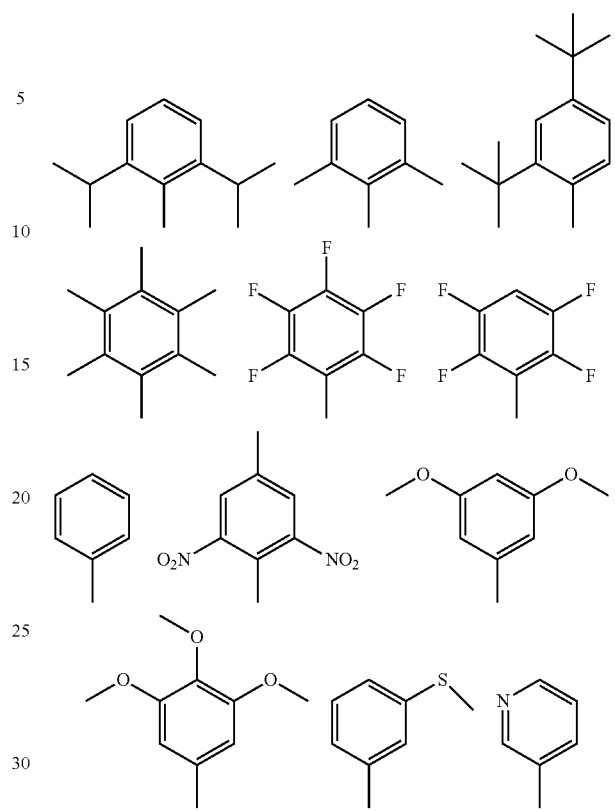

wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group, wherein, in particular, $R_2$ has not more than 6 carbon atoms, wherein Ri is selected from groups,

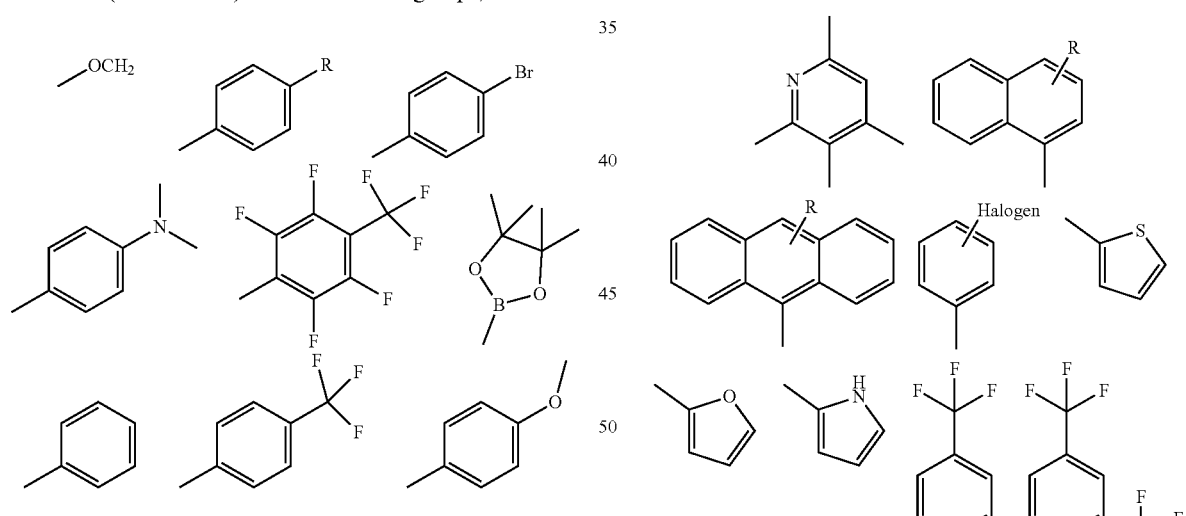

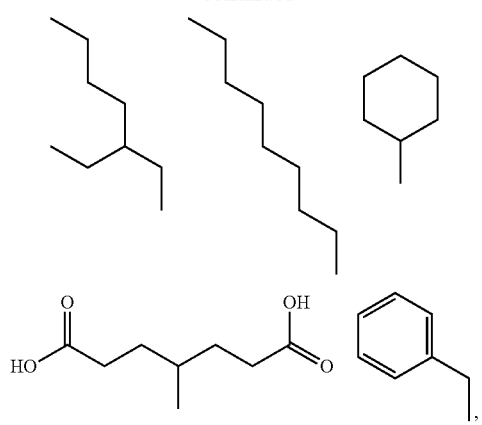
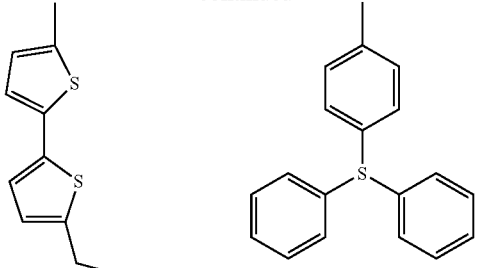
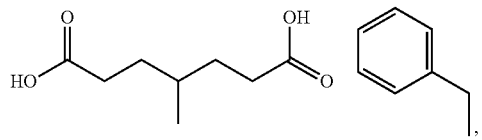
wherein W in Formulas (XXIII-XXV) is selected from groups,
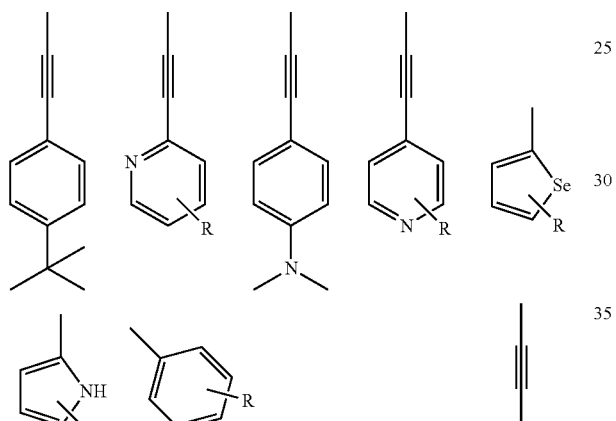
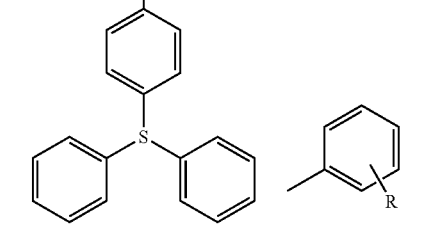
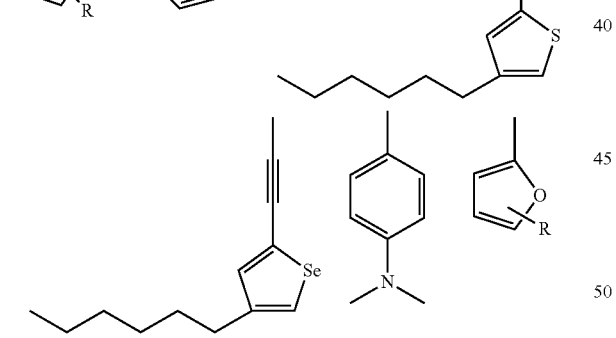
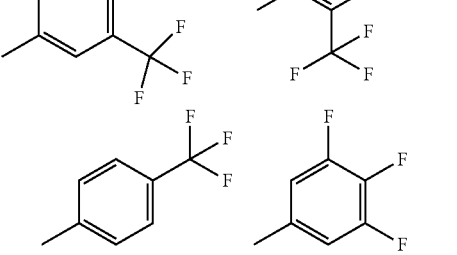
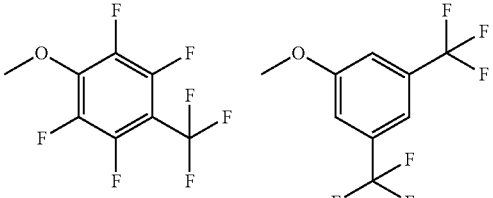
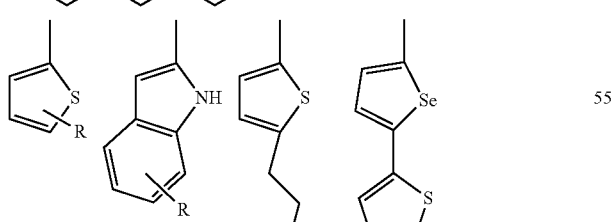
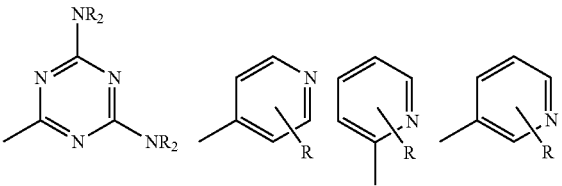

-continued

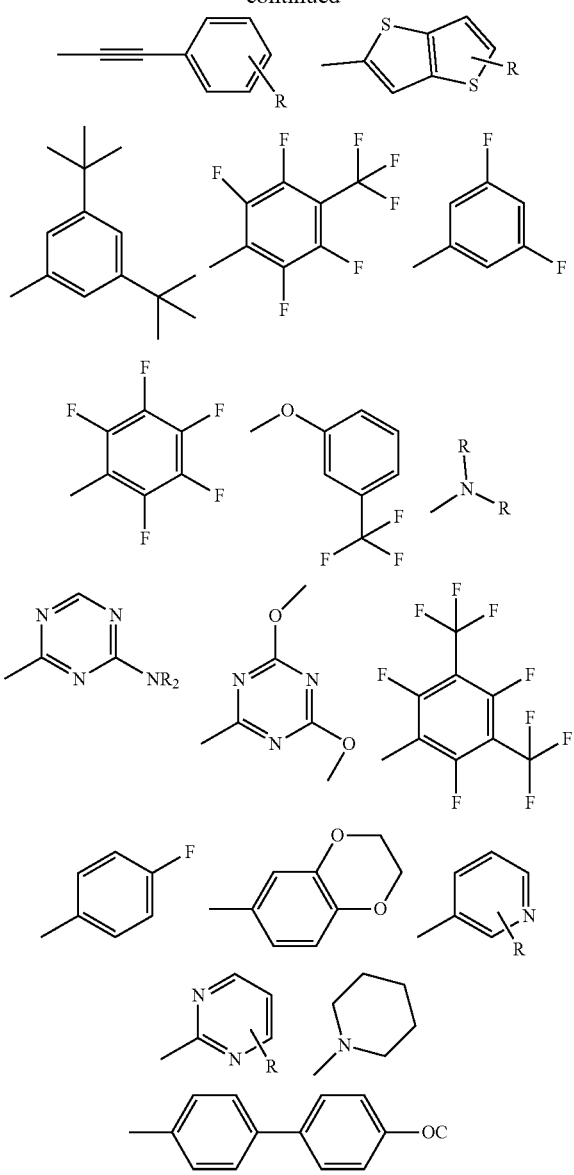

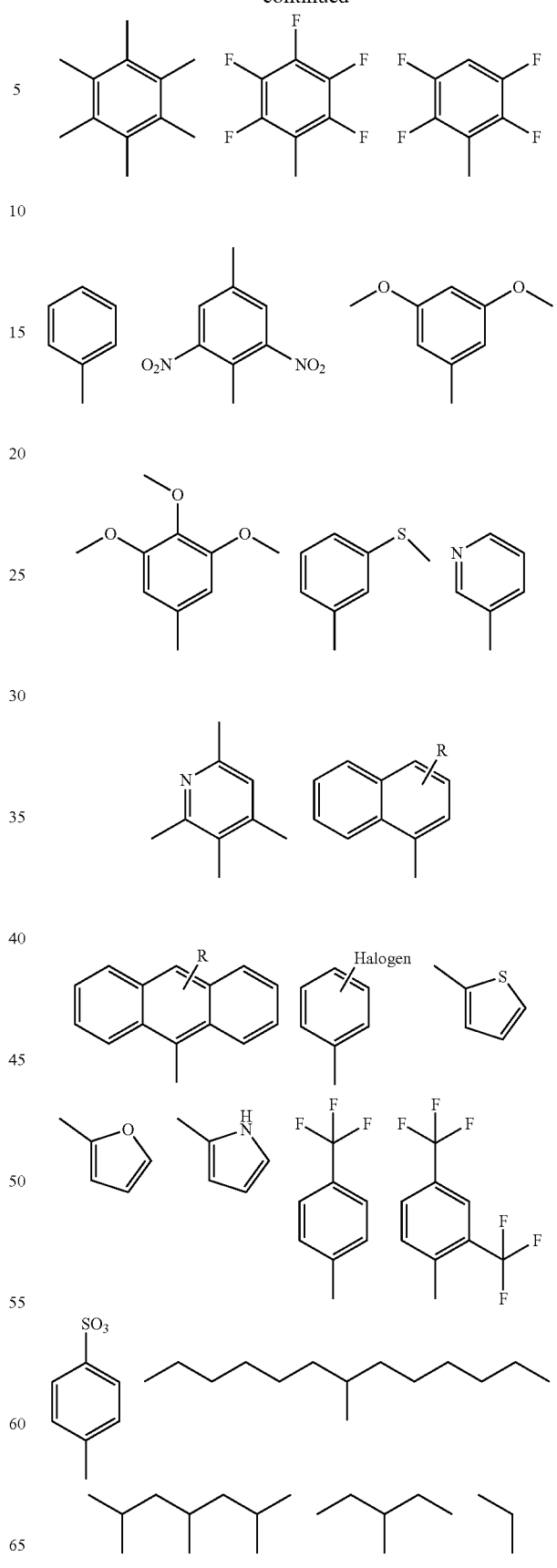

wherein R is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—R$_3$, wherein Ri is selected from groups, 101
-continued

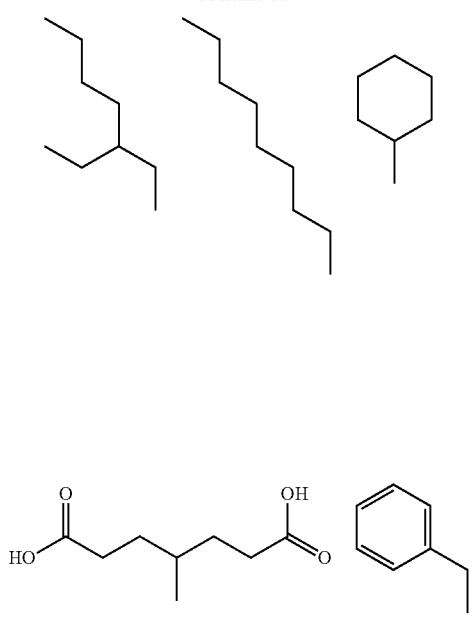

and wherein R₂ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an amino group, a nitro group, an OH group, an SH group, and a group —O—R₃, or wherein said at least one light emitter has one of structures,

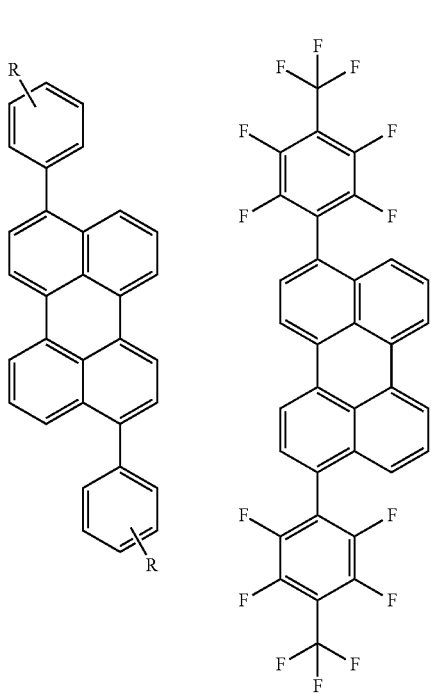

102
-continued

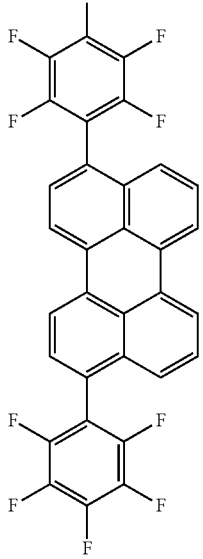 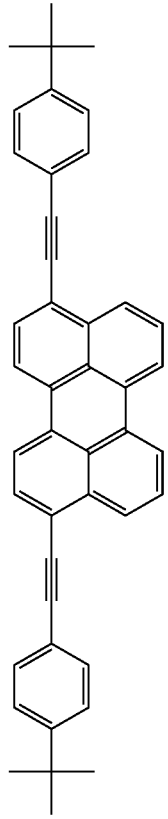

wherein R is a linear or branched alkyl group;
or wherein said light emitter has a structure of Formula (XXVI) or includes a molecule having the structure of Formula (XXVI),

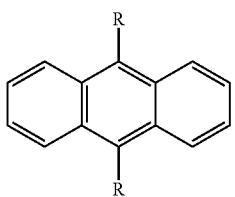

Formula (XXVI)

wherein R is selected from groups,

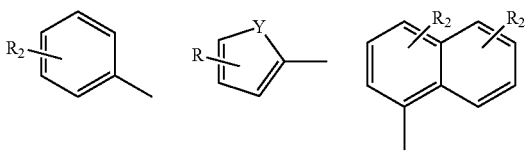

wherein Y is selected from the group consisting of CH₂, S, O, Se and N—R₂, and wherein R₂ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a heteroaryl group, a fluorenyl group, an OH group, an SH group, and a group —O—R₃, and wherein R₃ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a heteroaryl group and a fluorenyl group;

or wherein R is selected from groups,

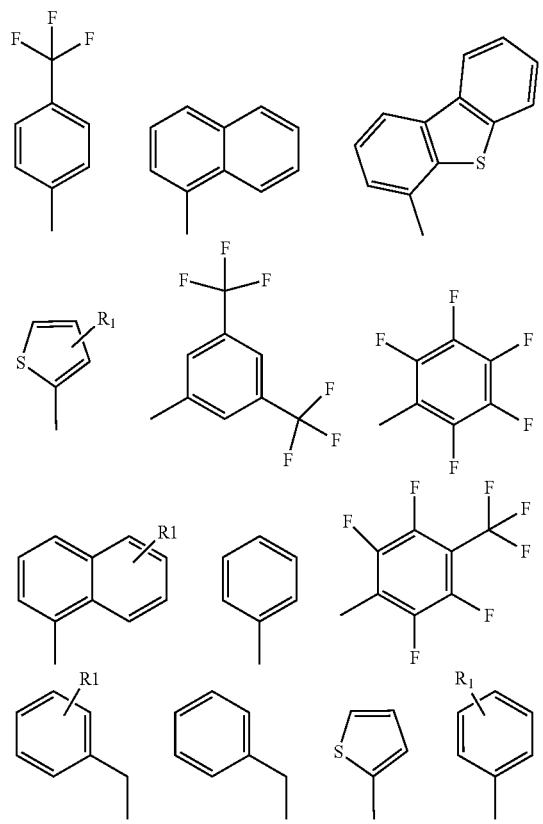

wherein $R_1$ is a linear or branched alkyl group;
or wherein said at least one light emitter has one of structures or includes a molecule having one of the structures,

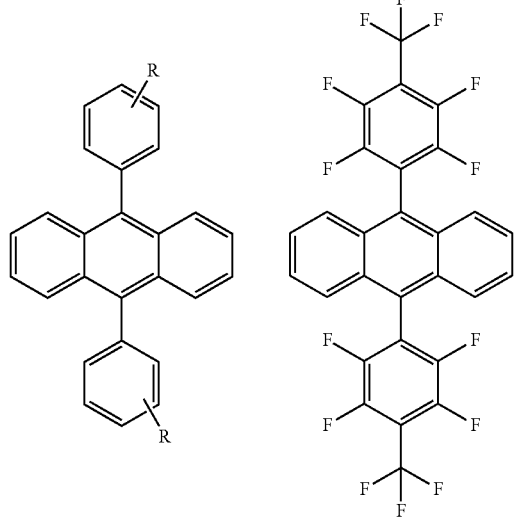

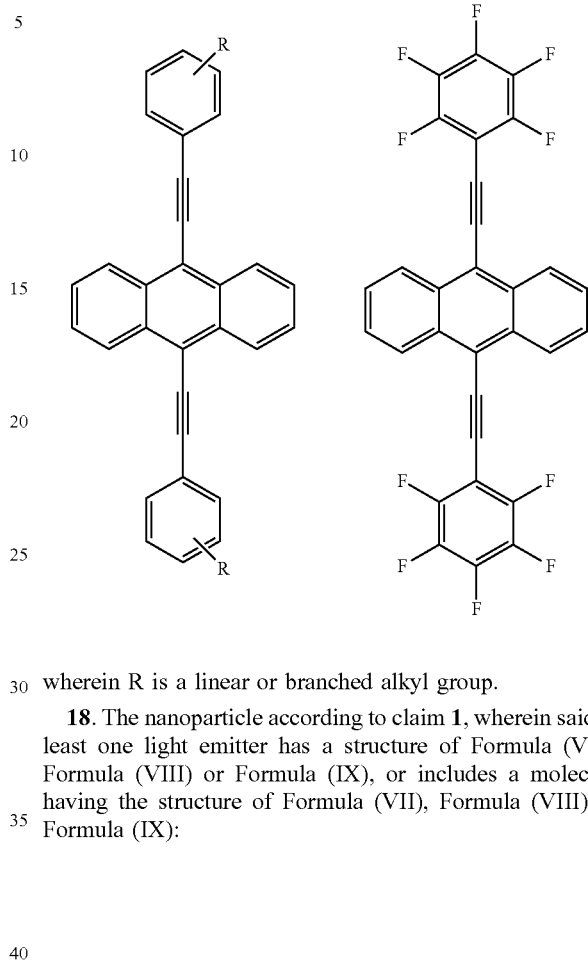

wherein R is a linear or branched alkyl group.

18. The nanoparticle according to claim 1, wherein said at least one light emitter has a structure of Formula (VII), Formula (VIII) or Formula (IX), or includes a molecule having the structure of Formula (VII), Formula (VIII) or Formula (IX):

Formula (VII)

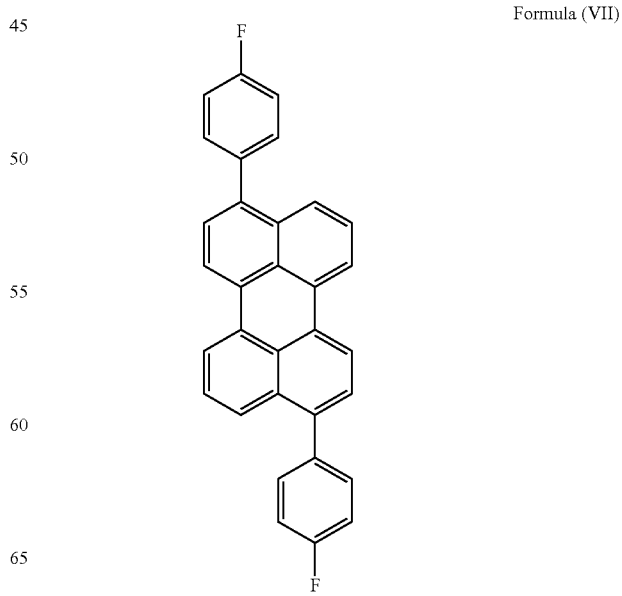

-continued
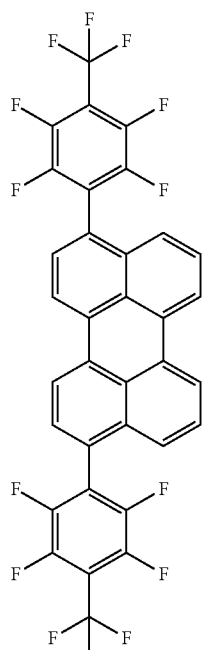
Formula (VIII)
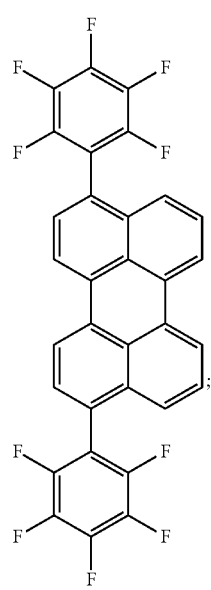
Formula (IX)
or wherein said at least one light emitter has a structure of Formula (XVII), Formula (XVIII), Formula (XIX), Formula (XX), Formula (XXI) or Formula (XXII), or includes a molecule having the structure of Formula (XVII), Formula (XVIII), Formula (XIX), Formula (XX), Formula (XXI) or Formula (XXII),
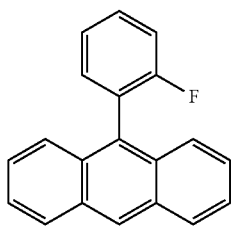
Formula (XVII)
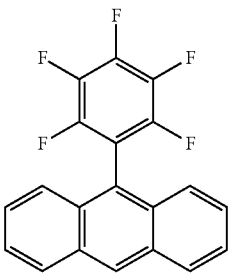
Formula (XVIII)

-continued
Formula (XIX)
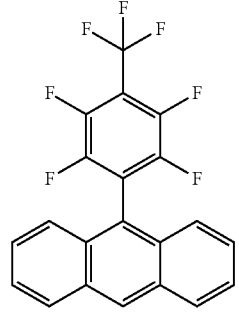
Formula (XX)
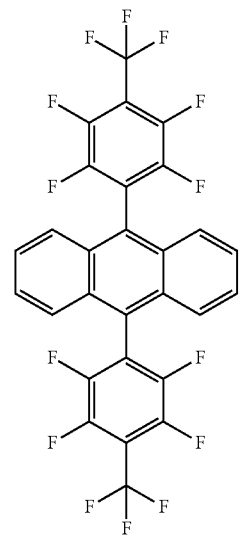
-continued
Formula (XXI)
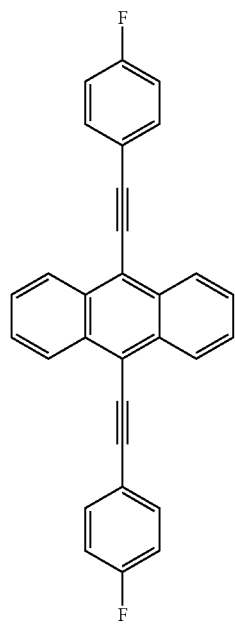
Formula (XXII)
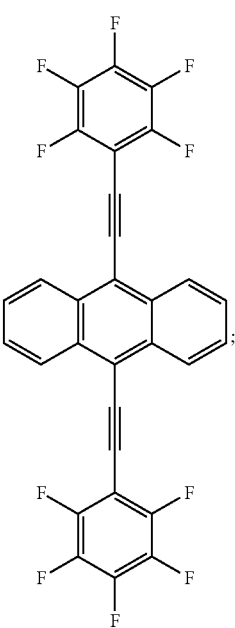
or wherein said at least one light emitter has one of structures or includes a molecule having one of the structures,

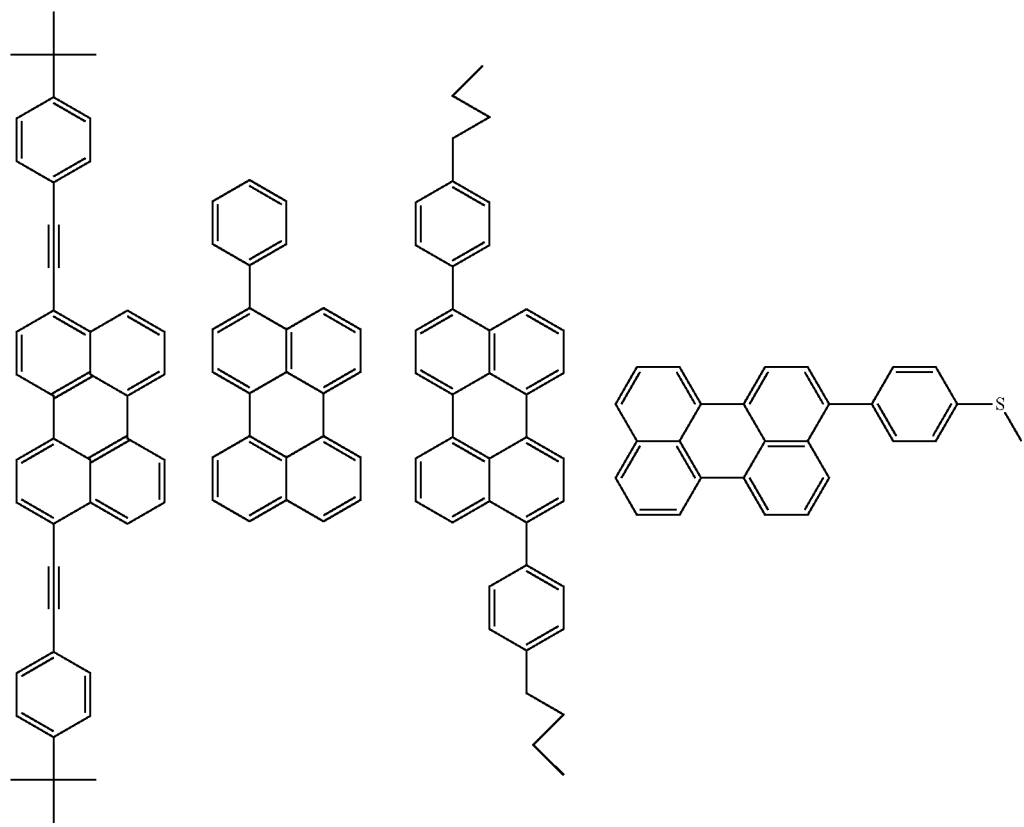
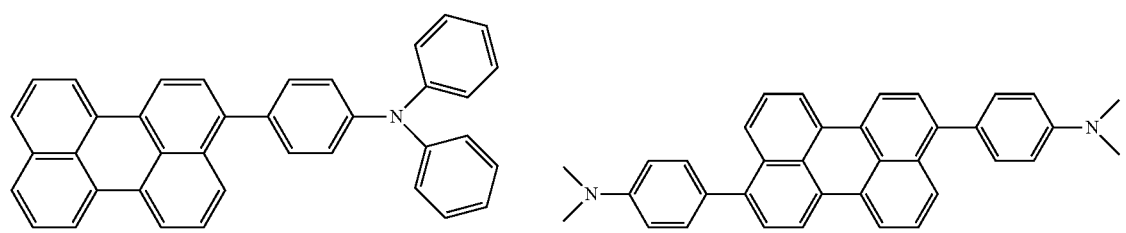
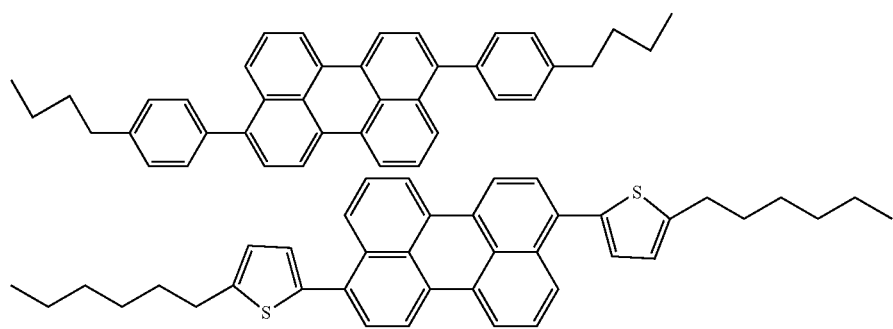

or wherein said at least one light emitter has one of structures,

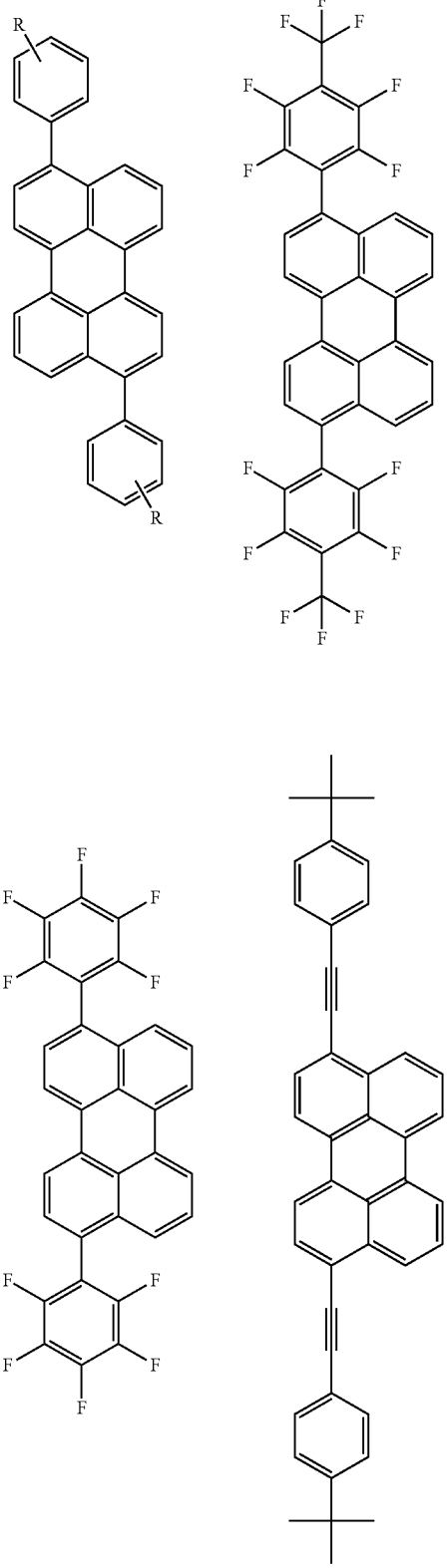

wherein R is a linear or branched alkyl group;
or wherein said at least one light emitter has one of structures or includes a molecule having one of the structures,

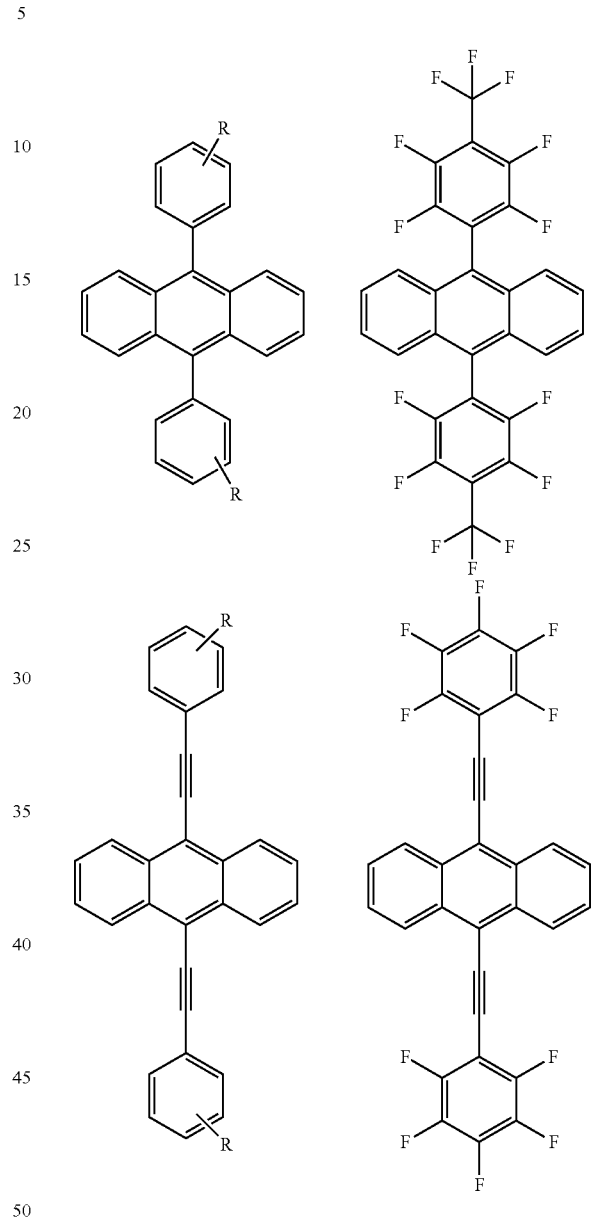

wherein R is a linear or branched alkyl group.

19. A method of producing nanoparticles, comprising:
providing a polymer or a combination of polymers or a combination of polymers with small molecules from which the polymeric organic matrix is to be formed, a stabilizing agent, at least one light emitter, and plasmonic metal nanoparticles;
preparing a dispersion of said plasmonic metal nanoparticles in an organic water-miscible solvent;
preparing a mixture of said polymer or combination of polymers or combination of polymers with small molecules from which the polymeric organic matrix is to be formed, said stabilizing agent, and said at least one light emitter in an organic water-miscible solvent;
adding said mixture of said polymer or combination of polymers or combination of polymers with small molecules, said stabilizing agent, said at least one light emitter to said dispersion of metal nanoparticles or vice versa, thus forming a mixture including said metal nanoparticles; and inducing said mixture including said plasmonic metal nanoparticles to form nanoparticles, thus forming a dispersion of nanoparticles, wherein said nanoparticles include a polymeric organic matrix with said at least one light emitter distributed therein, and said metal nanoparticles are enclosed in said polymeric organic matrix.

20. A sensing layer, comprising:

nanoparticles each comprising the nanoparticle of claim 1.

* * * * *